US008901117B2

(12) United States Patent
Wang et al.

(10) Patent No.: US 8,901,117 B2
(45) Date of Patent: *Dec. 2, 2014

(54) SMALL MOLECULE INHIBITORS OF MDM2 AND THE USES THEREOF

(75) Inventors: Shaomeng Wang, Saline, MI (US); Ke Ding, Guangzhou (CN); Yipin Lu, Ann Arbor, MI (US); Zaneta Nikolovska-Coleska, Ann Arbor, MI (US); Su Qiu, Ann Arbor, MI (US); Guoping Wang, Ann Arbor, MI (US); Dongguang Qin, Ann Arbor, MI (US); Sanjeev Kumar, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 100 days.

This patent is subject to a terminal disclaimer.

(21) Appl. No.: 13/336,047

(22) Filed: Dec. 23, 2011

(65) Prior Publication Data
US 2012/0101092 A1    Apr. 26, 2012

Related U.S. Application Data

(62) Division of application No. 12/822,829, filed on Jun. 24, 2010, now Pat. No. 8,088,931, which is a division of application No. 11/360,485, filed on Feb. 22, 2006, now Pat. No. 7,759,383.

(60) Provisional application No. 60/749,023, filed on Dec. 8, 2005, provisional application No. 60/655,135, filed on Feb. 22, 2005.

(51) Int. Cl.
*A61K 31/5377* (2006.01)
*A61K 31/407* (2006.01)
*A61K 31/437* (2006.01)
*A61K 31/4985* (2006.01)
*C07D 209/54* (2006.01)
*C07D 491/10* (2006.01)
*C07D 487/10* (2006.01)

(52) U.S. Cl.
CPC ............ *C07D 209/54* (2013.01); *C07D 491/10* (2013.01); *C07D 487/10* (2013.01)
USPC .................. 514/232.8; 514/249; 514/254.08; 514/278; 514/409

(58) Field of Classification Search
None
See application file for complete search history.

(56) References Cited

U.S. PATENT DOCUMENTS

| 3,219,661 | A | 11/1965 | Shavel, Jr. |
| 7,737,174 | B2 | 6/2010 | Wang |
| 2002/0039790 | A1 | 4/2002 | Keplinger et al. |
| 2006/0211757 | A1 | 9/2006 | Wang |
| 2011/0251252 | A1 | 10/2011 | Wang |
| 2012/0122947 | A1 | 5/2012 | Wang |

FOREIGN PATENT DOCUMENTS

| CN | 1410401 | 4/2003 |
| GB | 1056537 | 1/1967 |
| JP | 40-23184 | 10/1965 |
| JP | 44 4986 | 2/1969 |
| RU | 2084449 | 7/1997 |
| RU | 2186776 | 10/2002 |
| WO | 99/12904 | 3/1999 |
| WO | 03/051360 | 6/2003 |
| WO | 2005/110992 | 11/2005 |
| WO | 2006/091646 | 8/2006 |

OTHER PUBLICATIONS

Golub et al. Science (1999), vol. 286, pp. 531-536.*
Huff, Joel R. HIV Protease: A novel chemotherapeutic target for AIDS. Journal of Medicinal Chemistry, 34(8) (1991), 2305-2314.*
Lala et al. Cancer and Metastasis Reviews (1998), 17(1), 91-106.*
Ding et al., Journal of the American Chemical Society, 2005, 127 (29), pp. 10130-10131.*
Harley-Mason J, et al., 728. Hydroxytryptamines, Part IV, Synthesis and Reactions of 2-3'-oxindolylethylamines. Journal Chemical Society, 1958, pp. 3639-3642, p. 3639, compound (V).
Kabankin, A.S., et al., Analysis of relationship between structure and hepatoprotective activity of indole derivatires. Chemical and pharmaceutical magazine, 2005, vol. 39, No. 4, M., Volium, p. 24-28, table 1, compounds 4, 10 (learning sample), compound 1 (check sample).
Geise, B., et al., Radical cyclization reactions, Organice reactions (Hoboken, NJ, United States), 48, 1996, online, found from database ASC on STN, CA: 149:5550940, compounds with RN 159979-08-5, 159979-09-6.
Baxter E.W., et al., Reductive animations of carbonyl compounds with boronhydride and borane reducing agents. Organic reactions (Hoboken, NJ, Nited States, 59 (online) Found from database ASC on STN, CA: 149-5759820, compound with RN 1071179-22-0.
Ding, K., et al., "Synthesis of Spirooxindoles via asymmetric 1,3-dipolar cycloaddition", Tetrahedron Letters, Elsevier, Amsterdam, NL, Aug. 29, 2005, vol. 46, No. 35, pp. 5949-5951.
Database CAPLUS on STN, Chem. Abstr., Accession No. 1996:127543.
Pellegrini et al., "Total Synthesis of (+)-Elacomine and (–)-Isoelacomine, Two Hitherto Unnamed Oxindole Alkaloids from *Elaeagnus commutata*," Helvetica CHimica Acta 79:151-68 (1996).

(Continued)

*Primary Examiner* — Alicia L Otton
(74) *Attorney, Agent, or Firm* — Casimir Jones SC

(57) ABSTRACT

The invention relates to small molecules which function as inhibitors of the interaction between p53 and MDM2. The invention also relates to the use of these compounds for inhibiting cell growth, inducing cell death, inducing cell cycle arrest and/or sensitizing cells to additional agent(s).

7 Claims, 20 Drawing Sheets

(56) References Cited

OTHER PUBLICATIONS

Ding et al., "Structure-based design of spiro-oxindoles as potent, specific small-molecule inhibitors of the MDM2-p53 interaction," J. Med. Chem. 49:3432 (2006).
Chene, "Inhibiting the p53-MDM2 interaction: an important target for cancer therapy," Nature Rev. 3:102 (2003).
Vassilev et al., "In vivo activation of the p53 pathway by small-molecule antagonists of MDM2," Science 303:844 (2004).
Australian Patent Application No. 2006216780 First Examiner's Report dated Mar. 5, 2009.
Sebahar P.R. and William R.M., "the synthesis of Spirooxindole Pyrrolidines Via an Asymmetric Azomethine Ylide . . . " Heterocycles, 2002, vol. 58, pp. 563-575.
Onishi T., et al., "Concise, Asymmetric total Synthesis of Spirotryprostatin A," Tetrahedron, 1991, vol. 60, No. 42, pp. 2962-2983.
Cochard F., et al., "Synthesis of Substituted 1,2,3,4-Tetrahydro-1-thiacarbazole and . . . " European Journal of Organic Chemistry, 2002, vol. 20, pp. 3481-3490.
Wu and Farrelly, "Regulatory perspectives of Type II prodrug development and time-dependent toxicity management . . . " Toxicology 236: 1-6 (2007).
International Search Report and Written Opinion, PCT/US2007/019128, mailed Sep. 29, 2008.
Ding, et al., "Structure-Based Design of Potent Non-Peptide MdM2 Inhibitors" Journal of the American Chemical Society, Jul. 27, 2005, pp. 10130-10131.
Singapore Patent Application No. 200706163-3, Office Action dated Sep. 14, 2009.
Onishi, T.,. et al., "Concise, Asymmetric Total Synthesis of Spirotryprostatin A", Organic Letters, Jun. 26, 2003, vol. 5, No. 17, pp. 3135-3137.
Miyake, F.Y.., et al., "Preparation and Synthetic Application of 2-Halotryptophan Methyl Esters: Synthesis of Spirotryprostatin B", Angewandte Chemie/ International Edition, 2004, vol. 43, No. 40, pp. 5357-5360.
Sebahar, P.R., et al., "Asymmetric, Sterocontrolled total synthesis of (+) and (−)-spirotryprostatin B via a diastereoselective azomethine ylide . . . " Tetrahedron, Mar. 21, 2002, 6311-6322.
Lu, Y., et al., "Discovery of a Nanomolar Inhibitor of the Human Murine Double Minute 2(MDM2)-p53 Interaction through an Integrated Virtual Database Screening Strategy", Journal of Medicinal Chemistry, Jan. 9, 2006, vol. 49, No. 13, pp. 3759-3762.
Schubert, et al., European Journal of Pharmaceutics and Biopharmaceutics, 55(2003) 125-131.
Ban, et al., Chemical & Pharmaceutical Bulletin (1963), 4, 441-5.
Chene, Patrick, "Inhibiting the p53-MDM2 Interaction: An Important Target for Cancer Therapy," Nature Review: Cancer, Feb. 2003, vol. 3, pp. 102-109.
Garcia-Echeverria, Carlos, et al., "Discovery of Potent Antagonists of the Interaction between Human Double Minute 2 and Tumor Suppressor p53," American Chemical Society, (2000), 43, pp. 3205-3208.
Kussie, Paul H., "Structure of the MDM2 Oncoprotein Bound to the p53 Tumor Suppressor Transactivation Domain," Science, vol. 274, Nov. 8, 1996, pp. 948-953.
Nikolovska-Coleska, Zaneta, et al., "Development and optimization of a binding assay for the XIAP BIR3 domain using fluorescence polarization," Analytical Biochemistry 332 (2004), pp. 261-273.
Sebahar, Paul R., et al., "The Asymmetric Total Synthesis of (+)= and (−)-Spirotryprostatin B," J. Am. Chem. Soc. (2000), 122, pp. 5666-5667.
Usui, Takeo, et al., "Tryprostatin A, a specific and novel inhibitor of microtubule assembly," Biochem. J. (1998), 333, pp. 543-548.
Vassileve, Lyubomir T., et al., "In Vivo Activation of the p53 Pathway by Small-Molecule Antagonists of MDM2," Science, vol. 303, Feb. 6, 2004, pp. 844-848.
Vogelstein, Bert, et al., "Surfing the p53 network," Nature, vol. 408, Nov. 16, 2000, pp. 307-310.
Wu, Xiangwei, et al., "The p53-mdm-2 autoregulatory feedback loop," Genes & Development 7, pp. 1126-1132 (1993).
Eurasian Search Report (translated), EA Patent Application No. 200701771, Dated May 22, 2008.
Chem. Abstr. 130:311714, compound with RN 223663-19-2. Incze Maria et al. Intramolecular Mannich reaction of 2-oxotryptamines with acetone yielding spiro [indole-3, 3'-pyrrolidin]-2-ones. Collection of Czchoslovak Chemical Communications, 64 (2), 408-416 (English) 1999.
Chem. Abstr. 122:56269, compound with RN 160080-01-3. Pellegrini Claudio, et al. Synthesis of the oxindole alkaloid (−)-horsfiline. Tetrahedron: Asymmetry, 5(10), 1979-92 (English) 1994.
Chem. Abstr. 132:207995, compound with RN 6786-41-0, Somei Masanori, et al. Chemistry of indoles. 95. Preparation and a novel rearrangement reaction of 1, 2, 3, 4-tetrahydro-9-hydroxy-beta carboline, and their applications for the total synthesis of (+/−)-coerulescine. Heterocycles, 53(1), 7-10 (English) 2000.
Chem. Abstr. J 28:257595, compound with RN 6786-41-0. Cossy Janine E.E., et al. A convenient route to spiropyrrolidinyl-oxindole alkaloids via C-3 substituted enepyrrolidine carbamate radical cyclization. Tetrahedron Letters, 39(16), 2331-2332 (English) 1998.
Chem. Abstr. 51:29816, compound with RN 6786-41-0. Van Tamelen, et al. Spiro [pyrrolidine-3, 3'-oxindole and-2'-pseudoindoxyl]. Chemistry & Industry (London, United Kingdom) 1 145-6 (Unavailable) 1956.
Chem. Abstr. 138:401949, compound with RN 404871-51-8. Lizos Dimitrios E., et al. Concise synthesis of (−/−)-horsfiline and (+/−)-coerulescine by tandem cyclisation of iodoaryl alkenyl azides. Organic & Biomolecular Chemistry, 1(1), 117-122 (English) 2003.
136:247728, compound with RN 404871-51-8. Lizos Dimitrios, et al. A novel and economical route to (+/−)-horsfiline using an aryl iodoazide tandem radical cyclization strategy. Chemical Communications (Cambridge, United Kingdom) (24); 2732-2733 (English) 2001.
Chem. Abstr. 132:93510 compound with RN 254428-32-5, Alper Phil B. Facile, novel methodology for the synthesis of spiro [pyrrolidin-3, 3' oxindoles]: catalyzed ring expansion reactions of cyclopropanes by aldimines. Angewandte Chemie, International Edition, 38(21), 3186-3189 (English) 1999.
Chem. Abstr. 130:352456 compound with RN 225110-75-8, Edmondson Scott, et al. Total Synthesis of Spirotryprostatin A, Leading to the Discovery of Some Biologically Promising Analogs. Journal of the American Chemical Society, 121(10), 2147-2155 (English) 1999.
Chem. Abstr. 95:220205 compound with RN 79888-04-3, Doe De Maindreville Michele, et al. Syntheses of indole derivatives. VII. Synthesis and chemical reactions of the tetracyclic system common to alkaloids with an anilinocrylic ester chromophore. Bulletin de la Societe Chimique de France (5-6, Pt.2), 179-84 (French) 1981.
Chem. Abstr. 137:185435 compound with RN 449777-56-4, Grigg Ronald, et al. Spirooxindoles via bimetallic [Pd (O)/Ag(I)] catalytic intramolecular Heck-I, 3-dipolar cycloaddition cascade reactions. Tetrahedron letters, 43(14), 2605-2608 (English) 2002.
Onishi T., et al., "Concise, Asymmetric Total Synthesis of Spirotryprostatin A," Tetrahedron, 60 (2004) 9503-9515.
JP Office Action dated Jan. 12, 2012 for related JP Patent Application No. 2007-556414.
Wang, Haishan, et al., "A Biomimetic Total Synthesis of (−) Spirotryprostatin B and Related Studies," J. Org. Chem. 2000, vol. 65(15), pp. 4685-5693.
Muhammad, Ilias, et al., "Investigation of Uria Dc Gato I. 7-Deoxyloganic . . . ", Phtochemistry, 2001, vol. 57(5), p. 781-785.
Kuroda, Minpei, et al., "Cytotoxi Alkaloids from the Barks of *Ochrosia elliptica*," Natural Medicines 53 (5) 272 (1999).
Sharma, Perveen, "Alkaloids of *Amsonia brevifolia*," Phytochemistry, 1998, vol. 27 (11), pp. 3649-3652.
Symposium on the chemistry of natural products (JP Abstract only), 1996, vol. 38, pp. 49-54.
Leclerco, Joelle, et al., Screening of Cytotoxic Activities of Strychnos Alkaloids (Methods and Retults), Journal of Ethnopharmacology, 15(3) (1986) 305-316.
CA Abstract Compound CAS RN 701304-77-0 (2004).

(56) References Cited

OTHER PUBLICATIONS

Baxter E.W., et al., Reductive animations of carbonyl compounds with boronhydride and borane reducting agents. Organic reactions (Hoboken, NJ, United States, 59 (online) Found from database ASC on STN, CA: 149-5759820, compound with RN 1071179-22-0 (2002).

* cited by examiner

R = OMe, spirotryprostatin A
R = H, demethoxyspirotryprostatin A

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The residue at this position is linked to
```

```
            carboxyfluoroscein
<220> FEATURE:
<221> NAME/KEY: MISC_FEATURE
<222> LOCATION: (4)..(5)
<223> OTHER INFORMATION: The residues at these positions are linked to
      aminoisobutyric acid
<220> FEATURE:
<221> NAME/KEY: MISC_FEATURE
<222> LOCATION: (7)..(8)
<223> OTHER INFORMATION: The residues at these positions are linked to
      1-aminocyclopropane-1-carboxylic acid
<220> FEATURE:
<221> NAME/KEY: MISC_FEATURE
<222> LOCATION: (9)..(9)
<223> OTHER INFORMATION: The residue at this position is linked to NH2

<400> SEQUENCE: 1

Ala Ala Phe Met Tyr Trp Glu Leu Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (17)..(17)
<223> OTHER INFORMATION: The residue at this position is linked to NH2

<400> SEQUENCE: 2

Pro Leu Ser Gln Glu Thr Phe Ser Asp Leu Trp Lys Leu Leu Pro Glu
1               5                   10                  15

Asn
```

SMALL MOLECULE INHIBITORS OF MDM2 AND THE USES THEREOF

The present application claims priority to U.S. Provisional Application Ser. No. 60/402,718, filed Feb. 22, 2005, herein incorporated by reference.

BACKGROUND OF THE INVENTION

1. Field of the Invention

This invention is in the field of medicinal chemistry. In particular, the invention relates to small molecules which function as antagonists of the interaction between p53 and MDM2 and their use as a new class of therapeutics for the treatment of cancer and other diseases.

2. Related Art

The aggressive cancer cell phenotype is the result of a variety of genetic and epigenetic alterations leading to deregulation of intracellular signaling pathways (Ponder, Nature 411:336 (2001)). The commonality for all cancer cells, however, is their failure to execute an apoptotic program, and lack of appropriate apoptosis due to defects in the normal apoptosis machinery is a hallmark of cancer (Lowe et al., Carcinogenesis 21:485 (2000)). The inability of cancer cells to execute an apoptotic program due to defects in the normal apoptotic machinery is thus often associated with an increase in resistance to chemotherapy, radiation, or immunotherapy-induced apoptosis. Primary or acquired resistance of human cancer of different origins to current treatment protocols due to apoptosis defects is a major problem in current cancer therapy (Lowe et al., Carcinogenesis 21:485 (2000); Nicholson, Nature 407:810 (2000)). Accordingly, current and future efforts towards designing and developing new molecular target-specific anticancer therapies to improve survival and quality of life of cancer patients must include strategies that specifically target cancer cell resistance to apoptosis. In this regard, targeting crucial negative regulators that play a central role in directly inhibiting apoptosis in cancer cells represents a highly promising therapeutic strategy for new anticancer drug design.

The p53 tumor suppressor plays a central role in controlling cell cycle progression and apoptosis (Vogelstein et al., Nature 408:307 (2000)). It is an attractive therapeutic target for anticancer drug design because its tumor suppressor activity can be stimulated to eradicate tumor cells (Vogelstein et al., Nature 408:307 (2000); Chene, Nat. Rev. Cancer 3:102 (2003)). A new approach to stimulating the activity of p53 is through inhibition of its interaction with the protein MDM2 using non-peptide small molecule inhibitors (Chene, Nat. Rev. Cancer 3:102 (2003); Vassilev et al., Science 303:844 (2004)). MDM2 and p53 are part of an auto-regulatory feedback loop (Wu et al., Genes Dev. 7:1126 (1993)). MDM2 is transcriptionally activated by p53 and MDM2, in turn, inhibits p53 activity by at least three mechanisms (Wu et al., Genes Dev. 7:1126 (1993). First, MDM2 protein directly binds to the p53 transactivation domain and thereby inhibits p53-mediated transactivation. Second, MDM2 protein contains a nuclear export signal sequence, and upon binding to p53, induces the nuclear export of p53, preventing p53 from binding to the targeted DNAs. Third, MDM2 protein is an E3 ubiquitin ligase and upon binding to p53 is able to promote p53 degradation. Hence, by functioning as a potent endogenous cellular inhibitor of p53 activity, MDM2 effectively inhibits p53-mediated apoptosis, cell cycle arrest and DNA repair. Therefore, small-molecule inhibitors that bind to MDM2 and block the interaction between MDM2 and p53 can promote the activity of p53 in cells with a functional p53 and stimulate p53-mediated cellular effects such as cell cycle arrest, apoptosis, or DNA repair (Chene, Nat. Rev. Cancer 3:102 (2003); Vassilev et al., Science 303:844 (2004))

Although high-affinity peptide-based inhibitors have been successfully designed in the past (Garcia-Echeverria et al., Med. Chem. 43:3205 (2000)), these inhibitors are not druglike molecules because of their poor cell permeability and in vivo bioavailability. Despite intensive efforts by the pharmaceutical industry, high throughput screening strategies have had very limited success in identifying potent, non-peptide small molecule inhibitors. Accordingly, there is a need for non-peptide, drug-like, small molecule inhibitors of the p53-MDM2 interaction.

The design of non-peptide small-molecule inhibitors that target the p53-MDM2 interaction is currently being pursued as an attractive strategy for anti-cancer drug design (Chene, Nat. Rev. Cancer 3:102 (2003); Vassilev et al., Science 303:844 (2004)). The structural basis of this interaction has been established by x-ray crystallography (Kussie et al., Science 274:948 (1996)). The crystal structure shows that the interaction between p53 and MDM2 is primarily mediated by three hydrophobic residues (Phe19, Trp23 and Leu26) from p53 and a small, deep hydrophobic cleft in MDM2. This hydrophobic cleft is an ideal site for designing small-molecule inhibitors that can disrupt the p53-MDM2 interaction (Chene, Nat. Rev. Cancer 3:102 (2003)).

SUMMARY OF THE INVENTION

It is generally accepted that the inability of cancer cells or their supporting cells to undergo apoptosis in response to genetic lesions or exposure to inducers of apoptosis (such as anticancer agents and radiation) is a major factor in the onset and progression of cancer. The induction of apoptosis in cancer cells or their supporting cells (e.g., neovascular cells in the tumor vasculature) is thought to be a universal mechanism of action for virtually all of the effective cancer therapeutic drugs or radiation therapies on the market or in practice today. One reason for the inability of a cell to undergo apoptosis is a decrease in the tumor suppressor activity of p53, which in many instances is due to the inhibitory actions of MDM2 on p53 in tumor cells containing functional p53. The inhibition of p53 activity results in alterations in apoptosis pathways as well as cell cycle regulation.

The present invention contemplates that exposure of animals suffering from cancer to therapeutically effective amounts of drug(s) (e.g., small molecules) that increase the function(s) of p53 and p53-related proteins (e.g., p63, p73) by inhibiting the interaction between p53 or p53-related proteins and MDM2 or MDM2-related proteins (e.g., MDMX) will inhibit the growth of cancer cells or supporting cells outright and/or render such cells as a population more susceptible to the cell death-inducing activity of cancer therapeutic drugs or radiation therapies. In particular, the inhibitors of the invention may prolong the half-life of p53 by interfering with the p53-MDM2 interaction that would normally promote degradation of p53. The present invention contemplates that inhibitors of the interaction between p53 or p53-related proteins and MDM2 and MDM2-related proteins satisfy an unmet need for the treatment of multiple cancer types, either when administered as monotherapy to induce cell growth inhibition, apoptosis and/or cell cycle arrest in cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, combination treatment of animals with a therapeutically effective amount of a compound of the present invention and a course of an anticancer agent or radiation produces a greater tumor response and clinical benefit in such animals compared to those treated with the compound or anticancer drugs/radiation alone. Put another way, because the compounds will lower the apoptotic threshold of all cells, the proportion of cells that will successfully execute the apoptosis program in response to the apoptosis inducing activity of anticancer drugs/radiation is increased. Alternatively, the compounds of the present invention will be used to allow administration of a lower, and therefore less toxic and more tolerable, dose of an anticancer agent and/or radiation to produce the same tumor response/clinical benefit as the conventional dose of the anticancer agent/radiation alone. Since the doses for all approved anticancer drugs and radiation treatments are known, the present invention contemplates the various combinations of them with the present compounds. Also, since the compounds of the present invention may act at least in part by stimulating the pro-apoptotic and/or cell cycle-inhibiting activities of p53 and p53-related proteins, the exposure of cancer cells and supporting cells to therapeutically effective amounts of the compounds should be temporally linked to coincide with the attempts of cells to execute the apoptosis program in response to the anticancer agent or radiation therapy. Thus, in some embodiments, administering the compositions of the present invention in connection with certain temporal relationships, provides especially efficacious therapeutic practices.

In other embodiments of the invention, inhibitors of the interaction between p53 or p53-related proteins and MDM2 and MDM2-related proteins may protect normal (e.g., non-hyperproliferative) cells from the toxic effects of certain chemotherapeutic agents and radiation, possibly through the ability of the inhibitors to induce cell cycle arrest. In particular, the inhibitors of the invention may cause cell cycle arrest in cells comprising wild-type p53 while having no effect on cancer cells comprising mutated or deleted p53. This differential protective effect may allow for more effective treatment of cancer by allowing the use of higher doses or longer treatments of chemotherapeutic agents or treatments without increasing the toxic side effects of such treatment.

The present invention relates to compounds that are useful for inhibiting the interaction between p53 or p53-related proteins and MDM2 or MDM2-related proteins and increasing the sensitivity of cells to inducers of apoptosis and/or cell cycle arrest. In one particular embodiment, the compounds have Formula I:

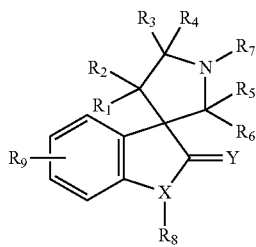

I or a pharmaceutically acceptable salt or prodrug thereof, wherein:

X is CH, O, N, or S, wherein $R_8$ is absent if X is O or S;
Y is O, S, or NR;
$R_1$, $R_2$, $R_3$, $R_4$, $R_5$, $R_6$, and $R_2$ are independently H or optionally substituted alkyl, cycloalkyl, alkenyl, cycloalkenyl, alkynyl, aryl, heterocyclic, $CO_2R'$, $OCOR'$, $CONR'R''$, $NR''COR'$, $NR'SO_2R''$, $SO_2NR'R''$, $(C=NR')NR''R'''$, or $NR'R''$; or
$R_7$ forms an aryl, cycloalkyl, or heterocyclic group with one of $R_5$ or $R_6$;
$R_8$ is H or optionally substituted alkyl, cycloalkyl, alkenyl, cycloalkenyl, alkynyl, aryl, heterocyclic, $CO_2R'$, $OCOR'$, $CONR'R''$, $SO_2NR'R''$, or $(C=NR')NR''R''$;
$R_9$ is one to four groups independently selected from H, F, Cl, Br, I, OH, $NO_2$, alkyl, cycloalkyl, alkenyl, cycloalkenyl, alkynyl, aryl, heterocyclic, $OR'$, $CO_2R'$, $OCOR'$, $CONR'R''$, $NR''COR'$, $NR'SO_2R''$, $SO_2NR'R''$, or $(C=NR')NR''R'''$, or $NR'R''$; and
each R', R'' and R''' is independently H or optionally substituted alkyl, cycloalkyl, alkenyl, cycloalkenyl, alkynyl, aryl, or heterocyclic; or
R' and R'', or R'' and R''', form a ring; or
when one of $R_3$ and $R_4$ is CONRR', then one of R and R' may further be $(CH_2)_n-R'$, $(CH_2)_n-NR'R''$, $(CH_2)_n-NR'COR''$, $(CH_2)_n-NR'SO_2R''$, $(CH_2)_n-NR'(C=NR'')NR'''$, $(CH_2)_n-COOH$, $(CH_2)_n-COOR'$, $(CH_2)_n-CONR'R''$, $(CH_2)_n-OR'$, $(CH_2)_n-SR'$, $(CH_2)_n-COR'$, $(CH_2)_n-SO_3H$, $(CH_2)_n-SONR'R''$, $(CH_2)_n-SO_2NR'R''$, $(CH_2CH_2O)_n-(CH_2)_m-OH$, $(CH_2CH_2O)_n-(CH_2)_m-OR'$, $(CH_2CH_2O)_n-(CH_2)_m-COOR'$, $(CH_2CH_2O)_n-(CH_2)_m-CONR'R''$, $(CH_2CH_2O)_n-(CH_2)_m-NR'R''$, $(CH_2CH_2O)_n-(CH_2)_m-NR'COR''$, $(CH_2CH_2O)_n-(CH_2)_m-NR'(C=NR'')NR'''$, $(CH_2CH_2O)_n-(CH_2)_m-NR'SO_2R''$, $(CH_2)_p-(CH_2CH_2O)_n-(CH_2)_m-OH$, $(CH_2)_p-(CH_2CH_2O)_n-(CH_2)_m-OR'$, $(CH_2)_p-(CH_2CH_2O)_n-(CH_2)_m-COOR'$, $(CH_2)_p-(CH_2CH_2O)_n-(CH_2)_m-CONR'R''$, $(CH_2)_p-(CH_2CH_2O)_n-(CH_2)_m-NR'R''$, $(CH_2)_p-(CH_2CH_2O)_n-(CH_2)_m-NR'COR''$, $(CH_2)_p-(CH_2CH_2O)_n-(CH_2)_m-NR'(C=NR'')NR'''$, $(CH_2)_p-(CH_2CH_2O)_n-(CH_2)_m-NR'SO_2R''$, —CO—R', —SOR', or —$SO_2R'$; and
n, m, and p are each independently 1-6.

The invention relates to compounds represented by Formula I, which are inhibitors of the interaction between p53 or p53-related proteins and MDM2 or MDM2-related proteins. The invention relates to the use of the compounds of the invention to induce cell cycle arrest and/or apoptosis in cells containing functional p53 or p53-related proteins. The invention also relates to the use of the compounds of the invention for sensitizing cells to additional agent(s), such as inducers of apoptosis and/or cell cycle arrest, and chemoprotection of normal cells through the induction of cell cycle arrest prior to treatment with chemotherapeutic agents. In one embodiment, the invention relates to methods of rendering a normal cell resistant to chemotherapeutic agents or treatments, comprising contacting the cell with a compound of the invention. In one embodiment, the invention relates to methods of protecting normal cells in an animal with a hyperproliferative disease from the toxic side effects of chemotherapeutic agents or treatments, comprising administering to said animal a compound of the invention. In a particular embodiment, the invention is directed to the treatment, amelioration, or prevention of disorders, side effects, or conditions caused by the administration of chemotherapeutic agents to normal noncancerous cells by administering to an animal undergoing chemotherapy a compound of the present invention. Examples of such disorders and conditions caused by chemotherapy include, without limitation, mucositis, stomatitis, xerostomia, gastrointestinal disorders, and alopecia.

The compounds of the invention are useful for the treatment, amelioration, or prevention of disorders, such as those responsive to induction of apoptotic cell death, e.g., disorders characterized by dysregulation of apoptosis, including hyperproliferative diseases such as cancer. In certain embodiments, the compounds can be used to treat, ameliorate, or prevent cancer that is characterized by resistance to cancer therapies (e.g., those cancer cells which are chemoresistant, radiation resistant, hormone resistant, and the like). In other embodiments, the compounds can be used to treat hyperproliferative diseases characterized by expression of functional p53 or p53-related proteins. In other embodiments, the invention relates to the use of the compounds of the invention to protect normal (e.g., non-hyperproliferative) cells from the toxic side effects of chemotherapeutic agents and treatments by the induction of cell cycle arrest in those cells.

The present invention provides pharmaceutical compositions comprising a compound of Formula I in a therapeutically effective amount to induce apoptosis in cells or to sensitize cells to inducers of apoptosis.

The invention further provides kits comprising a compound of Formula I and instructions for administering the compound to an animal. The kits may optionally contain other therapeutic agents, e.g., anticancer agents or apoptosis-modulating agents.

The invention also provides methods of making compounds of Formula I.

BRIEF DESCRIPTION OF THE DRAWINGS/FIGURES

The patent or application filed contains at least one drawing (FIG. 2) executed in color. Copies of this patent or patent application publication with color drawings(s) will be provided by the Office upon request and payment of the necessary fee.

DETAILED DESCRIPTION OF THE INVENTION

Figure 1:
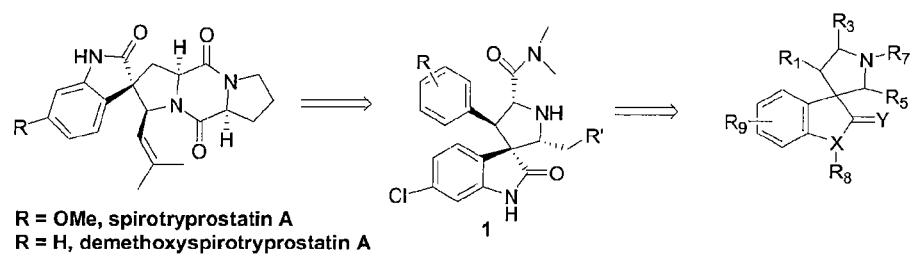
FIG. 1 shows the design of a new class of MDM2 inhibitors based upon spirotryprostatin A.

The present invention relates to compounds represented by Formula I, which function as inhibitors of the interaction between p53 or p53-related proteins and MDM2 or MDM2-related proteins. By inhibiting the negative effect of MDM2 or MDM2-related proteins on p53 or p53-related proteins, these compounds sensitize cells to inducers of apoptosis and/or cell cycle arrest and, in some instances, themselves induce apoptosis and/or cell cycle arrest. Therefore, the invention relates to methods of sensitizing cells to inducers of apoptosis and/or cell cycle arrest and to methods of inducing apoptosis and/or cell cycle arrest in cells, comprising contacting the cells with a compound of Formula I alone or in combination with additional agent(s), e.g., an inducer of apoptosis or a cell cycle disrupter. The invention further relates to methods of treating, ameliorating, or preventing disorders in an animal, such as those that are responsive to induction of apoptosis, comprising administering to the animal a compound of Formula I and additional agent(s), e.g., an inducer of apoptosis. Such disorders include those characterized by a dysregulation of apoptosis and those characterized by the proliferation of cells expressing functional p53 or p53-related proteins. In other embodiments, the invention relates to methods of protecting normal (e.g., non-hyperproliferative) cells in an animal from the toxic side effects of chemotherapeutic agents and treatments comprising administering to the animal a compound of Formula I.

The terms "anticancer agent" and "anticancer drug," as used herein, refer to any therapeutic agents (e.g., chemotherapeutic compounds and/or molecular therapeutic compounds), antisense therapies, radiation therapies, or surgical interventions, used in the treatment of hyperproliferative diseases such as cancer (e.g., in mammals).

The term "prodrug," as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, toxicity, lack of specificity, or limited bioavailability. Exemplary prodrugs comprise an active drug molecule itself and a chemical masking group (e.g., a group that reversibly suppresses the activity of the drug). Some preferred prodrugs are variations or derivatives of compounds that have groups cleavable under metabolic conditions. Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol), amides prepared by reaction of the parent acid compound with an amine, or basic groups reacted to form an acylated base derivative (e.g., a lower alkylamide).

The term "pharmaceutically acceptable salt," as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, a therapeutically effective amount preferably refers to the amount of a therapeutic agent that decreases the rate of tumor growth, decreases tumor mass, decreases the number of metastases, increases time to tumor progression, or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g., a compound of Formula I), an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least 10%, at least 20%, at least 30%, at least 40%, at least 50%, at least 60%, at least 70%, at least 80%, at least 90%, at least 100%, at least 150%, at least 200%, at least 350%, at least 300%, at least 350%, at least 400%, at least 450%, or at least 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, non-limiting examples of which include, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis. It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

The term "functional p53," as used herein, refers to wild-type p53 expressed at normal, high, or low levels and mutant p53 that retains at least 5% of the activity of wild-type p53, e.g., at least 10%, 20%, 30%, 40%, 50%, or more of wild-type activity.

The term "p53-related protein," as used herein, refers to proteins that have at least 25% sequence homology with p53, have tumor suppressor activity, and are inhibited by interaction with MDM2 or MDM2-related proteins. Examples of p53-related proteins include, but are not limited to, p63 and p73.

The term "MDM2-related protein," as used herein, refers to proteins that have at least 25% sequence homology with MDM2, and interact with and inhibit p53 or p53-related proteins. Examples of MDM2-related proteins include, but are not limited to, MDMX and HDM2.

The term "hyperproliferative disease," as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder"

refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "neoplastic disease," as used herein, refers to any abnormal growth of cells being either benign (non-cancerous) or malignant (cancerous).

The term "normal cell," as used herein, refers to a cell that is not undergoing abnormal growth or division. Normal cells are non-cancerous and are not part of any hyperproliferative disease or disorder.

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "apoptosis-modulating agents," as used herein, refers to agents which are involved in modulating (e.g., inhibiting, decreasing, increasing, promoting) apoptosis. Examples of apoptosis-modulating agents include proteins which comprise a death domain such as, but not limited to, Fas/CD95, TRAMP, TNF RI, DR1, DR2, DR3, DR4, DR5, DR6, FADD, and RIP. Other examples of apoptosis-modulating agents include, but are not limited to, TNFα, Fas ligand, antibodies to Fas/CD95 and other TNF family receptors, TRAIL (also known as Apo2 Ligand or Apo2L/TRAIL), antibodies to TRAIL-R1 or TRAIL-R2, Bcl-2, p53, BAX, BAD, Akt, CAD, PI3 kinase, PP1, and caspase proteins. Modulating agents broadly include agonists and antagonists of TNF family receptors and TNF family ligands. Apoptosis-modulating agents may be soluble or membrane bound (e.g. ligand or receptor). Preferred apoptosis-modulating agents are inducers of apoptosis, such as TNF or a TNF-related ligand, particularly a TRAMP ligand, a Fas/CD95 ligand, a TNFR-1 ligand, or TRAIL.

The inhibitors of the interaction between p53 and MDM2 of the present invention are compounds of Formula I:

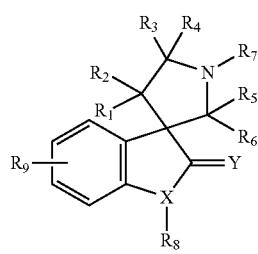

I or a pharmaceutically acceptable salt or prodrug thereof, wherein:

X is CH, O, N, or S, wherein $R_8$ is absent if X is O or S;

Y is O, S, or NR';

$R_1$, $R_2$, $R_3$, $R_4$, $R_5$, $R_6$, and $R_7$ are independently H or optionally substituted alkyl, cycloalkyl, alkenyl, cycloalkenyl, alkynyl, aryl, heterocyclic, $CO_2R'$, $OCOR'$, $CONR'R''$, $NR''COR'$, $NR'SO_2R''$, $SO_2NR'R''$, $(C=NR')NR''R'''$, or $NR'R''$; or $R_7$ forms an aryl, cycloalkyl, or heterocyclic group with one of $R_5$ or $R_6$;

$R_8$ is H or optionally substituted alkyl, cycloalkyl, alkenyl, cycloalkenyl, alkynyl, aryl, heterocyclic, $CO_2R'$, $OCOR'$, $CONR'R''$, $SO_2NR'R''$, or $(C=NR')NR''R'''$;

$R_9$ is one to four groups independently selected from H, F, Cl, Br, I, OH, $NO_2$, alkyl, cycloalkyl, alkenyl, cycloalkenyl, alkynyl, aryl, heterocyclic, $OR'$, $CO_2R'$, $OCOR'$, $CONR'R''$, $NR''COR'$, $NR'SO_2R''$, $SO_2NR'R''$, $(C=NR')NR''R'''$, or $NR'R''$; and each R', R'' and R''' is independently H or optionally substituted alkyl, cycloalkyl, alkenyl, cycloalkenyl, alkynyl, aryl, or heterocyclic; or R' and R'', or R'' and R''', form a ring; or when one of $R_3$ and $R_4$ is CONRR', then one of R and R' may further be $(CH_2)_n$—R', $(CH_2)_n$—NR'R'', $(CH_2)_n$—NR'COR'', $(CH_2)_n$—NR'SO_2R'', $(CH_2)_n$—NR'(C=NR'')NR'''$, $(CH_2)_n$—COOH, $(CH_2)_n$—COOR', $(CH_2)_n$—CONR'R'', $(CH_2)_n$—OR', $(CH_2)_n$—SR', $(CH_2)_n$—COR', $(CH_2)_n$—SO_3H, $(CH_2)_n$—SONR'R'', $(CH_2)_n$—SO_2NR'R'', $(CH_2CH_2O)_n$—$(CH_2)_m$—OH, $(CH_2CH_2O)_n$—$(CH_2)_m$—OR', $(CH_2CH_2O)_n$—$(CH_2)_m$—COOR', $(CH_2CH_2O)_n$—$(CH_2)_m$—CONR'R'', $(CH_2CH_2O)_n$—$(CH_2)_m$—NR'R'', $(CH_2CH_2O)_n$—$(CH_2)_m$—NR'COR'', $(CH_2CH_2O)_n$—$(CH_2)_m$—NR'(C=NR'')NR''', $(CH_2CH_2O)_n$—$(CH_2)_m$—NR'SO_2R'', $(CH_2)_p$—$(CH_2CH_2O)_n$—$(CH_2)_m$—OH, $(CH_2)_p$—$(CH_2CH_2O)_n$—$(CH_2)_m$—OR', $(CH_2)_p$—$(CH_2CH_2O)_n$—$(CH_2)_m$—COOR', $(CH_2)_p$—$(CH_2CH_2O)_n$—$(CH_2)_m$—CONR'R'', $(CH_2)_p$—$(CH_2CH_2O)_n$—$(CH_2)_m$—NR'R'', $(CH_2)_p$—$(CH_2CH_2O)_n$—$(CH_2)_m$—NR'COR'', $(CH_2)_p$—$(CH_2CH_2O)_n$—$(CH_2)_m$—NR'(C=NR'')NR''', $(CH_2)_p$—$(CH_2CH_2O)_n$—$(CH_2)_m$—NR'SO_2R'', —CO—R', —SOR', or —SO_2R'; and n, m, and p are each independently 1-6.

In a more particular embodiment, one of $R_1$ and $R_2$ is a substituted or unsubstituted aryl (e.g., phenyl), substituted or unsubstituted heteroaryl, cycloalkyl, straight or branched alkyl, amide or ester.

In another embodiment, one of $R_5$ and $R_6$ is a $C_{3-18}$ alkyl group, e.g., propyl, isopropyl, sec-butyl, tert-butyl, isopentyl, cyclopentyl, norbornyl, or adamantyl, or a 5- or 6-membered aryl or heteroaryl group.

In another embodiment, the compounds of Formula I have a stereochemical structure as shown in Formula II or Formula III:

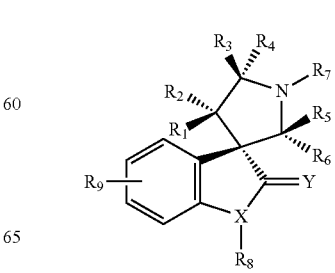

II

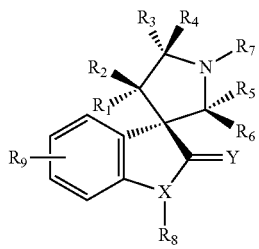
III

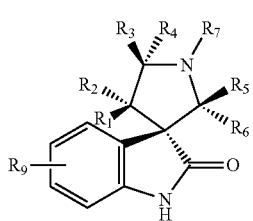
VIII or a pharmaceutically acceptable salt or prodrug thereof.

In one embodiment, the compounds of Formula I have Formula IV:

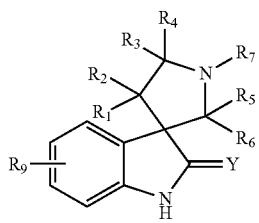
IV

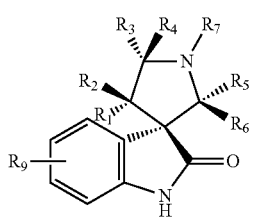
IX or a pharmaceutically acceptable salt or prodrug thereof.

In one embodiment, the compounds of Formula I have Formula X:

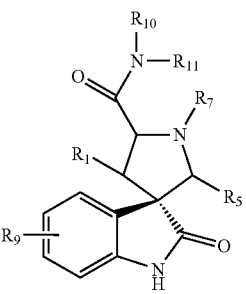
X wherein $R_1$-$R_9$ and Y are as defined above.

In another embodiment, the compounds of Formula IV have a stereochemical structure as shown in Formula V or Formula VI:

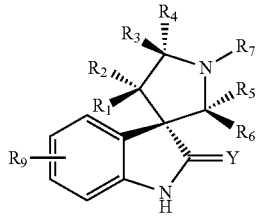
V

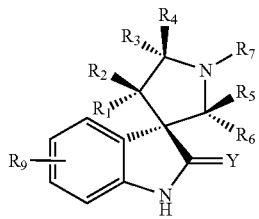
VI or a pharmaceutically acceptable salt or prodrug thereof.

In one embodiment, the compounds of Formula I have Formula VII:

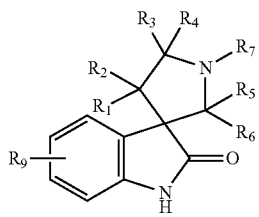
VII wherein $R_1$-$R_9$ are as defined above.

In another embodiment, the compounds of Formula VII have a stereochemical structure as shown in Formula VIII or Formula IX:

wherein:

$R_1$, $R_5$, $R_7$, and $R_9$ are as defined above;

$R_{10}$ and $R_{11}$ are independently H, OH or optionally substituted alkyl, cycloalkyl, alkenyl, cycloalkenyl, alkynyl, aryl, heterocyclic, $(CH_2)_n$—R', $(CH_2)_n$—NR'R", $(CH_2)_n$—NR'COR", $(CH_2)_n$—NR'SO$_2$R", $(CF_{12})_n$—NR'(C=NR")NR'", $(CH_2)_n$—COOH, $(CH_2)_n$—COOR', $(CH_2)_n$—CONR'R", $(CH_2)_n$—OR', $(CH_2)_n$—SR', $(CH_2)_n$—COR', $(CH_2)_n$—SO$_3$H, $(CH_2)_n$—SONR'R", $(CH_2)_n$—SO$_2$NR'R", $(CH_2CH_2O)_n$—$(CH_2)_m$—OH, $(CH_2CH_2O)_n$—$(CH_2)_m$—OR', $(CH_2CH_2O)_n$—$(CH_2)_m$—COOR', $(CH_2CH_2O)_n$—$(CH_2)_m$—CONR'R", $(CH_2CH_2O)_n$—$(CH_2)_m$—NR'R", $(CH_2CH_2O)_n$—$(CH_2)_m$—NR'COR", $(CH_2CH_2O)_n$—$(CH_2)_m$—NR'(C=NR")NR'", $(CH_2CH_2O)_n$—$(CH_2)_m$—NR'SO$_2$R", $(CH_2)_p$—$(CH_2CH_2O)_n$—$(CH_2)_m$—OH, $(CH_2)_p$—$(CH_2CH_2O)_n$—$(CH_2)_m$—OR', $(CH_2)_p$—$(CH_2CH_2O)_n$—$(CH_2)_m$—COOR', $(CH_2)_p$—$(CH_2CH_2O)_n$—$(CH_2)_m$—CONR'R", $(CH_2)_p$—$(CH_2CH_2O)_n$—$(CH_2)_m$—NR'R", $(CH_2)_p$—$(CH_2CH_2O)_n$—$(CH_2)_m$—NR'COR", $(CH_2)_p$—$(CH_2CH_2O)_n$—$(CH_2)_m$—NR'(C=NR")NR'", $(CH_2)_p$—$(CH_2CH_2O)_n$—$(CH_2)_m$—NR'SO$_2$R", —CO—R', —SOR', or —SO$_2$R'; and n, m, and p are each independently 1-6.

In a further embodiment, the compounds of Formula I have one of Formulae XI-XXVI:

XI
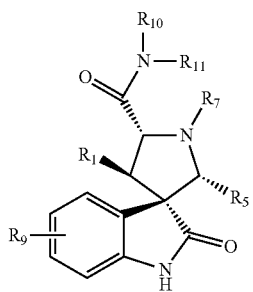
XVI
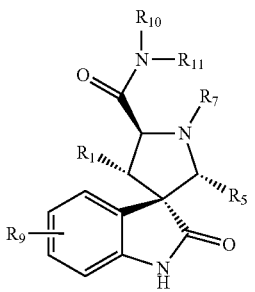
XII
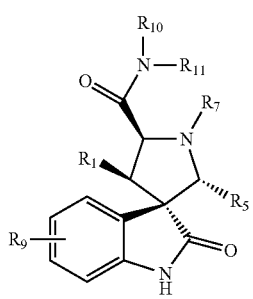
XVII
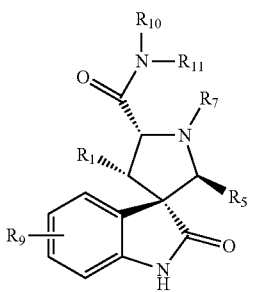
XIII
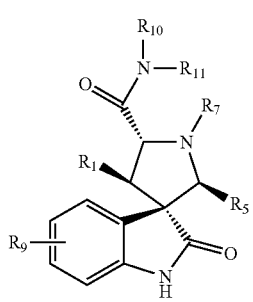
XVIII
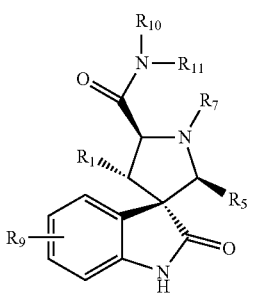
XIV
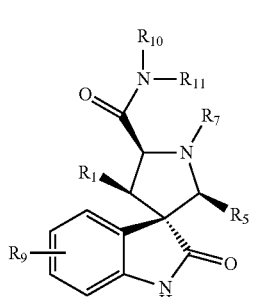
XIX
XV
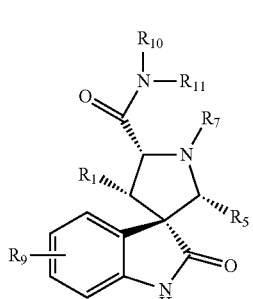
XX
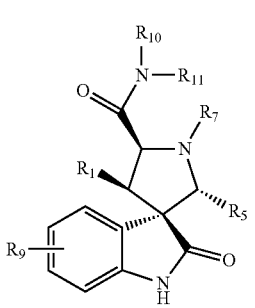

-continued

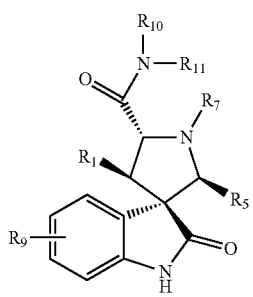
XXI

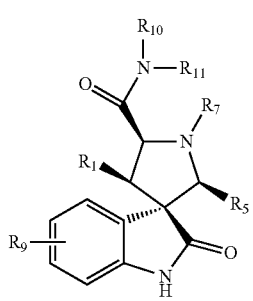
XXII

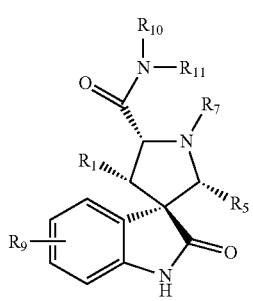
XXIII

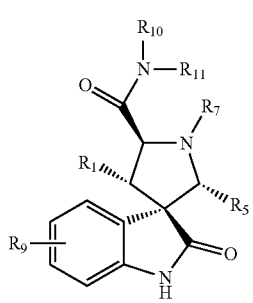
XXIV

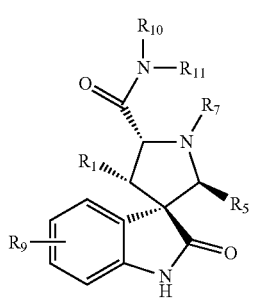
XXV

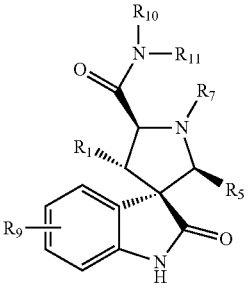
XXVI wherein $R_1$, $R_5$, $R_7$, $R_9$, $R_{10}$, and $R_{11}$ are as defined above.

In another embodiment, the compounds of Formula I have one of Formulae XXVII and XXVIII:

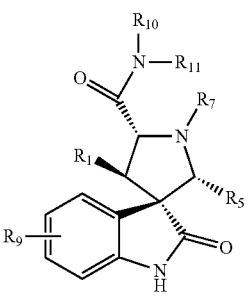
XXVII

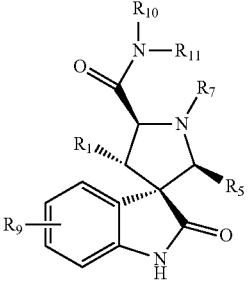
XXVIII wherein $R_1$, $R_5$, $R_7$, $R_9$, $R_{10}$, and $R_{11}$ are as defined above.

In another embodiment, the compounds of Formula I have Formula XXIX:

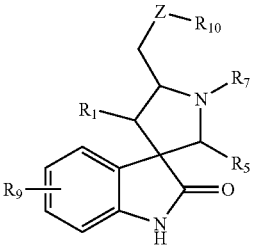
XXIX wherein:

Z is O, NH, NR', CH$_2$, CHR', or CR'R''; and $R_1$, $R_5$, $R_7$, $R_9$, and $R_{10}$ are as defined above.

In a further embodiment, the compounds of Formula I have one of Formulae XXX-XLV:

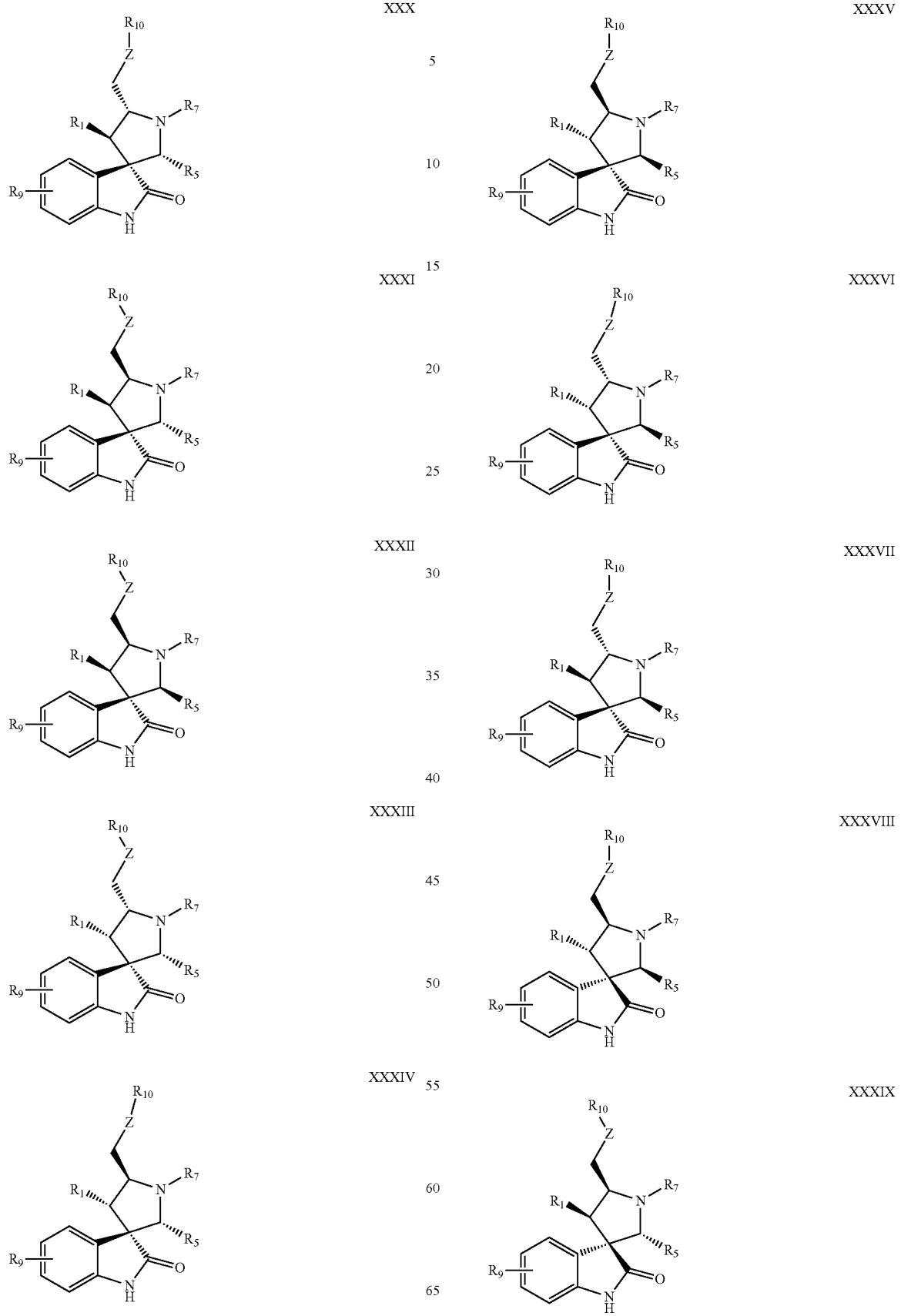

XL

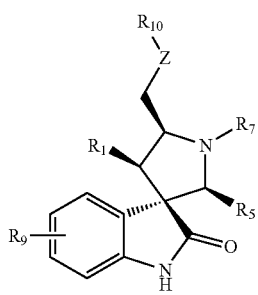

XLI

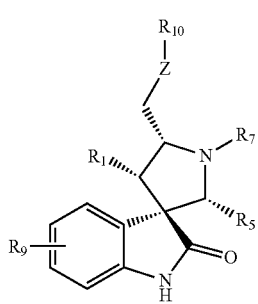

XLII

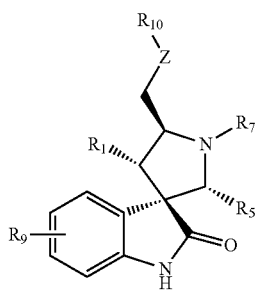

XLIII

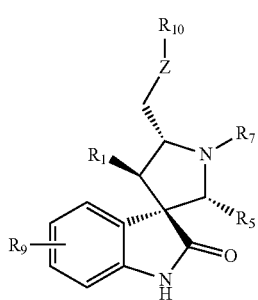

XLIV

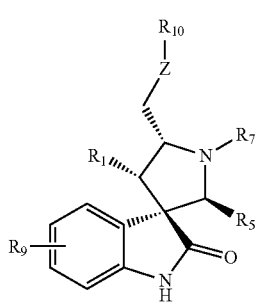

XLV

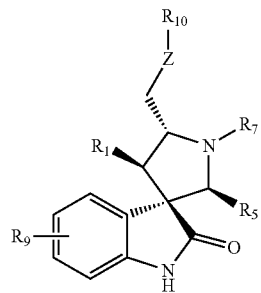

wherein Z, $R_1$, $R_5$, $R_7$, $R_9$, and $R_{10}$ are as defined above.

In a further embodiment, the compounds of Formula I have Formula XLVI:

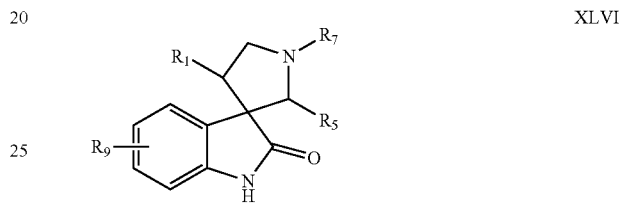

XLVI wherein $R_1$, $R_5$, $R_7$, and $R_9$ are as defined above.

In another embodiment, the compounds of Formula I have Formula XLVII:

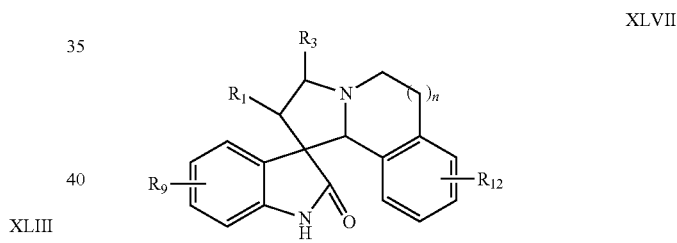

XLVII wherein:
$R_1$, $R_3$, $R_9$, and $R_9$ are as defined above;
$R_{12}$ is one to four groups independently selected from H, F, Cl, Br, I, OH, $NO_2$, alkyl, cycloalkyl, alkenyl, cycloalkenyl, alkynyl, aryl, heterocyclic, OR', $CO_2R'$, OCOR', CONR'R", NR"COR', NR'$SO_2$R", $SO_2$NR'R", (C=NR')NR"R''', or NR'R"; and
n is 0, 1, or 2.

In another embodiment, the compounds of Formula I have Formula XLVIII:

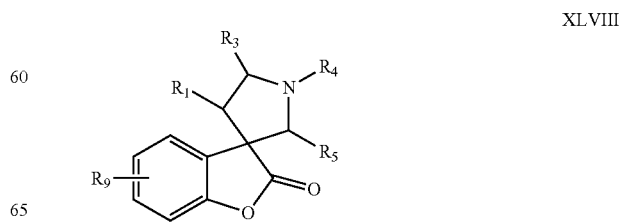

XLVIII wherein:
$R_1$, $R_3$, $R_4$, $R_5$ and $R_9$ are as defined above;
In a further embodiment, the compounds of Formula I have one of Formulae XLIX-LXIV:
XLIX
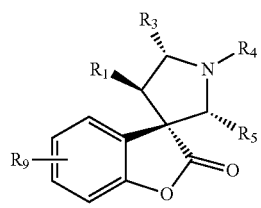
L
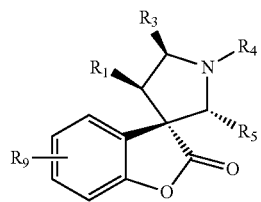
LI
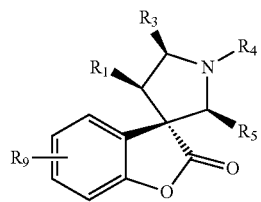
LII
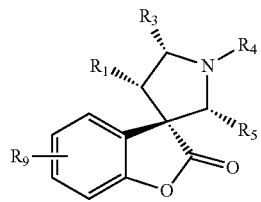
LIII
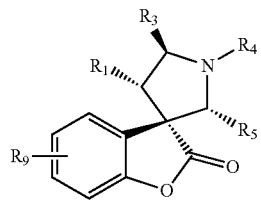
LIV
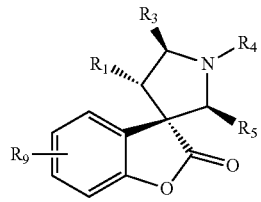
LV
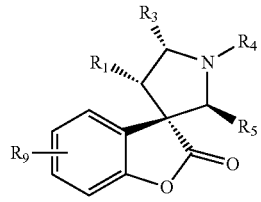
-continued
LVI
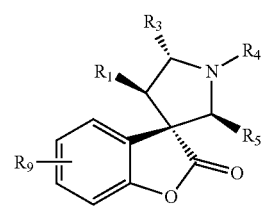
LVII
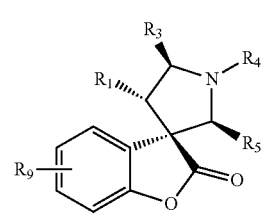
LVIII
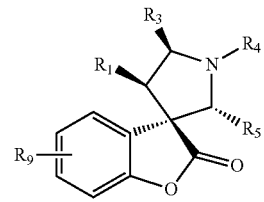
LIX
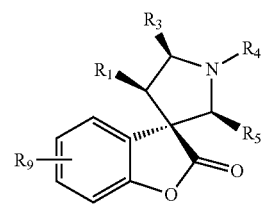
LX
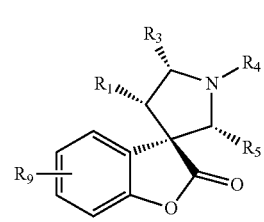
LXI
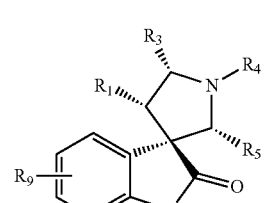
LXII
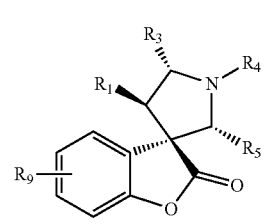

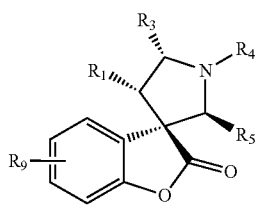

LXIII

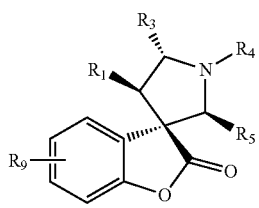

LXIV wherein:

$R_1$, $R_3$, $R_4$, $R_5$ and $R_9$ are as defined above.

In a further embodiment, the compounds of Formula I have one of Formulae LXV:

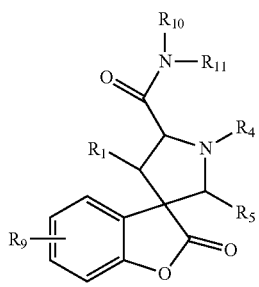

LXV wherein:

$R_1$, $R_4$, $R_5$, $R_9$, $R_{10}$, and $R_{11}$ are as defined above.

In a further embodiment, the compounds of Formula I have one of Formulae LXVI and LXVII:

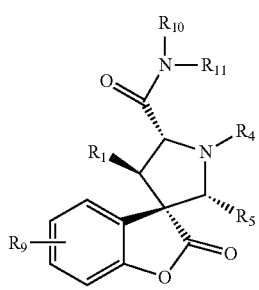

LXVI

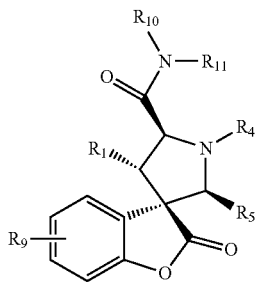

LXVII wherein:

$R_1$, $R_4$, $R_5$, $R_9$, $R_{10}$, and $R_{11}$ are as defined above.

In a further embodiment, the compounds of Formula I have one of Formulae LXVIII and LXVIX:

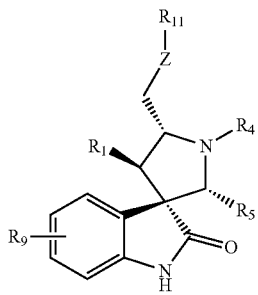

LXVIII

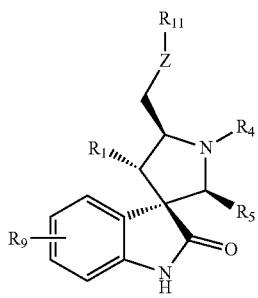

LXIX wherein:

$R_1$, $R_4$, $R_5$, $R_9$, $R_{11}$, and Z are as defined above.

Useful alkyl groups include straight-chained or branched $C_{1-18}$ alkyl groups, especially methyl, ethyl, propyl, isopropyl, t-butyl, sec-butyl, 3-pentyl, adamantyl, norbornyl, and 3-hexyl groups.

Useful alkenyl groups include straight-chained or branched $C_{2-18}$ alkyl groups, especially ethenyl, propenyl, isopropenyl, butenyl, isobutenyl, and hexenyl.

Useful alkynyl groups are $C_{2-18}$ alkynyl groups, especially ethynyl, propynyl, butynyl, and 2-butynyl groups Useful cycloalkyl groups are $C_{3-8}$ cycloalkyl. Typical cycloalkyl groups include cyclopropyl, cyclobutyl, cyclopentyl, cyclohexyl and cycloheptyl.

Useful aryl groups include $C_{6-14}$ aryl, especially phenyl, naphthyl, phenanthrenyl, anthracenyl, indenyl, azulenyl, biphenyl, biphenylenyl, and fluorenyl groups.

Useful heteroaryl groups include thienyl, benzo[b]thienyl, naphtho[2,3-b]thienyl, thianthrenyl, furyl, pyranyl, isobenzofuranyl, chromenyl, xanthenyl, phenoxanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide, pyrimidinyl N-oxide, and the like.

Useful heterocyclic groups include tetrahydrofuranyl, pyranyl, piperidinyl, piperizinyl, pyrrolidinyl, imidazolidinyl, imidazolinyl, indolinyl, is oindolinyl, quinuclidinyl, morpholinyl, isochromanyl, chromanyl, pyrazolidinyl, pyrazolinyl, tetronoyl, tetramoyl, or tetrahydroisoquinolinyl groups, as well as heterocyclic groups fused with a heteroaryl ring, e.g., optionally substituted 5,6-dihydro-8H-[1,2,4]triazolo[4,3-A]pyrazinyl.

Optional substituents include one or more alkyl; halo; haloalkyl; cycloalkyl; aryl optionally substituted with one or more lower alkyl, lower alkoxy, methylenedioxy, halo, haloalkyl, aminosulfonyl, aryl, or heteroaryl groups; aryloxy optionally substituted with one or more lower alkyl, lower alkoxy, methylenedioxy, halo, haloalkyl, aminosulfonyl, aryl, or heteroaryl groups; aralkyl; heteroaryl optionally substituted with one or more lower alkyl, lower alkoxy, methylenedioxy, halo, haloalkyl, aminosulfonyl, aryl, or heteroaryl groups; heteroaryloxy optionally substituted with one or more lower alkyl, lower alkoxy, methylenedioxy, halo, haloalkyl, aminosulfonyl, aryl, or heteroaryl groups; alkoxy; alkylthio; arylthio; amido; amino; aminoalkyl, alkylamino, acyloxy; arylacyloxy optionally substituted with one or more lower alkyl, lower alkoxy, methylenedioxy, halo, haloalkyl, aminosulfonyl, aryl, or heteroaryl groups; diphenylphosphinyloxy optionally substituted with one or more lower alkyl, lower alkoxy, methylenedioxy, halo, haloalkyl, aminosulfonyl, aryl, or heteroaryl groups; heterocyclo optionally substituted with one or more lower alkyl, lower alkoxy, methylenedioxy, halo, haloalkyl, aminosulfonyl, aryl, heteroaryl, amino acid substituted sulfonyl, or amino acid derivative substituted sulfonyl groups; heterocycloacyl optionally substituted with one or more lower alkyl, lower alkoxy, methylenedioxy, halo, haloalkyl, aminosulfonyl, aryl, or heteroaryl groups; heterocycloalkoxy optionally substituted with one or more lower alkyl, lower alkoxy, methylenedioxy, halo, haloalkyl, aminosulfonyl, aryl, or heteroaryl groups; partially unsaturated heterocycloalkyl optionally substituted with one or more lower alkyl, lower alkoxy, methylenedioxy, halo, haloalkyl, aminosulfonyl, aryl, or heteroaryl groups; or partially unsaturated heterocycloalkyloxy optionally substituted with one or more lower alkyl, lower alkoxy, methylenedioxy, halo, haloalkyl, aminosulfonyl, aryl, or heteroaryl groups.

Certain of the compounds of the present invention may exist as stereoisomers including optical isomers. The invention includes all stereoisomers, both as pure individual stereoisomer preparations and enriched preparations of each, and both the racemic mixtures of such stereoisomers as well as the individual enantiomers that may be separated according to methods that are well known to those of skill in the art.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reagents and agents in the syntheses shown below.

Compounds have the general structure of formula X are synthesized by using a asymmetric 1,3-dipolar cycloaddition as the key step (Scheme 1).

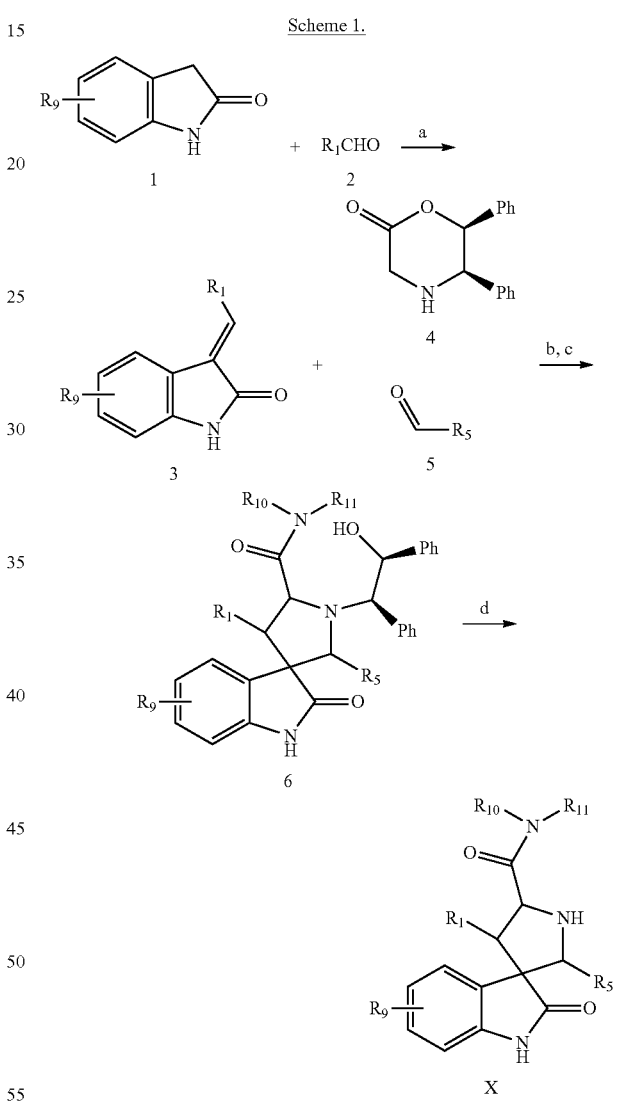

Reagents and conditions: a) $CH_2Cl_2$—$CH_3CN$, KF—$Al_2O_3$, microwave, or methanol, piperidine reflux; b) 4 Å molecular sieves, toluene, 70° C.; c) amine, r.t.; d) $Pb(OAc)_4$, $CH_2Cl_2$-MeOH (1:1), 0° C., or ammonium cerium (IV) nitrate (CAN), $CH_3CN$, $K_2CO_3$, r.t.

Compounds having Formula XXIX are prepared by the procedure shown in Scheme 2.

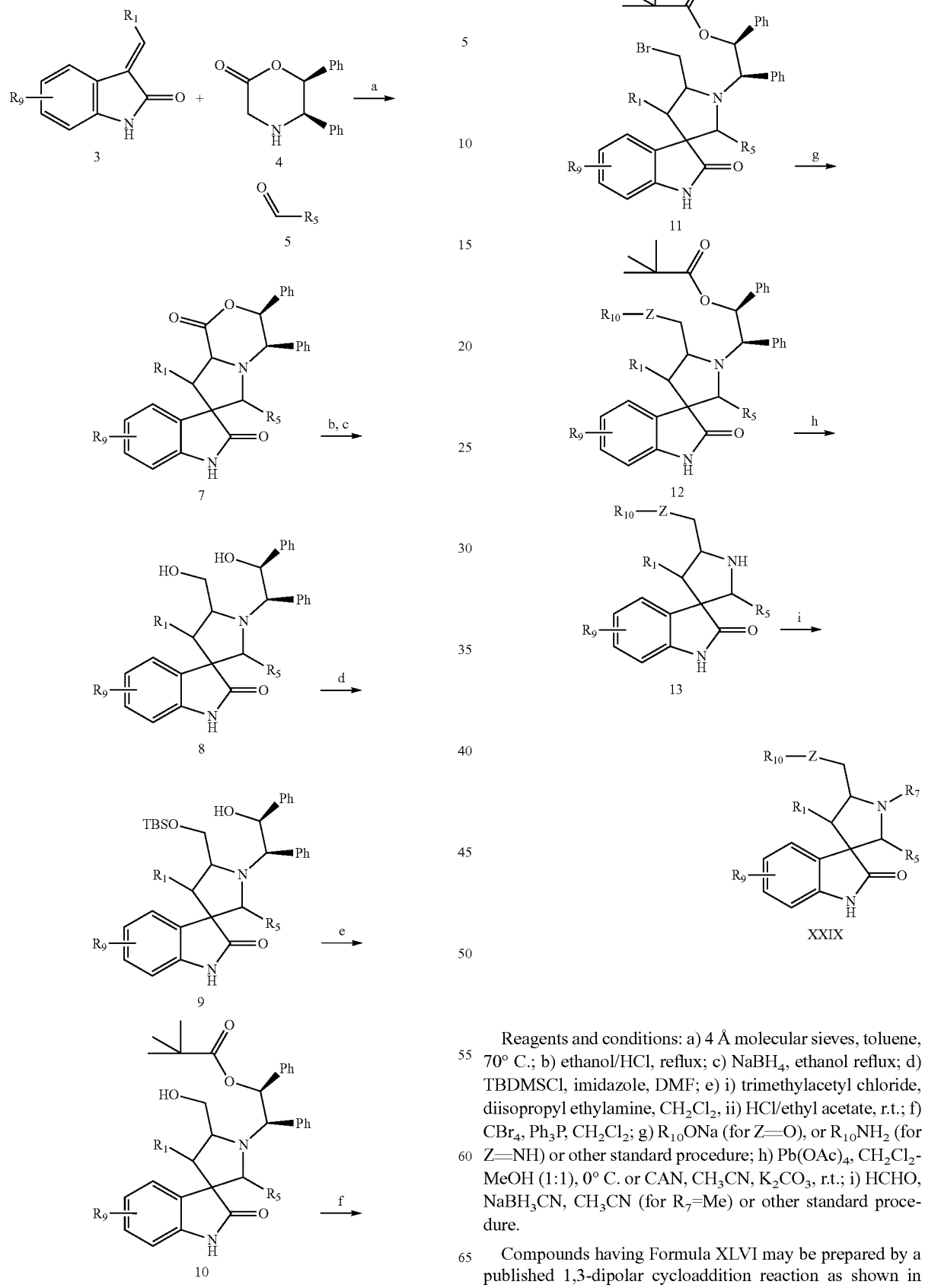

Reagents and conditions: a) 4 Å molecular sieves, toluene, 70° C.; b) ethanol/HCl, reflux; c) NaBH$_4$, ethanol reflux; d) TBDMSCl, imidazole, DMF; e) i) trimethylacetyl chloride, diisopropyl ethylamine, CH$_2$Cl$_2$, ii) HCl/ethyl acetate, r.t.; f) CBr$_4$, Ph$_3$P, CH$_2$Cl$_2$; g) R$_{10}$ONa (for Z=O), or R$_{10}$NH$_2$ (for Z=NH) or other standard procedure; h) Pb(OAc)$_4$, CH$_2$Cl$_2$-MeOH (1:1), 0° C. or CAN, CH$_3$CN, K$_2$CO$_3$, r.t.; i) HCHO, NaBH$_3$CN, CH$_3$CN (for R$_7$=Me) or other standard procedure.

Compounds having Formula XLVI may be prepared by a published 1,3-dipolar cycloaddition reaction as shown in Scheme 3 (Fejes et al., *Tetrahedron* 57:1129 (2000)).

Scheme 3.

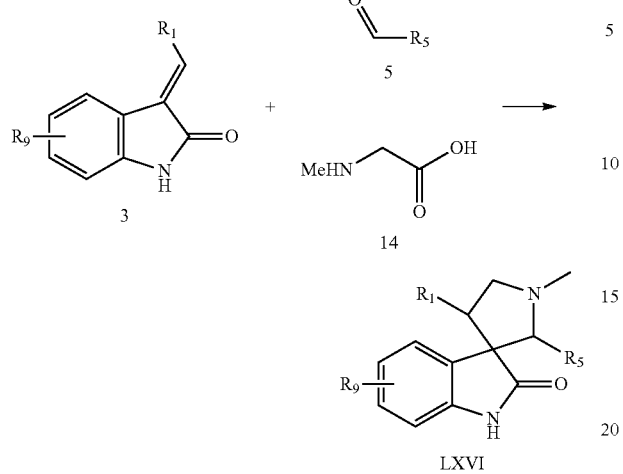

Compounds having Formula XLVII may be prepared by another published 1,3-dipolar cycloaddition reaction as shown in Scheme 4 (Fejes et al., *Tetrahedron* 57:1129 (2000)).

Scheme 4.

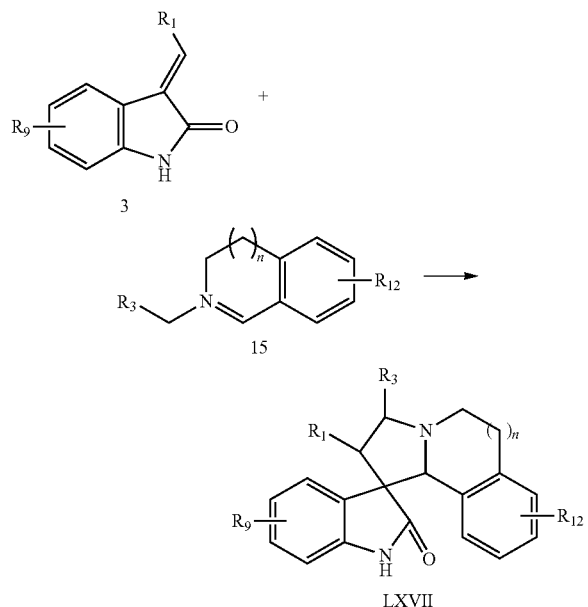

Compounds having Formula LXV are prepared by a similar method as the preparation of Formula X (Scheme 5).

Scheme 5.

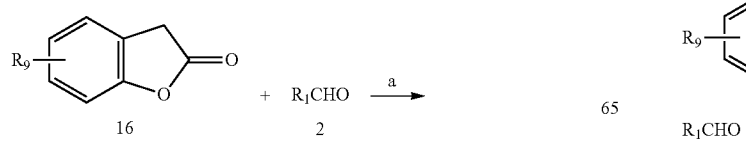

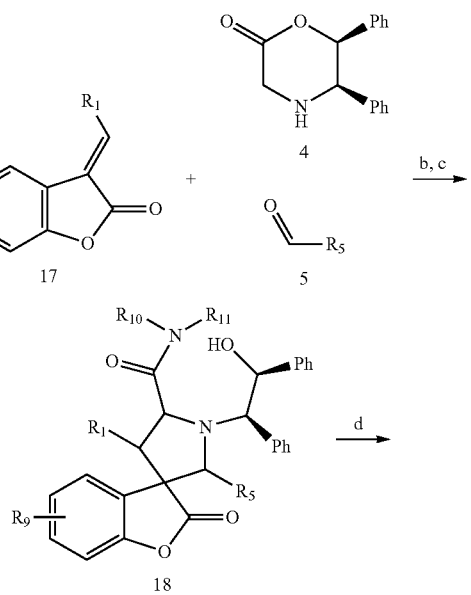

Reagents and conditions: a) $CH_2Cl_2$—$CH_3CN$, $KF$—$Al_2O_3$, microwave, or methanol, piperidine reflux; b) 4 Å molecular sieves, toluene, 70° C.; c) amine, r.t.; d) $Pb(OAc)_4$, $CH_2Cl_2$-MeOH (1:1), 0° C., or ammonium cerium (IV) nitrate (CAN), $CH_3CN$, $K_2CO_3$, r.t.

One aspect of the invention related to methods of preparing MDM2 inhibitor compounds. In one embodiment, the invention relates to a method of preparing a compound having formula X, comprising a) condensing a compound of Formula 1 with a compound of Formula 2, e.g., in a solvent or a mixture of solvents (e.g., $CH_2Cl_2$ and $CH_3CN$) under microwave in the presence of a catalyst (e.g., $KF$—$Al_2O_3$) or in the presence of a base in a suitable solvent to form a compound of Formula 3;

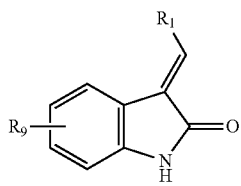

3 b) condensing the compound of Formula 3 with a compound of Formula 4 and a compound of Formula 5, e.g., in a non-polar solvent (e.g., toluene) in the presence of a dehydrating agent (e.g., 4 Å molecular sieve) at elevated temperature (e.g., about 70° C.) to form a compound of Formula 6; and

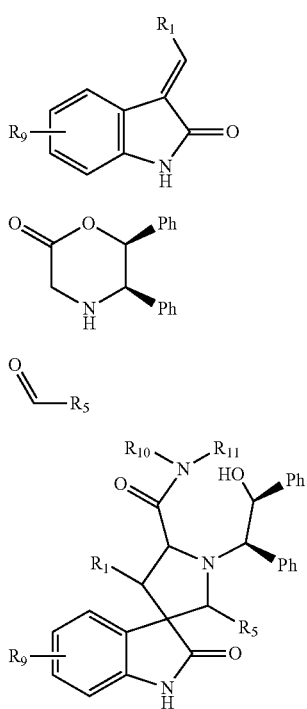

3

4

5

6 c) treating the compound of Formula 6 with an oxidizing agent (e.g., Pb(OAc)$_4$, Ammonium cerium nitrate) in a solvent or mixture of solvents (e.g., CH$_2$Cl$_2$ and MeOH, CH$_3$CN) at a suitable temperature (e.g., about 0° C. or room temperature) to form a compound of Formula X;

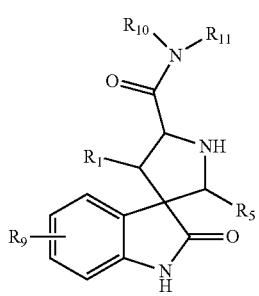

X wherein:

$R_1$, and $R_5$ are independently H or optionally substituted alkyl, cycloalkyl, alkenyl, cycloalkenyl, alkynyl, aryl, heterocyclic, CO$_2$R', OCOR', CONR'R", NR"COR', NR'SO$_2$R", SO$_2$NR'R", (C=NR')NR"R''', or NR'R";

$R_9$ is one to four groups independently selected from H, F, Cl, Br, I, OH, NO$_2$, alkyl, cycloalkyl, alkenyl, cycloalkenyl, alkynyl, aryl, heterocyclic, OR', CO$_2$R', OCOR', CONR'R", NR"COR', NR'SO$_2$R", SO$_2$NR'R", (C=NR')NR"R''', or NR'R";

$R_{10}$ and $R_{11}$ are independently H, OH or optionally substituted alkyl, cycloalkyl, alkenyl, cycloalkenyl, alkynyl, aryl, heterocyclic, (CH$_2$)$_n$—R', (CH$_2$)$_n$—NR'R", (CH$_2$)$_n$—NR'COR', (CH$_2$)$_n$—NR'SO$_2$R", (CH$_2$)$_n$—NR'(C=NR") NR''', (CH$_2$)$_n$—COOH, (CH$_2$)$_n$—COOR', (CH$_2$)$_n$—CONR'R", (CH$_2$)$_n$—OR', (CH$_2$)$_n$—SR', (CH$_2$)$_n$—COR', (CH$_2$)$_n$—SO$_3$H, (CH$_2$)$_n$—SONR'R", (CH$_2$)$_n$—SO$_2$NR'R", (CH$_2$CH$_2$O)$_n$—(CH$_2$)$_m$—OH, (CH$_2$CH$_2$O)$_n$—(CH$_2$)$_m$—OR', (CH$_2$CH$_2$O)$_n$—(CH$_2$)$_m$—COOR', (CH$_2$CH$_2$O)$_n$—(CH$_2$)$_m$—CONR'R", (CH$_2$CH$_2$O)$_n$—(CH$_2$)$_m$—NR'R", (CH$_2$CH$_2$O)$_n$—(CH$_2$)$_m$—NR'COR', (CH$_2$CH$_2$O)$_n$—(CH$_2$)$_m$—NR'(C=NR")NR''', (CH$_2$CH$_2$O)$_n$—(CH$_2$)$_m$—NR'SO$_2$R", (CH$_2$)$_n$—(CH$_2$CH$_2$O)$_m$—(CH$_2$)$_m$—OH, (CH$_2$)$_p$—(CH$_2$CH$_2$O)$_n$—(CH$_2$)$_m$—OR', (CH$_2$)$_p$—(CH$_2$CH$_2$O)$_n$—(CH$_2$)$_m$—COOR', (CH$_2$)$_p$—(CH$_2$CH$_2$O)$_n$—(CH$_2$)$_m$—CONR'R", (CH$_2$)$_p$—(CH$_2$CH$_2$O)$_n$—(CH$_2$)$_m$—NR'R", (CH$_2$)$_p$—(CH$_2$CH$_2$O)$_n$—(CH$_2$)$_m$—NR'COR', (CH$_2$)$_p$—(CH$_2$CH$_2$O)$_n$—(CH$_2$)$_m$—NR'(C=NR")NR''', (CH$_2$)$_p$—(CH$_2$CH$_2$O)$_n$—(CH$_2$)$_m$—NR'SO$_2$R", —CO—R', —SOR', or —SO$_2$R';

n, m, and p are each independently 1-6; and each R', R" and R''' is independently H or optionally substituted alkyl, cycloalkyl, alkenyl, cycloalkenyl, alkynyl, aryl, or heterocyclic; or R' and R", or R" and R''', form a ring.

In another embodiment, the invention relates to a method of preparing a compound having formula LXV, comprising a) condensing a compound of Formula 16 with a compound of Formula 2, e.g., in a solvent or a mixture of solvents (e.g., CH$_2$Cl$_2$ and CH$_3$CN) under microwave in the presence of a catalyst (e.g., KF—Al$_2$O$_3$) or in the presence of a base in a suitable solvent to form a compound of Formula 17;

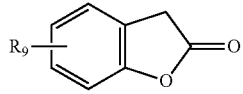

16

R$_1$CHO

2

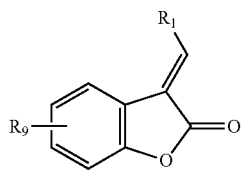

17 b) condensing the compound of Formula 17 with a compound of Formula 4 and a compound of Formula 5, e.g., in a non-polar solvent (e.g., toluene) in the presence of a dehydrating agent (e.g., 4 Å molecular sieve) at elevated temperature (e.g., about 70° C.) to form a compound of Formula 18; and

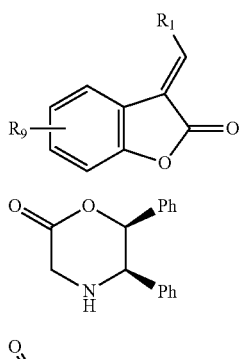

17

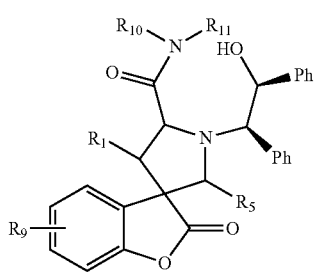

4

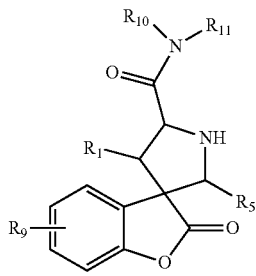

5

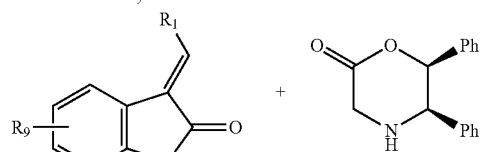

18 c) treating the compound of Formula 18 with an oxidizing agent (e.g., Pb(OAc)₄, Ammonium cerium nitrate) in a solvent or mixture of solvents (e.g., CH₂Cl₂ and MeOH, CH₃CN) at a suitable temperature (e.g., about 0° C. or room temperature) to form a compound of Formula LXV;

LXV wherein:
$R_1$, $R_5$, $R_9$, $R_{10}$ and $R_{11}$ are as defined above.

In another embodiment, the invention relates to a method of preparing a compound having formula XXIX, comprising
a) condensing a compound of Formula 3 with a compound of Formula 4 and a compound of Formula 5, e.g., in a non-polar solvent (e.g., toluene) in the presence of a dehydrating agent (e.g., 4 Å molecular sieve) or by azeotropic distillation at elevated temperature (e.g., about 70° C.) to form a compound of Formula 7;

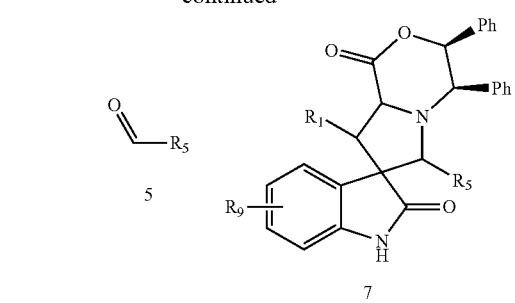

3    4

-continued

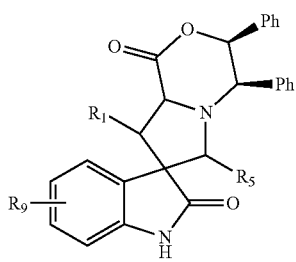

7 b) heating the compound of Formula 7 in the presence of an acid (e.g., HCl) and then adding a reducing agent (e.g., NaBH₄) to form a compound of Formula 8;

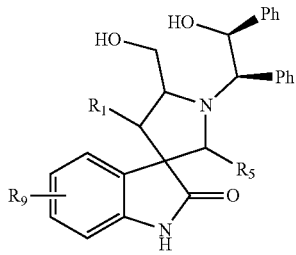

7

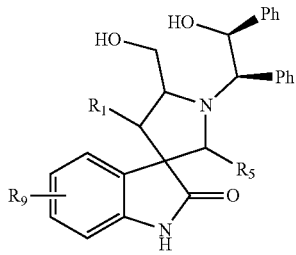

8 c) condensing the compound of Formula 8 with a blocking agent (e.g., a trialkyl silyl halide such as TBDMSCl) in a polar solvent (e.g., DMF) followed by trimethylacetyl chloride or other protective agents in a solvent or a mixture of solvents (e.g., diisopropyl ethylamine, CH₂Cl₂) and then acid (e.g., HCl) to form a compound of Formula 10;

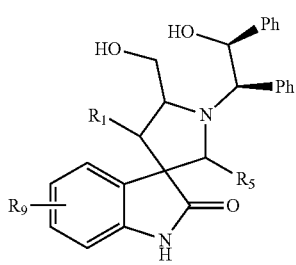

8

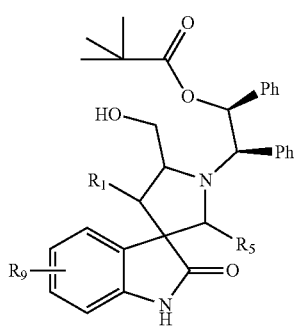

10 d) treating the compound of Formula 10 with a halogenating agent (e.g., CBr$_4$ and Ph$_3$P) in a solvent (e.g., CH$_2$CL$_2$) to form a halo compound of Formula 11;

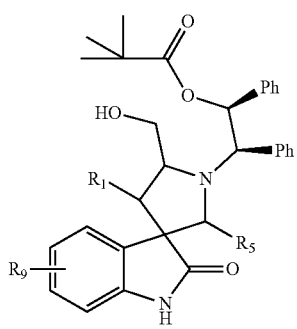

10

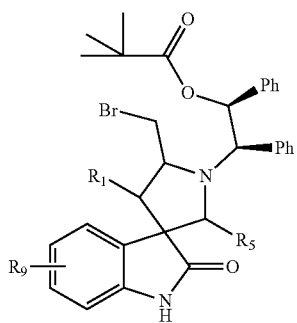

11 e) displacing the halo group of the compound of Formula 11 with R$_{10}$ONa or R$_{10}$NH$_2$ to form a compound of Formula 12;

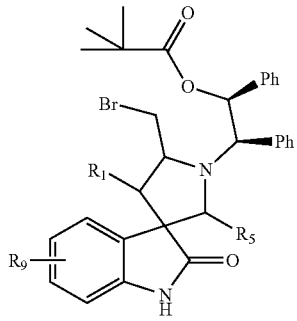

11

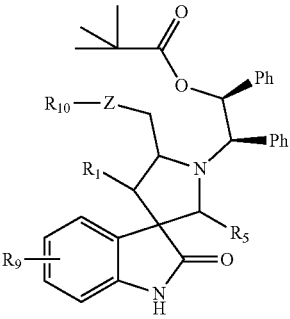

12 f) treating the compound of Formula 12 with an oxidizing agent (e.g., Pb(OAc)$_4$, or ammonium cerium nitrate) in a solvent or mixture of solvents (e.g., CH$_2$Cl$_2$ and MeOH or CH$_3$CN) at a suitable temperature (e.g., about 0° C. to room temperature) to form a compound of Formula 13; and

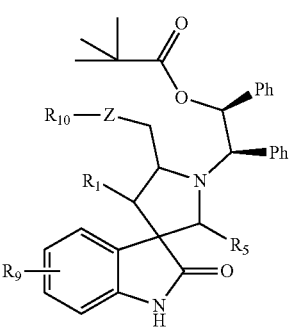

12

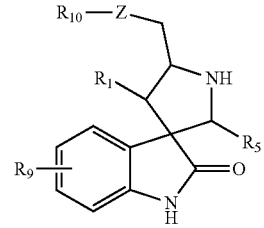

13 g) alkylating the compound of Formula 13 with an alkylating agent (e.g., HCHO, NaBH$_3$CN, and CH$_3$CN) to form a compound of Formula XXIX;

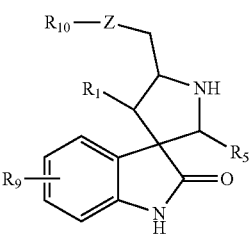

13

XXIX

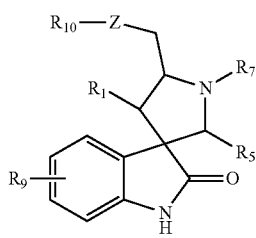

wherein $R_1$, $R_5$, $R_7$, $R_9$, $R_{10}$ and Z are as defined above.

An important aspect of the present invention is that compounds of Formula I induce cell cycle arrest and/or apoptosis and also potentiate the induction of cell cycle arrest and/or apoptosis either alone or in response to additional apoptosis induction signals. Therefore, it is contemplated that these compounds sensitize cells to induction of cell cycle arrest and/or apoptosis, including cells that are resistant to such inducing stimuli. The inhibitors of the interaction between p53 or p53-related proteins and MDM2 or MDM2-related proteins of the present invention can be used to induce apoptosis in any disorder that can be treated, ameliorated, or prevented by the induction of apoptosis. In one embodiment, the inhibitors can be used to induce apoptosis in cells comprising functional p53 or p53-related proteins.

In another embodiment, the invention pertains to modulating an apoptosis associated state which is associated with one or more apoptosis-modulating agents. Examples of apoptosis-modulating agents include, but are not limited to, Fas/CD95, TRAMP, TNF RI, DR1, DR2, DR3, DR4, DR5, DR6, FADD, RIP, TNFα, Fas ligand, TRAIL, antibodies to TRAIL-R1 or TRAIL-R2, Bcl-2, p53, BAX, BAD, Aid, CAD, PI3 kinase, PP1, and caspase proteins. Other agents involved in the initiation, decision and degradation phase of apoptosis are also included. Examples of apoptosis-modulating agents include agents, the activity, presence, or change in concentration of which, can modulate apoptosis in a subject. Preferred apoptosis-modulating agents are inducers of apoptosis, such as TNF or a TNF-related ligand, particularly a TRAMP ligand, a Fas/CD95 ligand, a TNFR-1 ligand, or TRAIL.

In some embodiments, the compositions and methods of the present invention are used to treat diseased cells, tissues, organs, or pathological conditions and/or disease states in an animal (e.g., a mammalian subject including, but not limited to, humans and veterinary animals). In this regard, various diseases and pathologies are amenable to treatment or prophylaxis using the present methods and compositions. A non-limiting exemplary list of these diseases and conditions includes, but is not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the cancer cells being treated are resistant to anticancer agents.

In some embodiments, infections suitable for treatment with the compositions and methods of the present invention include, but are not limited to, infections caused by viruses, bacteria, fungi, mycoplasma, prions, and the like.

Some embodiments of the present invention provide methods for administering an effective amount of a compound of Formula I and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies).

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-κB modulators; anti-CDK compounds; HDAC inhibitors; and the like. Numerous other examples of chemotherapeutic compounds and anticancer therapies suitable for co-administration with the disclosed compounds are known to those skilled in the art.

In preferred embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); antiandrogens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of Formula I and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyl-triazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N'',-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus* Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |

| | | |
|---|---|---|
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-, (SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by Streptomyces parvullus, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |

-continued

| | | |
|---|---|---|
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$, Azgly$^{10}$]LHRH; pyro-Glu-His-Trp-Ser-Tyr-D-Ser(But)-Leu-Arg-Pro-Azgly-NH2 acetate [C$_{59}$H$_{84}$N$_{18}$O$_{14}$•(C$_2$H$_4$O$_2$)$_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperidinopiperidino)carbonyloxy]-1H-pyrano[3',4': 6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride C$_{11}$H$_{12}$N$_2$S•HCl) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |

| | | |
|---|---|---|
| Megestrol acetate<br>17α(acetyloxy)-6-methylpregna-4,6-diene-3,20-dione | Megace | Bristol-Myers Squibb |
| Melphalan, L-PAM<br>(4-[bis(2-chloroethyl) amino]-L-phenylalanine) | Alkeran | GlaxoSmithKline |
| Mercaptopurine, 6-MP<br>(1,7-dihydro-6H-purine-6-thione monohydrate) | Purinethol | GlaxoSmithKline |
| Mesna<br>(sodium 2-mercaptoethane sulfonate) | Mesnex | Asta Medica |
| Methotrexate<br>(N-[4-[[(2,4-diamino-6-pteridinyl)methyl]methylamino]benzoyl]-L-glutamic acid) | Methotrexate | Lederle Laboratories |
| Methoxsalen<br>(9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane<br>(1,1-dichloro-2-(o-chlorophenyl)-2-(p-chlorophenyl) ethane) | Lysodren | Bristol-Myers Squibb |
| Mitoxantrone<br>(1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin<br>(IL-11) | Neumega | Genetics Institute, Inc., Alexandria, VA |
| Oxaliplatin<br>(cis-[(1R,2R)-1,2-cyclohexanediamine-N,N'] [oxalato(2-)-O,O'] platinum) | Eloxatin | Sanofi Synthelabo, Inc., NY, NY |
| Paclitaxel<br>(5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate<br>(phosphonic acid (3-amino-1-hydroxypropylidene) bis-, disodium salt, pentahydrate, (APD)) | Aredia | Novartis |
| Pegademase<br>((monomethoxypolyethylene glycol succinimidyl) 11-17-adenosine deaminase) | Adagen<br>(Pegademase Bovine) | Enzon Pharmaceuticals, Inc., Bridgewater, NJ |
| Pegaspargase<br>(monomethoxypolyethylene glycol succinimidyl L-asparaginase) | Oncaspar | Enzon |
| Pegfilgrastim<br>(covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin<br>(antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine<br>(N-isopropyl-μ-(2-methylhydrazino)-p-toluamide monohydrochloride) | Matulane | Sigma Tau Pharmaceuticals, Inc., Gaithersburg, MD |
| Quinacrine<br>(6-chloro-9-(1-methyl-4-diethyl-amine) butylamino-2-methoxyacridine) | Atabrine | Abbott Labs |
| Rasburicase<br>(recombinant peptide) | Elitek | Sanofi-Synthelabo, Inc., |
| Rituximab<br>(recombinant anti-CD20 antibody) | Rituxan | Genentech, Inc., South San Francisco, CA |
| Sargramostim<br>(recombinant peptide) | Prokine | Immunex Corp |
| Streptozocin<br>(streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc<br>($Mg_3Si_4O_{10}(OH)_2$) | Sclerosol | Bryan, Corp., Woburn, MA |
| Tamoxifen<br>((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |

-continued

| | | |
|---|---|---|
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine,1,1',1"-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4': 6,7] indolizino [1,2-b] quinoline-3,14-4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity but are not currently approved by the U.S. Food and Drug Administration or other counterpart agencies or are undergoing evaluation for new uses. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of Formula I with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromo ethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. The dose of radiation is preferably fractionated for maximal target cell exposure and reduced toxicity.

The total dose of radiation administered to an animal preferably is about 0.01 Gray (Gy) to about 100 Gy. More preferably, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), preferably 1-2 Gy (e.g., 1.5-2 Gy). The daily dose of radiation should be sufficient to induce destruction of the targeted cells. If stretched over a period, radiation preferably is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. Preferably, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, a compound of Formula I and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. Preferably, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, and most preferably, from about 0.01 to about 5 mg/kg.

The unit oral dose may comprise from about 0.01 to about 1000 mg, preferably about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a preferred embodiment, the compound is present at a concentration of about 0.07-1.0 mg/ml, more preferably, about 0.1-0.5 mg/ml, most preferably, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, preferably from about 0.25 to 75 percent of active compound(s), together with the excipient.

The pharmaceutical compositions of the invention may be administered to any animal which may experience the beneficial effects of the compounds of the invention. Foremost among such animals are mammals, e.g., humans, although the invention is not intended to be so limited. Other animals include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

Example 1

Design of MDM2 Inhibitors

Since many anti-cancer drugs are either natural products or contain a core pharmacophore derived from natural products, a search was done for natural products that could provide a novel scaffold for the design of compounds capable of inhibiting the interaction between p53 and MDM2.

Computational docking studies were carried out using the GOLD program (version 2.1) with the ChemScore fitness function. The structures of ligands were constructed at SYBYL 6.9 and energy minimized by Tripos force field. The MDM2 structure was extracted from the crystal structure of MDM2 bound with p53 (PDB code: 1YCR). Hydrogens were added to the protein using SYBYL 6.9. The active site was defined to encompass all atoms within a 12 Å radius sphere, whose origin was located at the center of the Trp23 of the p53 peptide. The standard Genetic Algorithm protocol was selected for the docking. For each compound, 20 individual docking runs were conducted. The generated 20 solutions of each ligand were ranked according to the score of ChemScore. The best ranked solution of each ligand was rescored by X-Score and used in the further analysis of binding mode.

Figure 2A:
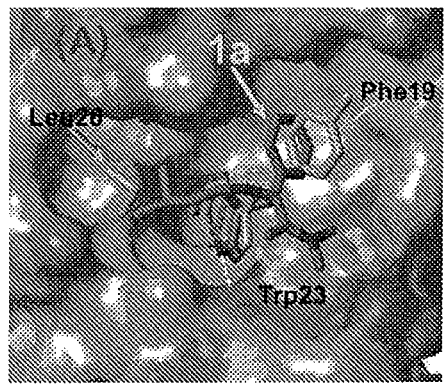
FIGS. 2A and 2B show the predicted binding model of compounds 1a and 1d to MDM2.

Spirotryprostatin A represents a class of natural alkaloids isolated from the fermentation broth of *Aspergillus fumigatus* (Usui et al., *Biochem. J.* 33:543 (1998)) (FIG. 1). Computational docking studies showed that spirotryprostatin A cannot bind in the hydrophobic cleft of MDM2, but the spiro(oxindole-3,3'-pyrrolidine) core structure may be used as a rigid scaffold for the design of a new class of inhibitors of the p53-MDM2 interaction. The oxindole unit closely mimics the Trp23 residue in both hydrogen-bond formation and hydrophobic interaction with MDM2. The pyrrolidinyl ring provides a rigid scaffold with which two hydrophobic groups can be attached to mimic Phe19 and Leu26 (FIG. 2A). A number of template compounds were modeled using different substituent groups with different configurations. Of these, compound 1a was shown to mimic p53 well in its hydrogen-bonding and key hydrophobic interactions with MDM2 (FIG. 2A). The 6-chloro substituent on the oxindole ring occupies a small hydrophobic pocket in MDM2, an interaction which has been shown to be effective in enhancing the binding affinities of p53-based peptide inhibitors of MDM2 (Garcia-Echeverria et al., *Med. Chem.* 43:3205 (2000)).

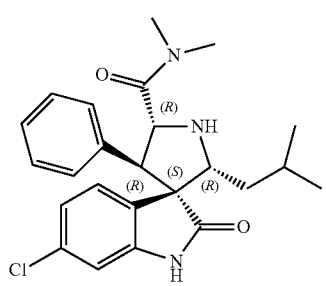

1a

Example 2

Fluorescence Polarization Binding Assay

Figure 3:
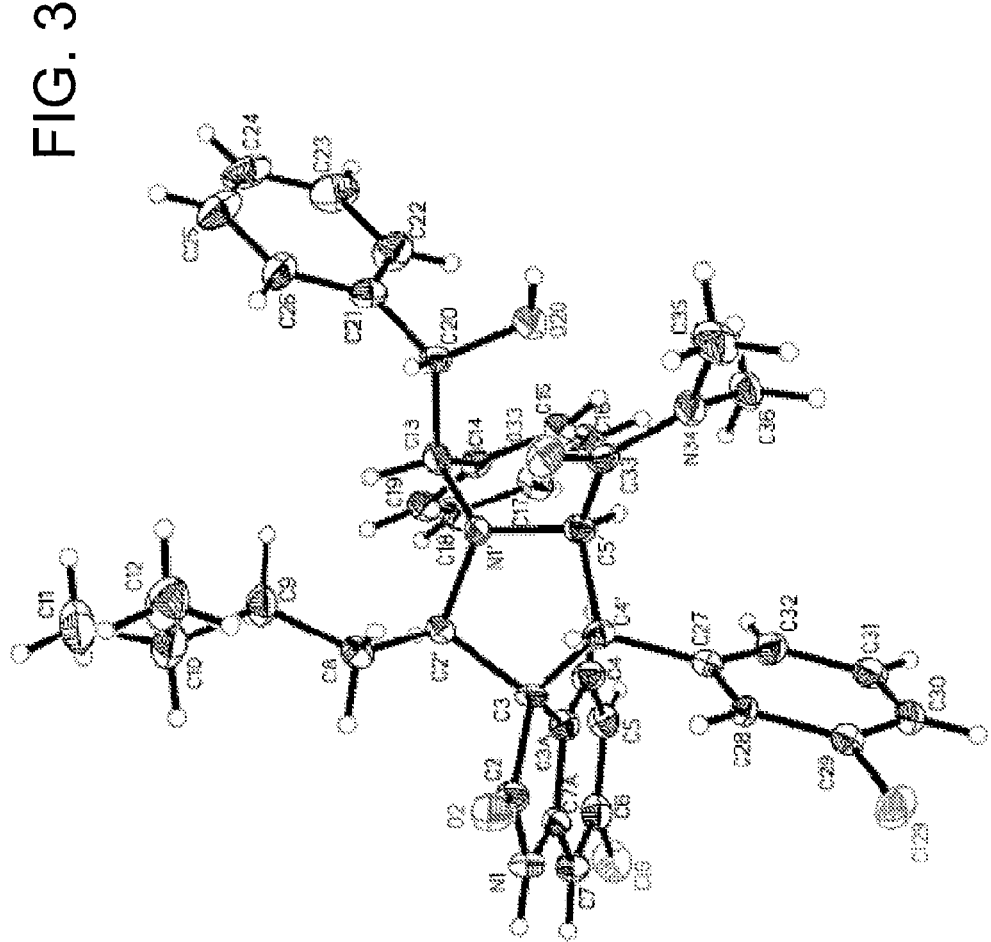
FIG. 3 shows the X-ray structure of (1"R,2"S,2'R,3'R,3S,4'R) 6-chloro-4'-(3-chloro-phenyl)-1'-(2-hydroxy-1,2-diphenyl-ethyl)-2'-(3-methyl-butyl)-2-oxo-1,2-dihydro-spiro[indole-3,3'-pyrrolidine]-5'-carboxylic acid dimethylamide.

Compound 1a was synthesized as shown in Scheme 1 using an asymmetric 1,3-dipolar reaction as the key step (Sebehar et al., *J. Am. Chem. Soc.* 122:5666 (2000)). The absolute stereochemistry of 1a and other designed analogues was determined by an X-ray crystallographic analysis of one of the key intermediates, (1"R,2"S,2'R,3'R,3S,4'R) 6-chloro-4'-(3-chloro-phenyl)-1'-(2-hydroxy-1,2-diphenyl-ethyl)-2'-(3-methyl-butyl)-2-oxo-1,2-dihydro-spiro[indole-3,3'-pyrrolidine]-5'-carboxylic acid dimethylamide (FIG. 3).

Figure 4A:
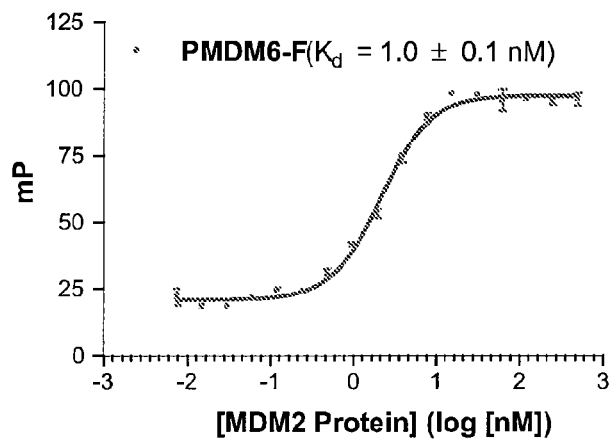
FIG. 4A shows the saturation curve of PMDM6-F binding to MDM2 protein.
Figure 4B:
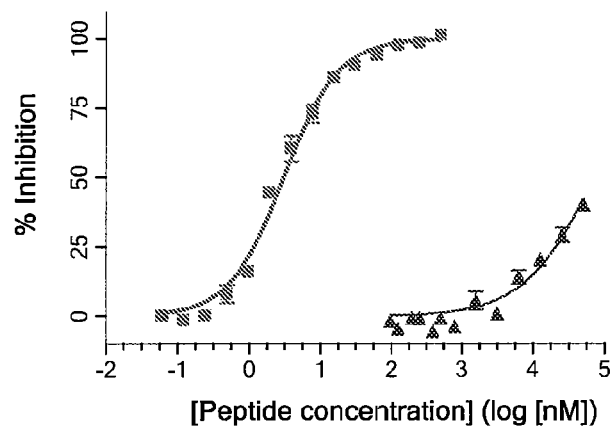
FIG. 4B shows the competitive binding curves of unlabeled fluorescent probe PMDM6 and native p53 peptide to MDM2 protein.

To determine the ability of 1a to disrupt the interaction between MDM2 and p53, a fluorescence polarization (FP)-based binding assay was established using a recombinant human MDM2 protein and a p53-based peptide (Garcia-Echeverria et al., *J Med Chem* 43:3205 (2000)) labeled with a fluorescence tag. The fluorescent-probe, termed PMDM6-F, had the sequence (5-Fam-βAla-βAla-Phe-Met-Aib-pTyr-(6-Cl-1-Trp)-Glu-Ac3c-Leu-Asn-$NH_2$) (SEQ ID NO:1), wherein Fam is carboxyfluorescein, Aib is β-aminoisobutyric acid, and Ac3c is 1-aminocyclopropane-1-carboxylic acid. The $K_d$ value of the binding of this designed probe to MDM2 protein was determined to be 0.001 μM (1 nM±0.09), showing that this peptide binds to the surface pocket of the MDM2 protein with very high affinity (FIG. 4A). Assay specificity was confirmed by competitive displacement of PMDM6-F binding to MDM2 protein by an unlabeled peptide with the identical sequence. It was determined that the corresponding unlabeled PMDM6 peptide ($K_i$=0.7 nM±0.1) had significantly higher binding affinity than the wild-type p53 peptide (PLSQETFSDLWKLLPEN-$NH_2$) (SEQ ID NO:2) ($K_i$=6.7 μM±1.2) (FIG. 4B). The recombinant MDM2 human protein (residues 1-118) fused to His-tag at the N terminus was stable and soluble, and was used for the FP based binding assay.

The dose-dependent binding experiments were carried out with serial dilutions of the tested compounds in DMSO. A 5 μl sample of the tested samples and preincubated MDM2 protein (0.010 μM) and PMDM6-F peptide (0.001 μM) in assay buffer (100 mM potassium phosphate, pH 7.5; 100 μg/ml bovine gamma globulin; 0.02% sodium azide, purchased from Invitrogen Life Technology), were mixed in Dynex 96-well, black, round-bottom plates (Fisher Scientific) to produce a final volume of 125 μl. For each assay, the bound peptide control containing MDM2 protein and PMDM6-F (equivalent to 0% inhibition) and free peptide control containing only free PMDM6-F (equivalent to 100% inhibition) were included. The polarization values were measured after 3 hrs of incubation when the binding reached equilibrium using an ULTRA READER (Tecan U.S. Inc., Research Triangle Park, N.C.). $IC_{50}$ values, the inhibitor concentration at which 50% of bound peptide is displaced, were determined from a plot using nonlinear least-squares analysis. Curve fitting was performed using GRAPHPAD PRISM software (GraphPad Software, Inc., San Diego, Calif.).

To calculate the binding affinity constants ($K_i$) of inhibitors, the following equation developed for computing the $K_i$ values in FP-based binding assays was used:

$$K_i = [I]_{50}/([L]_{50}/K_d + [P]_0/K_d + 1)$$

in which $[I]_{50}$ denotes the concentration of the free inhibitor at 50% inhibition, $[L]_{50}$ the concentration of the free labeled ligand at 50% inhibition, $[P]_0$ the concentration of the free protein at 0% inhibition, and $K_d$ the dissociation constant of the protein-ligand complex. For accurately computing the $K_i$ values of inhibitors using the presented equation, a computational procedure was developed to compute the accurate values of all of the parameters required in the equation (Nikolovska-Coleska et al., *Anal. Biochem.* 332:261 (2004)). A web-based computer program was also developed for computing the $K_i$ values for inhibitors in FP-based binding assays based upon the same equation.

Figure 5:
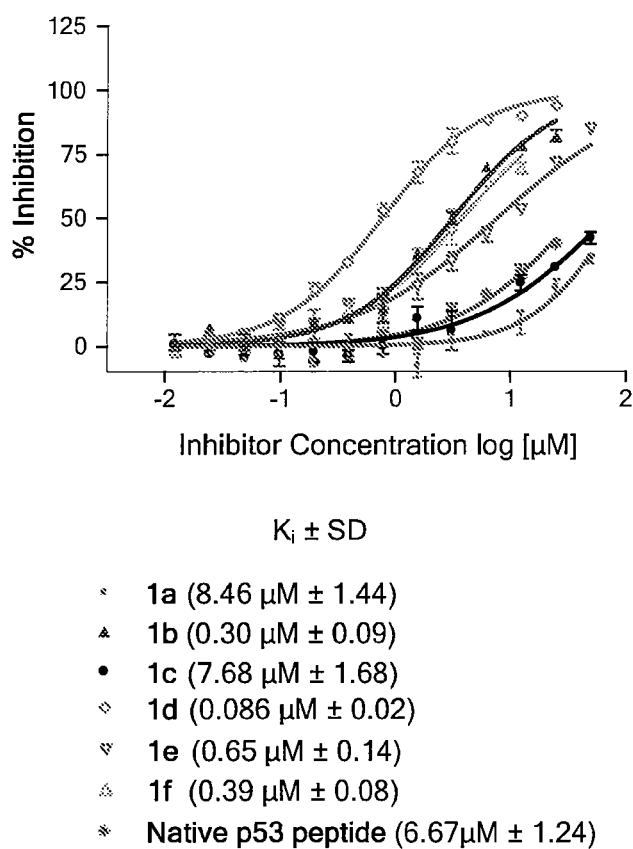
FIG. 5 shows the competitive binding curves and $K_i$ values of inhibitors of MDM2 as determined using a FP-based binding assay.

The fluorescently labeled p53-based peptide had a $K_d$ value of 1 nM with MDM2, which is consistent with its previously reported high affinity to MDM2 (Garcia-Echeverria et al., *Med. Chem.* 43:3205 (2000)). In this binding assay, a natural p53 peptide (residues 13-29), which was used as a positive control, and 1a were determined to have $K_i$ values of 6.7 μM and 8.5 μM, respectively (FIG. 5). Hence, 1a is a fairly potent inhibitor of the p53-MDM2 interaction.

Figure 2B:
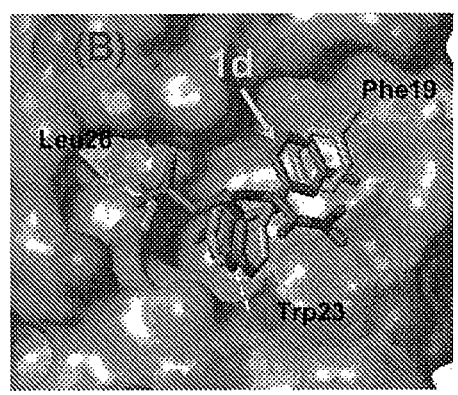

Analysis of the model of 1a bound to MDM2 (FIG. 2) suggested that 1a could be further optimized for better interaction with MDM2. For example, the phenyl ring of 1a binds to the hydrophobic binding pocket occupied by the side chain of Phe 19 but there is additional space in this pocket. Similarly, the isobutyl group of 1a fills the hydrophobic binding pocket occupied by Leu26 but a larger hydrophobic group could be accommodated. New analogues of 1a were designed in an attempt to optimize further the interactions at these two hydrophobic binding sites.

Modeling studies showed that introduction of a chlorine atom at the meta-position of the phenyl ring in 1a can exploit the additional room available at this binding site and improves the hydrophobic interaction. These studies also showed that introduction of a chlorine atom at either the para- or the ortho-position of the phenyl ring in 1a may vitiate binding to MDM2. Compound 1b with a m-Cl was synthesized and determined to have a $K_i$ value of 300 nM. It is thus 28-times more potent than 1a (FIG. 5). To further confirm the modeling prediction, the compound with a p-Cl substituent (1c) was synthesized and found to be 26-times less potent than 1b ($K_i$=7.7 nM).

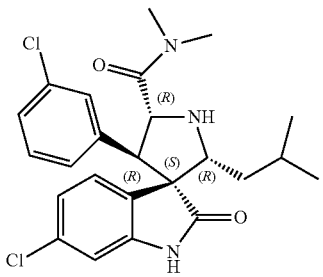

1b

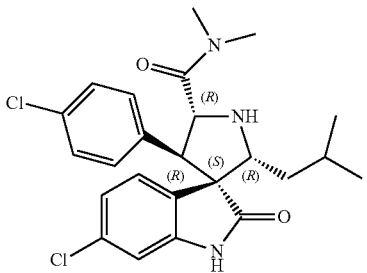

1c

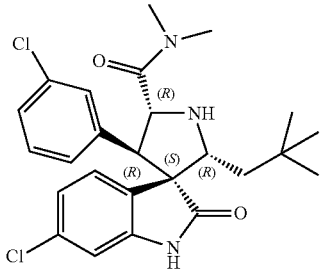

1d

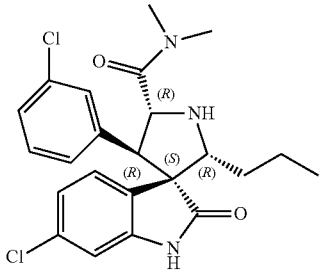

1e

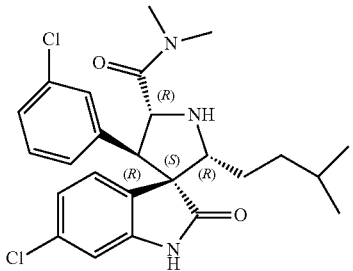

1f

As indicated above, the isobutyl group in 1a is not optimal and the hydrophobic interaction at this site was further optimized using 1b as the template. Modeling studies showed that a 2,2-dimethyl propyl group can enhance the hydrophobic interaction (FIG. 2) and the resulting compound 1d was synthesized. It was found to have a $K_i$ value of 86 nM and is thus a highly potent inhibitor of the p53-MDM2 interaction, being 78-times more potent than the natural p53 peptide.

To confirm the importance of the hydrophobic interaction at this site, compounds 1e and 1f were designed and synthesized, having a smaller and a larger hydrophobic group than 1d, respectively. Modeling studies suggested that both 1e and 1f should be less potent than 1d and in fact, FP-based binding experiments determined that 1e and 1f, with $K_i$ values of 650 and 390 nM, respectively, were substantially less potent than 1d (FIG. 5).

Example 3

Cell Growth Inhibition

One major advantage of non-peptide small-molecule inhibitors over peptide-based inhibitors is their superior cell permeability. It is predicted that potent, non-peptide inhibitors of the p53-MDM2 interaction such as 1d will be effective in inhibition of cell growth and division in cancer cells with a wild-type form of p53 through stimulation of the activity of p53. Furthermore, they are predicted to have selectivity in cancer cells with either a loss of p53 or a mutated, non-functional form of p53. To test these predictions, a cell growth assay was developed using human prostate cancer LNCaP (p53 wild-type) and PC-3 (p53 null) cell lines. The toxic effects of compounds on normal cells were also examined on a normal prostate epithelial cell line.

Cells were seeded in 96-well flat bottom cell culture plates at a density of $3-4 \times 10^3$ cells/well and incubated in the presence of compounds for 4 days. The rate of cell growth inhibition after treatment with increasing concentrations of the compounds was determined using WST-8 (2-(2-methoxy-4-nitrophenyl)-3-(4-nitrophenyl)-5-(2,4disulfophenyl)-2H-tetrazolium monosodium salt (Dojindo Molecular Technologies Inc., Gaithersburg, Md.). WST-8 was added at a final concentration of 10% to each well and the plates were incubated at 37° C. for 2-3 hrs. The absorbance of the samples was measured at 450 nm in a plate reader (Molecular Device-TECAN ULTRA). The concentration of the compounds that inhibited cell growth by 50% ($IC_{50}$) was calculated by comparing absorbance in the untreated cells and the cells treated with the compounds. The compounds induced cell growth inhibition in a dose-dependent fashion.

Figure 6:
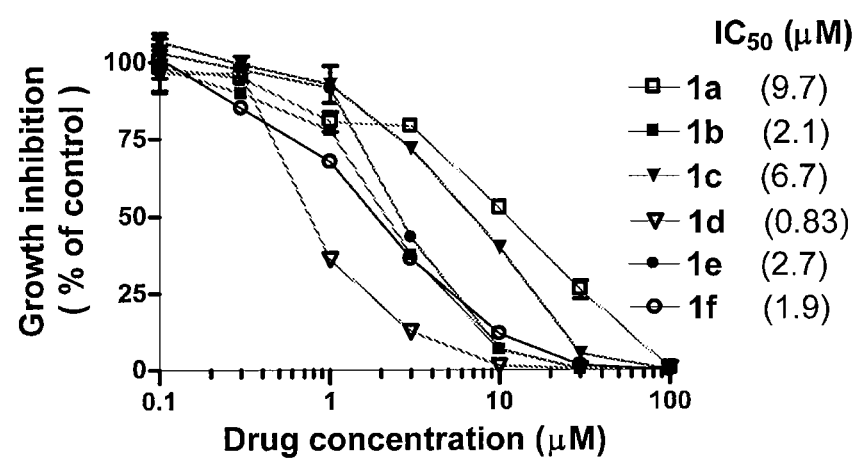
FIG. 6 shows the inhibition of cell growth in LNCaP prostate cancer cells with wild-type p53 as determined by a WST cell growth assay.
Figure 7:
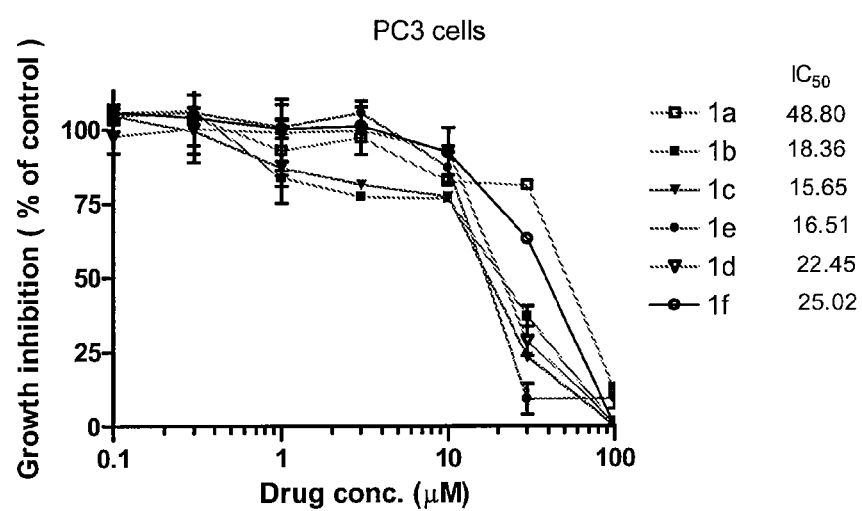
FIG. 7 shows the inhibition of cell growth in PC3 prostate cancer cells with mutant p53 as determined by a WST cell growth assay.

As predicted, compound 1d was highly effective in inhibition of cell growth in LNCaP cells comprising wild type p53, with an $IC_{50}$ value of 0.83 μM (FIG. 6). Compounds 1b, 1e and 1f also effectively inhibited cell growth with $IC_{50}$ values of 2.1, 2.7, and 1.9 μM, respectively (FIG. 6). Their activities in inhibition of cell growth in LNCaP cells correlate perfectly with their binding affinities to MDM2. Cellular selectivity was evaluated in PC-3 cells with a loss of p53. As expected, these MDM2 inhibitors were much less potent in PC-3 cells than in LNCaP cells (FIG. 7). For example, 1d, with an $IC_{50}$ value of 22.5 μM in PC-3 cells, was 27-times less active than in LNCaP cells.

Figure 8:
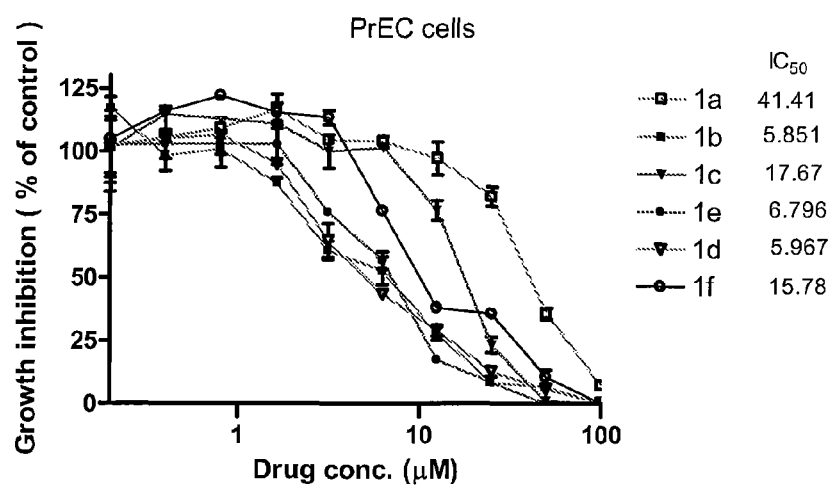
FIG. 8 shows the inhibition of cell growth in PrEC normal human prostate epithelial cells with wild-type p53 as determined by a WST cell growth assay.

Since normal cells also have wild-type p53, a potential concern in development of inhibitors of the p53-MDM2 interaction as new anti-cancer drugs is that they may be nonselective and equally active in killing normal cells as they are in killing cancer cells. Compound 1d was evaluated in normal human prostate epithelial cells (PrEC) with wild-type p53 and it was determined that 1d had an $IC_{50}$ value of 6.0 μM in PrEC cells (FIG. 8). Hence, 1d was 13-times less potent in PrEC cells than in LNCaP cells and displays a good selectivity for normal cells.

Example 4

3-E-Benzylidene-6-Chloro-1,3-Dihydro-Indol-2-One

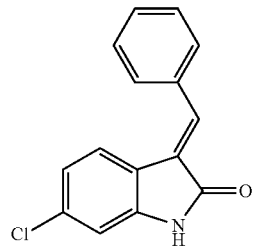 [SMILES: O=C1Nc2cc(Cl)ccc2/C1=C\c1ccccc1]

General techniques: Elemental analyses were performed by the Department of Chemistry of the University of Michigan, Ann Arbor, Mich. Where molecular formulas are given, elemental compositions were found to be within 0.3% of the theoretical values unless otherwise noted. Optical rotations were determined at 589 nm at 25° C. on a Perkin-Elmer 241 polarimeter (in $CHCl_3$). Single-crystal X-ray analysis was performed at the Naval Research Laboratory, Washington, D.C. $^1H$ NMR spectra were recorded at 300 MHz and $^{13}C$ NMR spectra were recorded at 75 MHz on a Bruker AVANCE300 spectrometer. All NMR spectra were obtained in $CDCl_3$ and results were recorded as parts per million (ppm) downfield from tetramethylsilane (TMS). The following abbreviations are used for multiplicity of NMR signals: s=singlet, d=doublet, t=triplet. q=quartet, m=multiplet, dd=double doublet, dt=double triplet, dq=double quartet, br=broad.

Method A: To a solution of 6-chloro-oxindole (1.67 g, 10.0 mmol) in 60 mL $CH_2Cl_2$:$CH_3CN$ (1:1), benzaldehyde (10.0 mmol) and KF—$Al_2O_3$ (10 g) were added. After 10 min at room temperature, the solvent was removed in vacuo, and the residues together with the flask were placed in a microwave oven and heated for 5 min (60~80 W). Extraction was carried out with 150 mL $CH_3CN$, the solid was filtered off, and the solvent was removed in vacuo to yield the crude product, which was used without further purification.

Method B: To a solution of 6-chloro-oxindole (1.67 g, 10.0 mmol) in 60 mL methanol, benzaldehyde (10.0 mmol) and piperidine (10 g) were added and the resulting mixture was refluxed for 4 hrs. The precipitate was filtered off and washed by cold methanol to yield the pure product.

$^1H$ NMR (300 MHz, $CDCl_3$) δ 7.90 (br, 1H), 7.63 (d, J=5.67 Hz, 2H), 7.55 (d, J=8.27 Hz, 1H), 7.49 (d, J=5.87 Hz, 2H), 7.39 (d, J=7.85 Hz, 2H), 6.90 (s, 1H), 6.85 (d, J=8.22 Hz, 1H), 4.66 (s, 1H).

Example 5

In a similar procedure, the following compounds were prepared.
a) 3-E-6-Chloro-3-(3-chloro-benzylidene)-1,3-dihydro-indol-2-one
  $^1H$ NMR (300 MHz, $CDCl_3$) δ 8.08 (br, 1H), 7.76 (s, 1H), 7.62~7.61 (m, 1H), 7.55~7.43 (m, 4H), 6.92 (d, J=1.52 Hz, 1H), 6.89 (dd, J=1.91, 8.18 Hz, 1H).
b) 3-E-Benzylidene-1,3-dihydro-indol-2-one
  $^1H$ NMR (300 MHz, $CDCl_3$) δ 8.32 (br, 1H), 7.87 (s, 1H), 7.77~7.66 (m, 3H), 7.75~7.43 (m, 3H), 7.24 (td, J=1.10, 7.69 Hz, 1H), 6.93~6.87 (m, 2H).

c) 3-E-6-Chloro-3-(4-chloro-benzylidene)-1,3-dihydro-indol-2-one
d) 3-E-Benzylidene-6-bromo-1,3-dihydro-indol-2-one
e) 3-E-Benzylidene-6-fluoro-1,3-dihydro-indol-2-one
f) 3-E-Benzylidene-6-trifluoromethyl-1,3-dihydro-indol-2-one
g) 3-E-6-Chloro-3-(4-bromo-benzylidene)-1,3-dihydro-indol-2-one
h) 3-E-6-Chloro-3-(4-methyl-benzylidene)-1,3-dihydro-indol-2-one
i) 3-E-6-Chloro-3-(4-methoxyl-benzylidene)-1,3-dihydro-indol-2-one
j) 3-E-6-Chloro-3-(4-trifluoromethyl-benzylidene)-1,3-dihydro-indol-2-one
k) 3-E-6-Chloro-3-(3,4-dichloro-benzylidene)-1,3-dihydro-indol-2-one
l) 3-E-6-Chloro-3-(3,5-dichloro-benzylidene)-1,3-dihydro-indol-2-one
m) 3-E-6-bromo-3-(3-bromo-benzylidene)-1,3-dihydro-indol-2-one
n) 3-E-6-Chloro-3-(3,3-dimethyl-butylidene)-1,3-dihydro-indol-2-one
o) 3-E-6-Chloro-3-(3-methyl-butylidene)-1,3-dihydro-indol-2-one
p) 3-E-6-Chloro-3-(2-cyclohexyl-ethylidene)-1,3-dihydro-indol-2-one
q) 3-E-6-Chloro-3-cyclohexylmethylene-1,3-dihydro-indol-2-one
r) 3-E-6-Chloro-3-cyclopentylmethylene-1,3-dihydro-indol-2-one
s) 3-E-6-Chloro-3-thiophen-2-ylmethylene-1,3-dihydro-indol-2-one
t) 3-E-6-Chloro-3-pyridin-2-ylmethylene-1,3-dihydro-indol-2-one
u) 3-E-3-(6-Chloro-pyridin-2-ylmethylene)-6-chloro-1,3-dihydro-indol-2-one
v) 3-E-3-(3-Chloro-2-fluoro-benzylidene)-6-chloro-1,3-dihydro-indol-2-one
w) 3-E-3-(3-Chloro-4-fluoro-benzylidene)-6-chloro-1,3-dihydro-indol-2-one
x) 3-E-6-Chloro-3-(3-chloro-5-fluoro-benzylidene)-1,3-dihydro-indol-2-one
y) 3-E-3-(3-Bromo-benzylidene)-1,3-dihydro-indol-2-one
z) 3-E-3-(3-Bromo-benzylidene)-6-trifluoromethyl-1,3-dihydro-indol-2-one Example 6

(2'R,3S,4'R,5'R) 6-Bromo-4'-(3-Bromo-Phenyl)-2'-(2,2-Dimethyl-Propyl)-2-Oxo-1,2-Dihydro-Spiro[Indole-3,3'-Pyrrolidine]-5'-Carboxylic Acid Dimethylamide (KE-29)

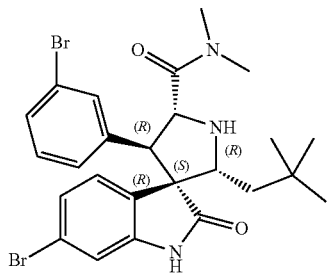

Under argon, to a 100 mL flask with stir bar was added (2S,3R)-2,3,5,6-tetrahydro-2,3-diphenyl-1,4-oxazin-6-one (1.0 g, 3.96 mmol), 3-E-(3-bromo)-benzylidene-6-bromo-1,3-dihydro-indol-2-one (4.75 mmol), 2 g freshly activated 4 A molecular sieves, 3,3-dimethyl-butyraldehyde (4.75 mmol) and toluene (50 mL). The mixture was heated to 70° C. and kept at that temperature for 5 hours. The mixture was cooled to room temperature and the molecular sieves were filtered off. The solvent was removed in vacuo and the residue was purified by chromatography to yield the 1,3-dipolar product.

The 1,3-dipolar product (2.0 mmol) obtained was dissolved in THF-dimethylamine (4 M, 5 mL) and the resulting solution was stirred at room temperature overnight. The solvent was removed in vacuo and the residue was purified by chromatography to yield (1"R,2"S,2'R,3'R,3S,4'R) 6-bromo-4'-(3-bromo-phenyl)-2'-(2,2-dimethyl-propyl)-1'-(2-hydroxy-1,2-diphenyl-ethyl)-2-oxo-1,2-dihydro-spiro[indole-3,3'-pyrrolidine]-5'-carboxylic acid dimethylamide.

At 0° C., to a solution of (1"R,2"S,2'R,3'R,3S,4'R) 6-bromo-4'-(3-bromo-phenyl)-2'-(2,2-dimethyl-propyl)-1'-(2-hydroxy-1,2-diphenyl-ethyl)-2-oxo-1,2-dihydro-spiro[indole-3,3'-pyrrolidine]-5'-carboxylic acid dimethylamide (2.0 mmol) in $CH_2Cl_2$—MeOH (10 mL, 1:1), $Pb(OAc)_4$ (1.34 g, 3.0 mmol) was added. The reaction was stirred at 0° C. for about 5-10 min, and the solution filtered through a short silica gel column. The solvent was removed in vacuo and the residue was purified by chromatography to yield the product.

$[\alpha]^{25}_D$ 82.7 (c, 0.3 $CHCl_3$); $^1H$ NMR (300 MHz, $CDCl_3$), δ 9.15 (br, 1H), 7.20~7.28 (m, 2H);] 7.18~7.03 (m, 2H), 6.97 (s, 1H), 6.86 (d, J=8.00 Hz, 1H), 6.34 (d, J=8.08 Hz, 1H), 4.54 (d, J=7.50 Hz, 1H), 3.99 (d, J=7.49 Hz, 1H), 3.63 (br, 1H), 3.51 (d, J=9.13 Hz, 1H), 3.03 (s, 3H), 2.91 (s, 3H), 1.48 (dd, J=9.85, 14.01 Hz, 1H), 0.90 (d, J=13.50 Hz, 1H), 0.83 (s, 9H); $^{13}C$ NMR (75 MHz, $CDCl_3$), δ 181.16, 170.08, 142.73, 141.20, 131.55, 130.49, 130.06, 127.52, 127.09, 126.08, 124.60, 122.58, 121.46, 113.17, 68.03, 65.15, 64.49, 58.08, 43.12, 37.21, 36.19, 30.10, 29.79.

Example 7

(1"R, 2"S, 2'R, 3S,4'R,5'R) 6-Chloro-4'-Phenyl-1'-(2-Hydroxy-1,2-Diphenyl-Ethyl)-2'-Isobutyl-2-Oxo-1,2-Dihydro-Spiro[Indole-3,3'-Pyrrolidine]-5'-Carboxylic Acid Dimethylamide

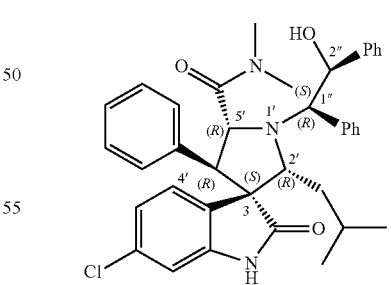

$[\alpha]^{25}_D$, -81.9 (c, 0.3, $CHCl_3$); $^1H$ NMR (300 MHz, $CDCl_3$) δ 8.25 (br, 1H), 7.73 (d, J=7.88 Hz, 1H), 7.42~6.93 (m, 16H), 6.78 (s, 1H), 5.20 (s, 1H), 4.64 (d, J=10.07 Hz, 1H), 4.59 (s, 1H), 4.52 (d, J=3.13 Hz, 1H), 4.17~4.10 (m, 1H), 3.50 (d, J=10.83 Hz, 1H), 2.86 (s, 3H), 2.64 (dd, J=12.45, 13.20 Hz, 1H), 1.95 (s, 3H), 1.73~1.65 (m, 1H), 1.13~1.07 (m, 1H), 0.85 (d, J=6.38 Hz, 3H), 0.54 (d, J=6.08 Hz, 3H); $^{13}C$ NMR (75 MHz, $CDCl_3$) δ 176.43, 174.25, 140.95, 140.55, 135.38, 133.91, 133.77, 131.39, 130.81, 129.78, 127.96, 127.81, 127.58, 126.58, 125.90, 125.36, 122.19, 110.52, 75.52, 75.10, 73.58, 64.71, 60.59, 58.45, 57.52, 37.34, 36.54, 36.30, 29.56, 28.12.

Example 8

(1"R,2"S, 2'R,3S,4'R, 5'R) 6-Chloro-4'-(3-Chloro-Phenyl)-1'-(2-Hydroxy-1,2-Diphenyl-Ethyl)-2'-Isobutyl-2-Oxo-1,2-Dihydro-Spiro[Indole-3,3'-Pyrrolidine]-5'-Carboxylic Acid Dimethylamide

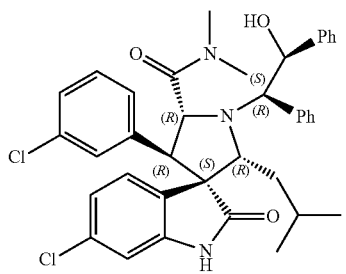

[α]$^{25}_D$, −76.0 (c, 0.2 CHCl$_3$); $^1$H NMR (300 MHz, CDCl$_3$) δ 8.15 (br, 1H), 7.75 (d, J=7.91 Hz, 1H), 7.21~6.86 (m, 14H), 6.82 (d, J=7.82 Hz, 1H), 6.73 (s, 1H), 5.18 (s, 1H), 4.69 (d, J=10.28 Hz, 1H), 4.51 (d, J=3.45 Hz, 1H), 4.32 (br, 1H), 4.22~4.11 (m, 1H), 3.48 (d, J=10.99 Hz, 1H), 2.90 (s, 3H), 2.57 (dd, J=12.53, 13.24 Hz, 1H), 2.06 (s, 3H), 1.85~1.56 (m, 1H), 1.10~0.95 (m, 1H), 0.84 (d, J=6.41 Hz, 3H), 0.47 (d, J=6.90 Hz, 3H); $^{13}$C NMR (75 MHz, CDCl$_3$) δ 176.06, 173.83, 140.80, 140.61, 136.27, 135.04, 134.06, 133.86, 130.81, 130.71, 129.54, 129.23, 128.09, 127.87, 127.62, 127.38, 126.70, 125.80, 125.54, 122.39, 110.60, 73.92, 72.51, 72.23, 62.55, 60.41, 56.75, 39.23, 36.59, 26.43, 23.39, 21.03.

Example 9

(1"R,2"S,2'R,3S,4'R, 5'R) 6-Chloro-4'-(4-Chloro-Phenyl)-1'-(2-Hydroxy-1,2-Diphenyl-Ethyl)-2'-Isobutyl-2-Oxo-1,2-Dihydro-Spiro[Indole-3,3'-Pyrrolidine]-5'-Carboxylic Acid Dimethylamide

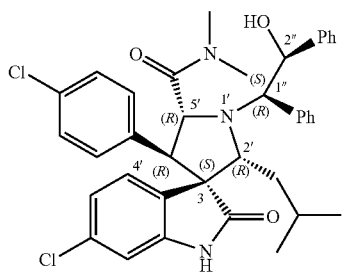

[α]$^{25}_D$, −93.3 (c, 0.2 CHCl$_3$); $^1$H NMR (300 MHz, CDCl$_3$) δ 7.80 (br, 1H), 7.74 (d, J=8.09 Hz, 1H), 7.34~6.90 (m, 14H), 6.91 (d, J=8.41 Hz, 1H), 6.78 (s, 1H), 5.18 (s, 1H), 4.65 (d, J=9.89 Hz, 1H), 4.51 (d, J=3.54 Hz, 1H), 4.36 (br, 1H), 4.18~4.10 (m, 1H), 3.48 (d, J=10.96 Hz, 1H), 2.89 (s, 3H), 2.59 (dd, J=12.39, 12.77 Hz, 1H), 2.05 (s, 3H), 1.70~1.60 (m, 1H), 1.10~1.00 (m, 1H), 0.85 (d, J=6.28 Hz, 3H), 0.49 (d, J=6.10 Hz, 3H); $^{13}$C NMR (75 MHz, CDCl$_3$) δ 175.72, 173.98, 140.71, 140.59, 135.08, 134.02, 133.80, 132.58, 130.86, 130.70, 128.25, 127.87, 127.62, 126.70, 125.80, 125.56, 122.42, 110.50, 74.54, 72.64, 72.19, 62.52, 60.59, 60.41, 56.67, 39.31, 36.58, 26.44, 23.38, 21.06.

Example 10

(1"R, 2"S,2'R, 3S,4'R,5'R) 6-Chloro-4'-(3-Chloro-Phenyl)-2'-(2,2-Dimethyl-Propyl)-1'-(2-Hydroxy-1,2-Diphenyl-Ethyl)-2-Oxo-1,2-Dihydro-Spiro[Indole-3,3'-Pyrrolidine]-5'-Carboxylic Acid Dimethylamide

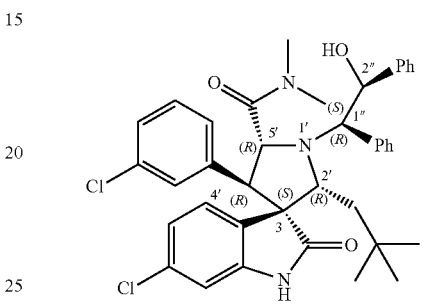

[α]$^{25}_D$, −92.7 (c, 0.6 CHCl$_3$); $^1$H NMR (300 MHz, CDCl$_3$) δ 7.85 (br, 1H), 7.45 (d, J=8.10 Hz, 2H), 7.41~6.72 (m, 14H), 6.68 (d, J=7.72 Hz, 1H), 5.43 (d, J=3.24 Hz, 1H), 4.84 (br, 1H), 4.50 (d, J=3.55 Hz, 1H), 4.38 (d, J=10.46 Hz, 1H), 3.98 (d, J=10.46 Hz, 1H), 3.65 (d, J=9.00 Hz, 1H), 2.97 (dd, J=9.00 Hz, 12.00 Hz, 1H), 2.86 (s, 3H), 1.94~1.85 (m, 1H), 1.93 (s, 3H), 0.79 (s, 9H); $^{13}$C NMR (75 MHz, CDCl$_3$) δ 174.32, 140.84, 135.61, 135.32, 134.20, 133.71, 130.97, 129.51, 129.08, 128.16, 128.02, 127.60, 127.41, 126.48, 125.89, 125.17, 122.41, 110.48, 74.85, 73.82, 72.00, 62.31, 60.94, 60.41, 57.92, 42.19, 36.69, 30.31, 29.68.

Example 11

(1"R,2"S,2'R,3S,4'R, 5'R) 6-Chloro-4'-(3-Chloro-Phenyl)-1'-(2-Hydroxy-1,2-Diphenyl-Ethyl)-2'-Propyl-2-Oxo-1,2-Dihydro-Spiro[Indole-3,3'-Pyrrolidine]-5'-Carboxylic Acid Dimethylamide

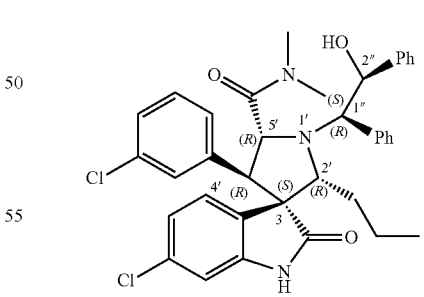

[α]$^{25}_D$, −73.9 (c, 0.3 CHCl$_3$); $^1$H NMR (300 MHz, CDCl$_3$) δ 8.27 (br, 1H), 7.66 (d, J=8.01 Hz, 1H), 7.63 (d, J=6.97 Hz, 1H), 7.42 (d, J=6.99 Hz, 1H), 7.32 (d, J=7.26 Hz, 1H), 7.28~6.57 (m, 14H), 5.14 (s, 1H), 4.60 (d, J=10.06 Hz, 1H), 4.58~4.48 (m, 1H), 4.48 (d, J=3.32 Hz, 1H), 4.17~4.10 (m, 1H), 3.37 (d, J=10.11 Hz, 1H), 2.87 (s, 3H), 2.56~2.40 (m, 1H), 1.99 (s, 3H), 2.00~1.88 (m, 1H), 1.10~0.87 (m, 2H), 0.27~0.72 (m, 3H).

Example 12

(1″R,2″S,2′R,3S,4′R,5′R) 6-Chloro-4′-(3-Chloro-Phenyl)-1′-(2-Hydroxy-1,2-Diphenyl-Ethyl)-2′-(3-Methyl-Butyl)-2-Oxo-1,2-Dihydro-Spiro[Indole-3,3′-Pyrrolidine]-5′-Carboxylic Acid Dimethylamide

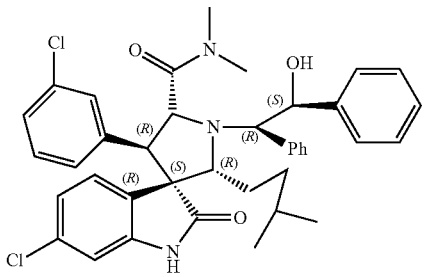

[α]$^{25}_D$, −85.6 (c, 0.4 CHCl$_3$); $^1$H NMR (300 MHz, CDCl$_3$) δ 8.68 (br, 1H), 7.63 (d, J=7.77 Hz, 1H), 7.28~6.81 (m, 16H), 5.13 (s, 1H), 4.59 (d, J=10.12 Hz, 1H), 4.54 (s, 1H), 4.46 (d, J=2.94 Hz, 1H), 4.12 (d, J=10.10 Hz, 1H), 3.31 (d, J=10.26 Hz, 1H), 2.85 (s, 3H), 2.60~2.45 (m, 1H), 1.99 (s, 3H), 1.95~1.84 (m, 1H), 1.48~1.42 (m, 1H), 0.95~0.82 (m, 1H), 0.77 (t, J=5.50 Hz, 6H), 0.70~0.60 (m, 1H); $^{13}$C NMR (75 MHz, CDCl$_3$) δ 176.58, 173.82, 140.98, 140.53, 136.12, 135.21, 134.03, 133.76, 130.75, 129.43, 129.16, 128.04, 127.81, 127.59, 127.32, 126.64, 125.86, 125.30, 122.29, 110.75, 75.18, 74.99, 73.10, 62.68, 60.39, 56.99, 37.22, 36.57, 36.42, 29.19, 28.08, 22.61.

Example 13

(2′R,3S,4′R, 5′R) 6-Chloro-4′-(3,4-Dichloro-Phenyl)-2′-(2,2-Dimethyl-Propyl)-2-Oxo-1,2-Dihydro-Spiro[Indole-3,3′-Pyrrolidine]-5′-Carboxylic Acid Dimethylamide (KE-32)

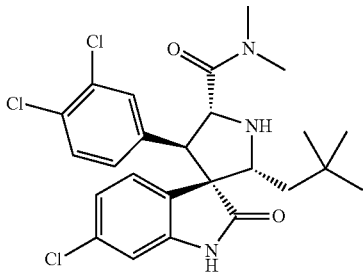 [SMILES: CN(C)C(=O)[C@@H]1N[C@H](CC(C)(C)C)[C@]2(C(=O)Nc3cc(Cl)ccc32)[C@H]1c1ccc(Cl)c(Cl)c1]

Using a method similar to that in Example 6, this compound was synthesized.

[α]$^{25}_D$ 128.0 (c, 0.2 CHCl$_3$); $^1$H NMR (300 MHz, CDCl$_3$), δ 8.64 (s, 1H), 7.35 (s, 1H), 7.22 (d, J=1.79 Hz, 1H), 6.97 (dd, J=1.80, 8.30 Hz, 1H); 6.88 (d, J=1.65 Hz, 1H), 6.78 (dd, J=1.75, 8.10 Hz, 1H), 6.35 (d, J=8.06 Hz, 1H), 4.47 (d, J=7.92 Hz, 1H), 4.07 (d, J=7.91 Hz, 1H), 3.48 (d, J=9.47 Hz, 1H), 3.03 (s, 3H), 2.91 (s, 3H), 1.49 (dd, J=9.88, 14.3 Hz, 1H); 0.90~0.88 (m, 1H), 0.84 (s, 9H); $^{13}$C NMR (75 MHz, CDCl$_3$), δ 180.88, 169.71, 142.30, 139.07, 133.72, 132.55, 131.32, 130.41, 127.14, 126.60, 125.69, 121.99, 110.41, 68.64, 65.41, 64.20, 57.67, 43.15, 37.28, 36.16, 30.14, 29.81.

Example 14

(2′R,3S,4′R,5′R) 6-Chloro-2′-(2,2-Dimethyl-Propyl)-2-Oxo-4′-(3-Trifluoromethyl-Phenyl)-1,2-Dihydro-Spiro[Indole-3,3′-Pyrrolidine]-5′-Carboxylic Acid Dimethylamide (KE-21)

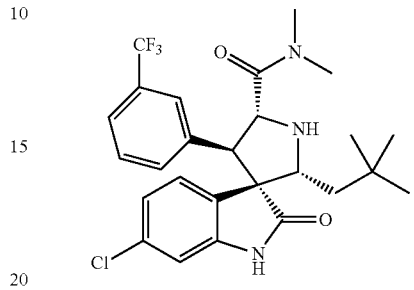

Using a method similar to that in Example 6, this compound was synthesized.

[α]$^{25}_D$ 61.0 (c, 0.2 CHCl$_3$); $^1$H NMR (300 MHz, CDCl$_3$), δ 8.19 (br, 1H), 7.45~7.21 (m, 4H), 6.82 (d, J=1.82 Hz, 1H), 6.70 (dd, J=1.90, 8.12 Hz, 1H), 6.39 (d, J=8.11 Hz, 1H), 4.57 (d, J=8.28 Hz, 1H), 4.18 (d, J=8.10 Hz, 1H), 3.50 (d, J=9.80 Hz, 1H), 2.99 (s, 3H), 2.93 (s, 3H), 1.52 (dd, J=9.84, 14.22 Hz, 1H), 0.96 (d, J=14.23 Hz, 1H), 0.90 (s, 9H); $^{13}$C NMR (75 MHz, CDCl$_3$), δ 180.70, 169.84, 142.03, 139.71, 133.64, 132.33, 129.09, 126.72, 125.73, 125.06, 124.09, 121.89, 110.14, 68.44, 65.05, 64.38, 58.55, 43.26, 37.02, 36.15, 30.17, 29.82; EI/MS, 508 (M$^+$+1); HRMS C$_{26}$H$_{30}$ClF$_3$N$_3$O$_2$ ([M+H]$^+$) required 508.1979. found 508.1965.

Example 15

(2′R,3S,4′R, 5′R) 6-Chloro-4′-(4-Chloro-Phenyl)-2′-Isobutyl-2-Oxo-1,2-Dihydro-Spiro[Indole-3,3′-Pyrrolidine]-5′-Carboxylic Acid Dimethylamide (KE-10)

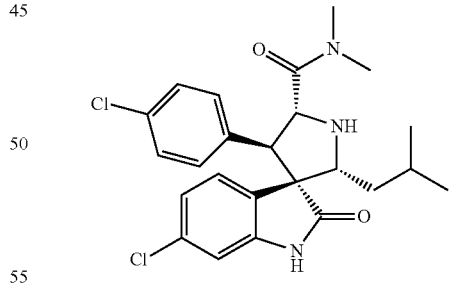

Using a method similar to that in Example 6, this compound was synthesized.

[α]$^{25}_D$ 68.0 (c, 0.3 CHCl$_3$); $^1$H NMR (300 MHz, CDCl$_3$), δ 8.98 (br, 1H), 7.21 (d, J=8.18 Hz, 2H), 7.09 (d, J=8.17 Hz, 2H), 6.86 (s, 1H), 6.74 (d, J=7.75 Hz, 1H), 6.46 (d, J=7.78 Hz, 1H), 4.59 (d, J=7.63 Hz, 1H), 3.99 (d, J=7.64 Hz, 1H), 3.56 (m, 1H), 2.96 (s, 3H), 2.85 (s, 3H), 1.68~1.53 (m, 2H), 0.98~0.88 (m, 1H), 0.79 (d, J=12.1 Hz, 3H), 0.77 (d, J=12.0 Hz, 3H); $^{13}$C NMR (75 MHz, CDCl$_3$), δ 180.86, 170.40, 142.35, 136.85, 133.62, 133.28, 130.04, 128.76, 127.16, 125.73, 121.87, 110.29, 68.90, 64.35, 63.60, 59.40, 38.66, 37.24, 36.24, 25.83, 23.42, 21.76; EI/MS, 460 (M$^+$+1); HRMS C$_{24}$H$_{28}$Cl$_2$N$_3$O$_2$ ([M+H]$^+$) required 460.1559. found 460.1552.

Example 16

(2'S,3R,4'S,5'S) 6-Chloro-4'-(4-Chloro-Phenyl)-2'-Isobutyl-2-Oxo-1,2-Dihydro-Spiro[Indole-3,3'-Pyrrolidine]-5'-Carboxylic Acid Dimethylamide (KE-38)

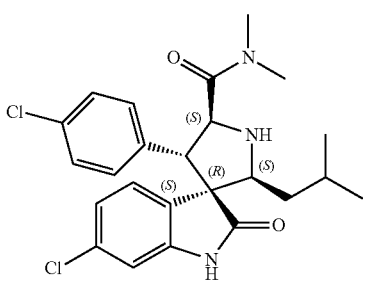

[α]$^{25}_D$ -65.8 (c, 0.3 CHCl$_3$); $^1$H NMR (300 MHz, CDCl$_3$), δ 8.98 (br, 1H), 7.21 (d, J=8.18 Hz, 2H), 7.09 (d, J=8.17 Hz, 2H), 6.86 (s, 1H), 6.74 (d, J=7.75 Hz, 1H), 6.46 (d, J=7.78 Hz, 1H), 4.59 (d, J=7.63 Hz, 1H), 3.99 (d, J=7.64 Hz, 1H), 3.56 (m, 1H), 2.96 (s, 3H), 2.85 (s, 3H), 1.68~1.53 (m, 2H), 0.98~0.88 (m, 1H), 0.79 (d, J=12.1 Hz, 3H), 0.77 (d, J=12.0 Hz, 3H); $^{13}$C NMR (75 MHz, CDCl$_3$), δ 180.86, 170.40, 142.35, 136.85, 133.62, 133.28, 130.04, 128.76, 127.16, 125.73, 121.87, 110.29, 68.90, 64.35, 63.60, 59.40, 38.66, 37.24, 36.24, 25.83, 23.42, 21.76; EI/MS, 460 (M$^+$+1); HRMS C$_{24}$H$_{28}$Cl$_2$N$_3$O$_2$ ([M+H]$^+$) required 460.1559. found 460.1552.

Example 17

(2'S,3R,4'S,5'S) 6-Chloro-4'-(3-Chloro-Phenyl)-2'-Isobutyl-2-Oxo-1,2-Dihydro-Spiro[Indole-3,3'-Pyrrolidine]-5'-Carboxylic Acid Dimethylamide (KE-34)

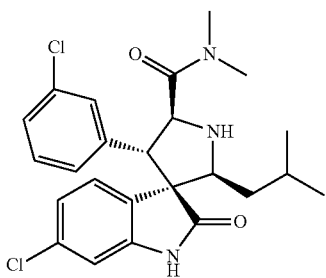 [SMILES: CC(C)C[C@@H]1N[C@H](C(=O)N(C)C)[C@@H](c2cccc(Cl)c2)[C@]12C(=O)Nc1cc(Cl)ccc12]

[α]$^{25}_D$ -50.0 (c, 0.3 CHCl$_3$); $^1$H NMR (300 MHz, CDCl$_3$), δ 9.30 (br, 1H), 7.27~6.95 (m, 4H), 6.88 (s, 1H), 6.73 (d, J=8.00 Hz, 1H), 6.47 (d, 8.01 Hz, 1H), 4.61 (d, J=7.66 Hz, 1H), 4.00 (d, J=7.64 Hz, 1H), 3.58~3.54 (m, 1H), 2.97 (s, 3H), 2.88 (s, 3H), 1.65~1.45 (m, 2H), 0.98~0.91 (m, 1H), 0.78 (d, J=6.63 Hz, 3H), 0.76 (d, J=6.53 Hz, 3H); $^{13}$C NMR (75 MHz, CDCl$_3$), δ 180.98, 170.23, 142.44, 140.40, 134.35, 133.58, 129.77, 128.68, 127.64, 126.94, 125.64, 121.75, 110.36, 68.84, 64.08, 63.59, 59.50, 38.54, 37.22, 36.21, 25.78, 23.38, 21.72; EI/MS, 460 (M$^+$+1); HRMS C$_{24}$H$_{28}$Cl$_2$N$_3$O$_2$ ([M+H]$^+$) required 460.1559. found 460.1551.

Example 18

(2'R,3S,4'R,5'R) 6-Chloro-4'-(3-Chloro-Phenyl)-2'-Isobutyl-2-Oxo-1,2-Dihydro-Spiro[Indole-3,3'-Pyrrolidine]-5'-Carboxylic Acid Dimethylamide (KE-9)

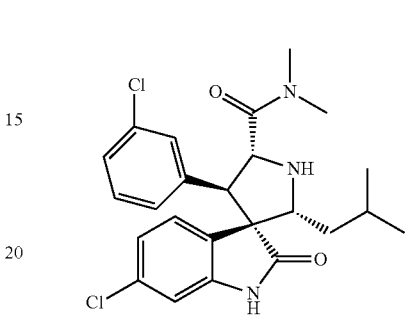

[α]$^{25}_D$ 50.0 (c, 0.3 CHCl$_3$); $^1$HNMR (300 MHz, CDCl$_3$), δ 9.30 (br, 1H), 7.27~6.95 (m, 4H), 6.88 (s, 1H), 6.73 (d, J=8.00 Hz, 1H), 6.47 (d, 8.01 Hz, 1H), 4.61 (d, J=7.66 Hz, 1H), 4.00 (d, J=7.64 Hz, 1H), 3.58~3.54 (m, 1H), 2.97 (s, 3H), 2.88 (s, 3H), 1.65~1.45 (m, 2H), 0.98~0.91 (m, 1H), 0.78 (d, J=6.63 Hz, 3H), 0.76 (d, J=6.53 Hz, 3H); $^{13}$CNMR (75 MHz, CDCl$_3$), δ 180.98, 170.23, 142.44, 140.40, 134.35, 133.58, 129.77, 128.68, 127.64, 126.94, 125.64, 121.75, 110.36, 68.84, 64.08, 63.59, 59.50, 38.54, 37.22, 36.21, 25.78, 23.38, 21.72; EI/MS, 460 (M$^+$+1); HRMS C$_{24}$H$_{28}$Cl$_2$N$_3$O$_2$ ([M+H]$^+$) required 460.1559. found 460.1551.

Example 19

(2'R,3S,4'R,5'R) 6-Chloro-2'-Isobutyl-2-Oxo-4'-Phenyl-1,2-Dihydro-Spiro[Indole-3,3'-Pyrrolidine]-5'-Carboxylic Acid Dimethylamide (KE-5)

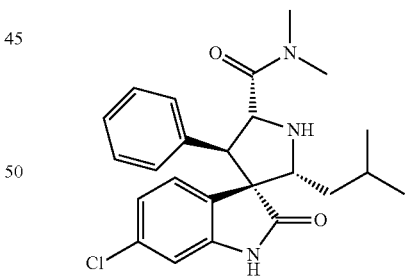

[α]$^{25}_D$ 24.7 (c, 0.8 CHCl$_3$); $^1$H NMR (300 MHz, CDCl$_3$), δ 8.20 (br, 1H), 7.38~7.01 (m, 5H), 6.80 (d, J=1.86 Hz, 1H), 6.66 (dd, J=1.91, 8.10 Hz, 1H), 6.32 (d, J=8.13 Hz, 1H), 4.63 (d, J=7.12 Hz, 1H), 3.94 (d, J=7.18 Hz, 1H), 3.65~3.55 (m, 1H), 2.97 (s, 3H), 2.75 (s, 3H), 1.76~1.51 (m, 2H), 0.99~0.88 (m, 1H), 0.82 (d, J=6.63 Hz, 3H), 0.78 (d, J=6.52 Hz, 3H); $^{13}$C NMR (75 MHz, CDCl$_3$), δ 180.54, 170.75, 142.16, 138.68, 133.34, 128.78, 128.63, 128.43, 128.30, 127.56, 127.11, 125.85, 121.67, 109.86, 68.75, 64.59, 63.72, 59.87, 38.58, 37.14, 36.23, 25.85, 23.49, 21.74; EI/MS, 426 (M$^+$+1); HRMS C$_{24}$H$_{29}$ClN$_3$O$_2$ ([M+H]$^+$) required 426.1948. found 426.1937.

Example 20

(2'S,3R,4'S,5'S) 6-Chloro-2'-Isobutyl-2-Oxo-4'-Phenyl-1,2-Dihydro-Spiro[Indole-3,3'-Pyrrolidine]-5'-Carboxylic Acid Dimethylamide (KE-4)

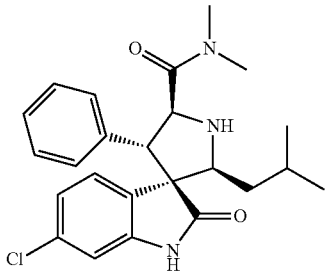 [SMILES: CC(C)C[C@@H]1N[C@H](C(=O)N(C)C)[C@@H](c2ccccc2)[C@]12C(=O)Nc1cc(Cl)ccc12]

$[\alpha]^{25}_D$ −24.7 (c, 0.8 CHCl$_3$); $^1$HNMR (300 MHz, CDCl$_3$), δ 8.20 (br, 1H), 7.38~7.01 (m, 5H), 6.80 (d, J=1.86 Hz, 1H), 6.66 (dd, J=1.91, 8.10 Hz, 1H), 6.32 (d, J=8.13 Hz, 1H), 4.63 (d, J=7.12 Hz, 1H), 3.94 (d, J=7.18 Hz, 1H), 3.65~3.55 (m, 1H), 2.97 (s, 3H), 2.75 (s, 3H), 1.76~1.51 (m, 2H), 0.99~0.88 (m, 1H), 0.82 (d, J=6.63 Hz, 3H), 0.78 (d, J=6.52 Hz, 3H); $^{13}$CNMR (75 MHz, CDCl$_3$), δ 180.54, 170.75, 142.16, 138.68, 133.34, 128.78, 128.63, 128.43, 128.30, 127.56, 127.11, 125.85, 121.67, 109.86, 68.75, 64.59, 63.72, 59.87, 38.58, 37.14, 36.23, 25.85, 23.49, 21.74; EI/MS, 426 (M$^+$+1); HRMS C$_{24}$H$_{29}$ClN$_3$O$_2$ ([M+H]$^+$) required 426.1948. found 426.1937.

Example 21

(2'R,3S,4'R,5'R) 6-Chloro-4'-(3-Chloro-Phenyl)-2'-(3-Methyl-Butyl)-2-Oxo-1,2-Dihydro-Spiro[Indole-3,3'-Pyrrolidine]-5'-Carboxylic Acid Dimethylamide (KE-16)

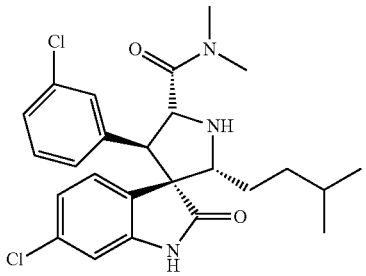

$[\alpha]^{25}_D$ 25.1 (c, 0.5 CHCl$_3$); $^1$H NMR (300 MHz, CDCl$_3$), δ 8.15 (br, 1H), 7.21~7.07 (m, 4H), 6.81 (s, 1H), 6.76 (dd, J=1.85, 8.06 Hz, 1H), 6.49 (d, J=8.08 Hz, 1H), 4.69 (d, J=7.90 Hz, 1H), 3.96 (d, J=7.89 Hz, 1H), 3.53 (dd, J=8.64, 9.19 Hz, 1H), 2.97 (s, 3H), 2.85 (s, 3H), 1.68~1.56 (m, 1H), 1.46~1.36 (m, 1H), 1.30~1.20 (m, 2H), 1.11~0.99 (m, 1H), 0.78 (d, J=6.46 Hz, 3H), 0.75 (d, J=6.48 Hz, 3H); $^{13}$C NMR (75 MHz, CDCl$_3$), δ 180.00, 170.08, 141.83, 140.20, 134.45, 133.70, 129.82, 128.73, 127.78, 127.13, 126.93, 125.94, 121.98, 110.03, 70.69, 63.56, 63.33, 59.70, 40.43, 37.21, 36.51, 27.86, 27.33, 22.54, 22.15. EI/MS, 474 (M$^+$+1); HRMS C$_{25}$H$_{30}$Cl$_2$N$_3$O$_2$ ([M+H]$^+$) required 474.1715. found 474.1714.

Example 22

(2'R,3S,4'R,5'R) 6-Chloro-2'-(2,2-Dimethyl-Propyl)-4'-(3-Iodo-Phenyl)-2-Oxo-1,2-Dihydro-Spiro[Indole-3,3'-Pyrrolidine]-5'-Carboxylic Acid Dimethylamide (KE-22)

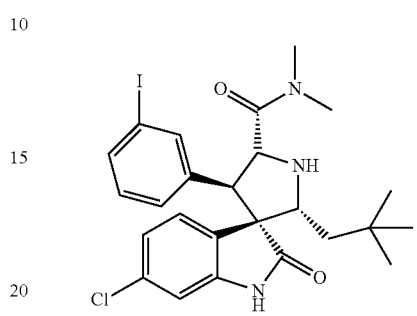

$[\alpha]^{25}_D$ 84.2 (c, 0.4 CHCl$_3$); $^1$H NMR (300 MHz, CDCl$_3$), δ 8.79 (br, 1H), 7.50 (m, 2H), 7.15 (d, J=7.68 Hz, 1H), 6.96 (dd, J=7.80, 8.10 Hz, 1H), 6.81 (s, 1H), 6.73 (dd, J=1.59, 8.10 Hz, 1H), 6.40 (d, J=9.10 Hz, 1H), 4.52 (d, J=7.50 Hz, 1H), 3.96 (d, J=7.50 Hz, 1H), 3.50 (d, J=9.96 Hz, 1H), 2.98 (s, 3H), 2.91 (s, 3H), 1.48 (dd, J=9.90, 14.11 Hz, 1H), 0.89-0.85 (m, 1H), 0.84 (s, 9H), $^{13}$C NMR (75 MHz, CDCl$_3$), δ 181.03, 170.10, 142.37, 141.28, 137.15, 136.45, 133.54, 129.98, 128.12, 126.60, 125.82, 121.75, 110.28, 94.45, 68.18, 65.17, 64.43, 60.40, 43.17, 37.23, 36.19, 30.13, 29.82; EI/MS, 566 (M$^+$+1); HRMS C$_{25}$H$_{30}$Cl$_1$N$_3$O$_2$ ([M+H]$^+$) required 566.1071. found 566.1063.

Example 23

(2'R,3S,4'R,5'R) 6-Chloro-2'-(2,2-Dimethyl-Propyl)-2-Oxo-4'-Phenyl-1,2-Dihydro-Spiro[Indole-3,3'-Pyrrolidine]-5'-Carboxylic Acid Dimethylamide (KE-7)

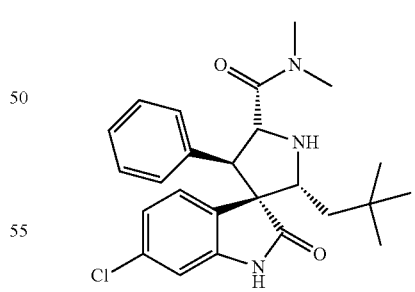

$[\alpha]^{25}_D$ 53.3 (c, 0.9 CHCl$_3$); $^1$H NMR (300 MHz, CDCl$_3$), δ 7.68 (br, 1H), 7.28~7.12 (m, 5H), 6.78 (d, J=1.84 Hz, 1H), 6.43 (dd, J=1.88, 8.14 Hz, 1H), 6.23 (d, J=8.13 Hz, 1H), 4.60 (d, J=6.81 Hz, 1H), 3.92 (d, J=6.84 Hz, 1H), 3.53 (d, J=8.99 Hz, 1H), 3.39 (br, 1H), 2.98 (s, 3H), 2.76 (s, 3H), 1.48 (dd, J=9.64, 14.35 Hz, 1H), 0.97~0.90 (m, 1H), 0.86 (s, 9H), EI/MS, 440 (M$^+$+1); HRMS C$_{25}$H$_{30}$ClN$_3$O$_2$ ([M+H]$^+$) required 440.2105. found 440.2102.

Example 24

(2'S,3R,4'S,5'S) 6-Chloro-2'-(2,2-Dimethyl-Propyl)-2-Oxo-4'-Phenyl-1,2-Dihydro-Spiro[Indole-3,3'-Pyrrolidine]-5'-Carboxylic Acid Dimethylamide (KE-14)

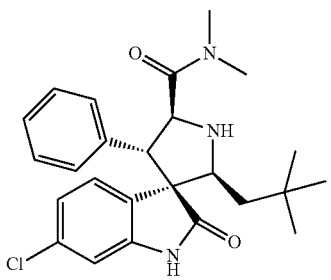 [SMILES: CN(C)C(=O)[C@H]1N[C@@H](CC(C)(C)C)[C@@]2(C(=O)Nc3cc(Cl)ccc32)[C@@H]1c1ccccc1]

$[\alpha]^{25}_D$-50.6 (c, 0.6 CHCl$_3$); $^1$H NMR (300 MHz, CDCl$_3$), δ 7.68 (br, 1H), 7.28~7.12 (m, 5H), 6.78 (d, J=1.84 Hz, 1H), 6.43 (dd, J=1.88, 8.14 Hz, 1H), 6.23 (d, J=8.13 Hz, 1H), 4.60 (d, J=6.81 Hz, 1H), 3.92 (d, J=6.84 Hz, 1H), 3.53 (d, J=8.99 Hz, 1H), 3.39 (br, 1H), 2.98 (s, 3H), 2.76 (s, 3H), 1.48 (dd, J=9.64, 14.35 Hz, 1H), 0.97~0.90 (m, 1H), 0.86 (s, 9H), EI/MS, 440 (M$^+$+1); HRMS C$_{25}$H$_{30}$ClN$_3$O$_2$ ([M+H]$^+$) required 440.2105. found 440.2102.

Example 25

(2'R,3S,4'R,5'R) 6-Chloro-4'-(3,5-Dichloro-Phenyl)-2'-(2,2-Dimethyl-Propyl)-2-Oxo-1,2-Dihydro-Spiro[Indole-3,3'-Pyrrolidine]-5'-Carboxylic Acid Dimethylamide (KE-20)

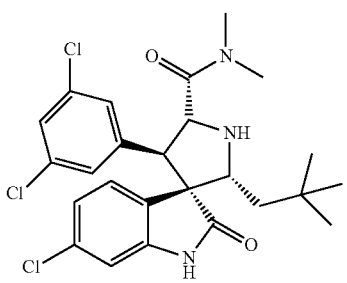

$[\alpha]^{25}_D$ 69.1 (c, 0.6 CHCl$_3$); $^1$H NMR (300 MHz, CDCl$_3$), δ 8.03 (br, 1H), 7.33 (d, J=8.00 Hz, 1H), 7.13 (s, 1H), 7.12 (dd, J=1.84, 7.95 Hz, 1H), 7.04 (d, J=1.85 Hz, 2H), 6.80 (d, 1.84 Hz, 1H), 4.73 (d, J=8.52 Hz, 1H), 4.48 (d, J=8.51 Hz, 1H), 3.68 (d, J=9.12 Hz, 1H), 3.08 (s, 3H), 2.96 (s, 3H), 1.44~1.22 (m, 1H), 0.99~0.89 (m, 1H), 0.84 (s, 9H), $^{13}$C NMR (75 MHz, CDCl$_3$), δ 181.07, 172.13, 141.75, 139.98, 134.69, 134.00, 127.69, 127.04, 126.36, 123.48, 123.11, 110.55, 66.57, 66.08, 61.65, 56.48, 43.34, 37.49, 36.32, 30.15, 29.78.

Example 26

(2'R,3S,4'R,5'R) 6-Chloro-4'-(3-Chloro-Phenyl)-2'-(2,2-Dimethyl-Propyl)-5'-(4-Methyl-Piperazine-1-Carbonyl)-1H-Spiro[Indole-3,3'-Pyrrolidin]-2-One (KE-27)

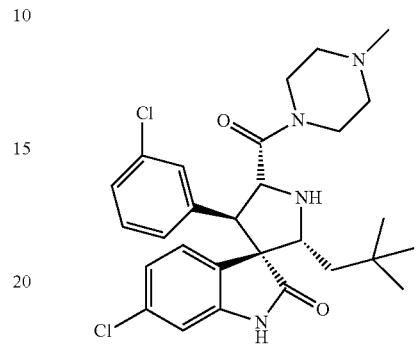

$[\alpha]^{25}_D$ 88.5 (c, 0.2 CHCl$_3$); $^1$H NMR (300 MHz, CDCl$_3$), δ 8.91 (br, 1H), 7.18~7.14 (m, 3H), 7.05~7.02 (m, 1H), 6.85 (d, J=1.58 Hz, 1H), 6.72 (dd, J=1.61, 8.11 Hz, 1H), 6.41 (d, J=8.12 Hz, 1H), 4.50 (d, J=7.42 Hz, 1H), 3.99 (d, J=7.49 Hz, 1H), 3.68~3.35 (m, 7H), 2.41~2.33 (m, 2H), 2.25 (s, 3H), 1.47 (dd, J=9.90, 14.15 Hz, 1H), 1.03~0.88 (m, 1H), 0.72 (s, 9H); $^{13}$C NMR (75 MHz, CDCl$_3$), δ 181.12, 168.55, 142.42, 140.76, 134.47, 133.62, 129.89, 128.73, 127.69, 127.06, 126.42, 125.79, 121.85, 110.30, 67.99, 65.24, 64.27, 58.01, 54.57, 54.29, 45.49, 45.09, 43.08, 42.03, 30.13, 29.79.

Example 27

(2'S,3S,4'R,5'R) 6-Chloro-2'-(4-Chloro-Phenyl)-4'-(2,2-Dimethyl-Propyl)-2-Oxo-1,2-Dihydro-Spiro[Indole-3,3'-Pyrrolidine]-5'-Carboxylic Acid Dimethylamide (KE-39)

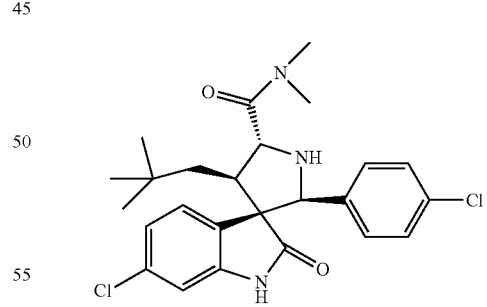

$[\alpha]^{25}_D$ 124.0 (c, 0.2 CHCl$_3$); $^1$H NMR (300 MHz, CDCl$_3$), δ 8.46 (br, 1H), 7.25~7.09 (m, 3H), 7.02 (dd, J=7.85, 7.93 Hz, 1H), 6.92 (s, 1H), 6.75 (s, 1H), 6.43 (d, J=7.45 Hz, 1H), 4.31 (s, 1H), 4.02 (d, J=6.82 Hz, 1H), 3.28 (s, 1H), 3.12~3.06 (m, 1H), 3.06 (s, 3H), 2.96 (s, 3H), 1.59 (dd, J=7.69, 7.80 Hz, 1H), 1.23~1.18 (m, 1H), 0.55 (s, 9H); $^{13}$C NMR (75 MHz, CDCl$_3$), δ 180.58, 170.44, 142.54, 137.79, 133.99, 133.84, 129.18, 129.00, 128.19, 126.32, 126.19, 124.28, 122.13, 110.61, 74.67, 66.15, 60.40, 50.42, 42.21, 38.88, 37.68, 30.30, 28.90.

Example 28

(2R,3S,4'R,5'R) 4'-(3-Bromo-Phenyl)-6-Chloro-2'-(2,2-Dimethyl-Propyl)-5'-(Morpholine-4-Carbonyl)-1H-Spiro[Indole-3,3'-Pyrrolidin]-2-One (KE-28)

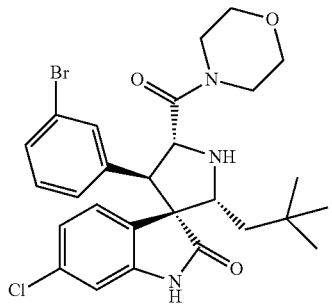 [SMILES: CC(C)(C)C[C@H]1N[C@@H](C(=O)N2CCOCC2)[C@H](c2cccc(Br)c2)[C@@]12C(=O)Nc1cc(Cl)ccc12]

$^1$H NMR (300 MHz, CDCl$_3$), δ 8.36 (br, 1H), 7.34~7.25 (m, 2H), 7.14~7.04 (m, 2H), 6.86 (s, 1H), 6.74 (d, J=7.87 Hz, 1H), 6.44 (d, J=7.99 Hz, 1H), 4.45 (d, J=7.64 Hz, 1H), 4.05 (d, J=7.51 Hz, 1H), 3.66~3.23 (m, 9H) 1.53~1.43 (m, 1H), 1.05~0.90 (m, 1H), 0.85 (s, 9H).

Example 29

(2'R,3S,4'R,5'R) 6-Chloro-4'-(3-Chloro-Phenyl)-2'-(2,2-Dimethyl-Propyl)-5'-(Morpholine-4-Carbonyl)-1H-Spiro[Indole-3,3'-Pyrrolidin]-2-One (KE-26)

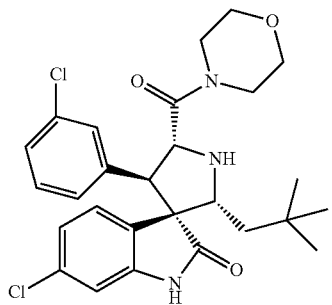 [SMILES: CC(C)(C)C[C@H]1N[C@@H](C(=O)N2CCOCC2)[C@H](c2cccc(Cl)c2)[C@@]12C(=O)Nc1cc(Cl)ccc12]

[α]$^{25}_D$ 56.5 (c, 0.2 CHCl$_3$); $^1$H NMR (300 MHz, CDCl$_3$), δ 8.76 (br, 1H), 7.18~7.15 (m, 3H), 7.04~7.01 (m, 1H), 6.86 (d, J=1.86 Hz, 1H), 6.72 (dd, J=1.76, 8.10 Hz, 1H), 6.42 (d, J=8.13 Hz, 1H), 4.46 (d, J=7.57 Hz, 1H), 4.04 (d, J=7.55 Hz, 1H), 3.66~3.30 (m, 9H), 1.46 (dd, J=9.94, 14.09 Hz, 1H), 1.04~0.89 (m, 1H), 0.84 (s, 9H); $^{13}$C NMR (75 MHz, CDCl$_3$), δ 181.05, 168.71, 142.40, 140.74, 134.48, 133.62, 129.90, 128.66, 127.71, 127.08, 126.37, 125.75, 121.84, 110.32, 68.29, 66.78, 66.58, 65.41, 64.26, 57.97, 46.17, 43.02, 30.13, 29.80.

Example 30

(2'R,3S,4'R,5'R) 4'-(3-Bromo-Phenyl)-6-Chloro-2'-(2,2-Dimethyl-Propyl)-2-Oxo-1,2-Dihydro-Spiro[Indole-3,3'-Pyrrolidine]-5'-Carboxylic Acid Dimethylamide (KE-23)

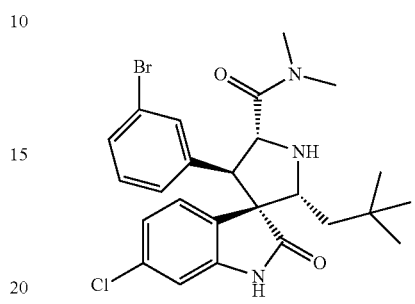

$^1$H NMR (300 MHz, CDCl$_3$), δ 8.73 (br, 1H), 7.33~7.28 (m, 2H), 7.14~7.07 (m, 2H), 6.86 (d, J=1.79 Hz, 1H), 6.72 (dd, J=1.86, 8.10 Hz, 1H), 6.40 (d, J=8.13 Hz, 1H), 4.54 (d, J=7.54 Hz, 1H), 4.00 (d, J=7.53 Hz, 1H), 3.50 (d, J=8.63 Hz, 1H), 2.92 (s, 3H), 2.87 (s, 3H), 1.52~1.44 (m, 1H), 0.97~0.92 (m, 1H), 0.89 (s, 9H); $^{13}$C NMR (75 MHz, CDCl$_3$), δ 181.49, 170.49, 142.76, 141.68, 134.00, 132.02, 130.95, 130.51, 127.96, 127.02, 126.23, 123.05, 122.24, 110.70, 62.59, 65.62, 64.85, 60.84, 58.59, 43.61, 37.66, 36.62, 30.57, 30.25. EI/MS, 518 (M$^+$+1); HRMS C$_{25}$H$_{39}$BrClN$_3$O$_2$ ([M+H]$^+$) required 518.1210. found 518.1177.

Example 31

(2'R,3S,4'R,5'R) 6-Chloro-4'-(3-Chloro-Phenyl)-2-Oxo-2'-Propyl-1,2-Dihydro-Spiro[Indole-3,3'-Pyrrolidine]-5'-Carboxylic Acid Dimethylamide (KE-30)

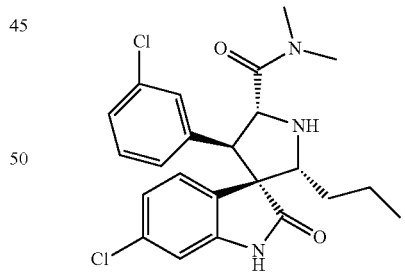

[α]$^{25}_D$ 42.2 (c, 1.0 CHCl$_3$); $^1$H NMR (300 MHz, CDCl$_3$), δ 9.39 (br, 1H), 7.16~7.05 (m, 4H), 6.87 (s, 1H), 6.74 (d, J=7.98 Hz, 1H), 5.49 (d, J=8.07 Hz, 1H), 4.62 (d, J=7.82 Hz, 1H), 4.00 (d, J=7.81 Hz, 1H), 3.51 (dd, J=9.15, 9.27 Hz, 1H), 2.97 (s, 3H), 2.74 (s, 3H), 1.65~1.44 (m, 2H), 1.29~1.18 (m, 2H), 0.77 (t, J=7.15 Hz, 3H); $^{13}$C NMR (75 MHz, CDCl$_3$), δ 180.89, 170.27, 142.47, 140.30, 134.34, 133.59, 129.75, 128.67, 127.65, 127.21, 126.94, 125.73, 121.73, 110.34, 70.65, 63.85, 63.49, 59.66, 37.21, 36.21, 31.92, 20.77, 14.00; EI/MS, 446 (M$^+$+1); HRMS C$_{23}$H$_{26}$Cl$_2$N$_3$O$_2$ ([M+H]$^+$) required 446.1402. found 446.1408.

Example 32

(2'R,3S,4'R,5'R) 6-Chloro-2'-(2,2-Dimethyl-Propyl)-4'-(3-Methoxy-Phenyl)-2-Oxo-1,2-Dihydro-Spiro[Indole-3,3'-Pyrrolidine]-5'-Carboxylic Acid Dimethylamide (KE-25)

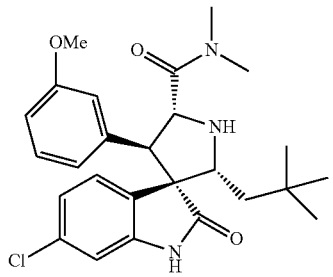 [SMILES: COc1cccc([C@H]2[C@H](C(=O)N(C)C)N[C@H](CC(C)(C)C)[C@]23C(=O)Nc2cc(Cl)ccc23)c1]

$[\alpha]^{25}$D 46.9 (c, 0.4 CHCl$_3$); $^1$H NMR (300 MHz, CDCl$_3$), δ 7.87 (br, 1H), 7.34 (d, J=8.02 Hz, 1H), 7.12~6.93 (m, 2H), 6.74~6.64 (m, 4H), 4.87 (d, J=8.60 Hz, 1H), 4.34 (d, J=8.55 Hz, 1H), 3.79 (d, J=9.09 Hz, 1H), 3.63 (s, 3H), 2.97 (s, 3H), 2.96 (s, 3H), 1.68 (br, 1H), 1.37~1.27 (m, 1H), 0.92~0.88 (m, 1H), 0.84 (s, 9H); $^{13}$C NMR (75 MHz, CDCl$_3$), δ 178.33, 173.23, 159.20, 141.99, 137.60, 133.54, 129.22, 127.24, 123.59, 122.63, 120.63, 114.03, 112.75, 110.15; EI/MS, 470 (M$^+$+1); HRMS C$_{26}$H$_{33}$ClN$_3$O$_3$ ([M+H]$^+$) required 470.2210. found 470.2222.

Example 33

(2'R,3S,4'R,5'R) 6-Chloro-4'-(3-Chloro-Phenyl)-2-Oxo-2'-Pentyl-1,2-Dihydro-Spiro[Indole-3,3'-Pyrrolidine]-5'-Carboxylic Acid Dimethylamide (KE-19)

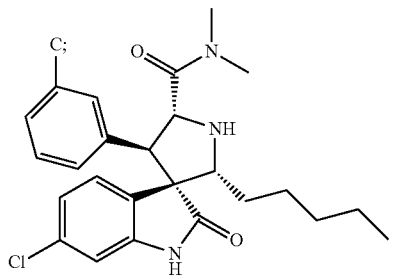

$[\alpha]^{25}{}_D$ 33.0 (c, 0.3 CHCl$_3$); $^1$H NMR (300 MHz, CDCl$_3$), δ 8.23 (br, 1H), 7.23~6.99 (m, 4H), 6.82 (d, J=1.59 Hz, 1H), 6.76 (dd, J=1.92, 7.86 Hz, 1H), 6.48 (d, J=8.10 Hz, 1H), 4.61 (d, J=7.81 Hz, 1H), 3.99 (d, J=7.80 Hz, 1H), 3.51 (dd, J=9.35, 9.49 Hz, 1H), 2.98 (s, 3H), 2.83 (s, 3H), 1.66~1.54 (m, 1H), 1.48~1.42 (m, 1H), 1.26~1.15 (m, 6H), 0.80 (t, J=6.81 Hz, 3H); $^{13}$C NMR (75 MHz, CDCl$_3$), δ 180.13, 170.17, 140.31, 134.43, 133.65, 129.81, 128.71, 127.73, 127.19, 126.95, 125.88, 121.91, 110.06, 70.93, 63.88, 63.42, 59.71, 37.22, 36.22, 31.67, 29.82, 27.25, 22.39, 13.89; EI/MS, 474 (M$^+$+1).

Example 34

(2'R,3S,4'R,5'R)-Butyl-6-Chloro-4'-(3-Chloro-Phenyl)-2-Oxo-1,2-Dihydro-Spiro[Indole-3,3'-Pyrrolidine]-5'-Carboxylic Acid Dimethylamide (KE-18)

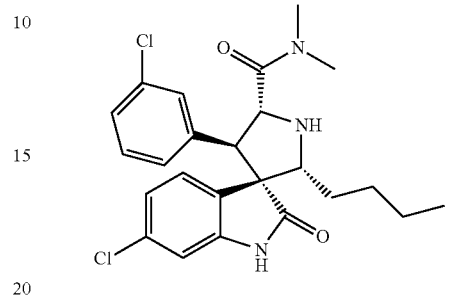

$[\alpha]^{25}$D 20.0 (c, 0.3 CHCl$_3$); $^1$H NMR (300 MHz, CDCl$_3$), δ 8.03 (br, 1H), 7.24~6.88 (m, 4H), 6.78 (s, 1H), 6.76 (dd, J=1.90 Hz, 8.08 Hz, 1H), 6.48 (d, J=8.10 Hz, 1H), 4.62 (d, J=7.83 Hz, 1H), 3.99 (d, J=7.83 Hz, 1H), 3.81 (dd, J=9.19, 9.51 Hz, 1H), 2.94 (s, 3H), 2.84 (s, 3H), 1.68~1.52 (m, 1H), 1.45~1.33 (m, 1H), 1.31~1.18 (m, 4H), 0.75 (t, J=6.891 Hz, 3H); $^{13}$C NMR (75 MHz, CDCl$_3$), δ 180.30, 170.12, 141.93, 140.29, 134.43, 133.66, 129.81, 128.72, 127.74, 127.17, 126.94, 125.90, 121.93, 110.04, 70.58, 63.80, 63.37, 59.68, 37.36, 36.22, 31.57, 29.68, 22.58, 13.82; EI/MS, 460 (M$^+$+1).

Example 35

(2'R,3S,4'R,5'R) 6,7-Dichloro-2'-ISOBUTYL-2-Oxo-4'-Phenyl-1,2-Dihydro-Spiro[Indole-3,3'-Pyrrolidine]-5'-Carboxylic Acid Dimethylamide (KE-11)

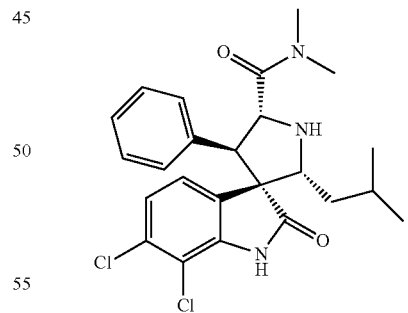

$[\alpha]^{25}{}_D$ 55.7 (c, 0.6 CHCl$_3$); $^1$H NMR (300 MHz, CDCl$_3$), δ 7.83 (br, 1H), 7.28~7.15 (m, 5H), 6.75 (d, J=8.15 Hz, 1H), 6.19 (d, J=8.15 Hz, 1H), 4.61 (d, J=6.97 Hz, 1H), 3.93 (d, J=6.97 Hz, 1H), 3.60~3.50 (m, 1H), 2.94 (s, 3H), 2.74 (s, 3H), 1.80~1.55 (m, 2H), 0.90~0.85 (m, 1H), 0.85 (d, J=6.80 Hz, 3H), 0.78 (d, J=6.53 Hz, 3H); $^{13}$C NMR (75 MHz, CDCl$_3$), δ 179.16, 170.50, 140.27, 138.57, 131.44, 128.77, 128.47, 127.98, 127.74, 123.62, 122.90, 113.17, 68.92, 66.92, 65.21, 60.33, 38.51, 36.22, 35.30, 25.89, 23.53, 21.09.

Example 36

(2'R,3S,4'R,5'R) 6-Chloro-4'-(3-Chloro-Phenyl)-2-Oxo-2'-(2,2-Dimethylpropyl)-1,2-Dihydro-Spiro[Indole-3,3'-Pyrrolidine]-5'-Carboxylic Acid Dimethylamide (KE-17)

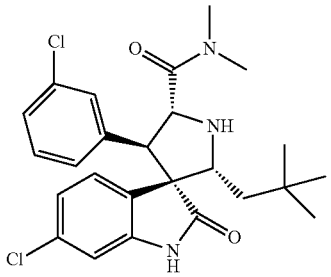 [SMILES: CN(C)C(=O)[C@@H]1N[C@H](CC(C)(C)C)[C@]2(C(=O)Nc3cc(Cl)ccc32)[C@H]1c1cccc(Cl)c1]

$[\alpha]^{25}_D$ 60.9 (c, 0.4 CHCl$_3$); $^1$H NMR (300 MHz, CDCl$_3$), δ 9.36 (br, 1H), 7.35~6.97 (m, 4H), 6.90 (s, 1H), 6.69 (d, J=8.10 Hz, 1H), 6.38 (d, J=8.11 Hz, 1H), 4.54 (d, J=47.41 Hz, 1H), 4.00 (d, J=7.39 Hz, 1H), 3.50 (d, J=9.41 Hz, 1H), 3.17 (br, 1H), 2.97 (s, 3H), 2.91 (s, 3H), 1.51~1.42 (m, 1H), 0.91~0.83 (m, 1H), 0.82 (s, 9H); $^{13}$C NMR (75 MHz, CDCl$_3$), δ 181.37, 170.16, 142.63, 141.05, 134.33, 133.50, 129.78, 128.64, 128.08, 127.52, 127.04, 126.54, 125.65, 121.65, 110.41, 68.13, 65.22, 64.41, 58.08, 43.10, 37.21, 36.19, 30.01, 29.79; EI/MS, 474 (M$^+$+1); HRMS C$_{25}$H$_{30}$Cl$_2$N$_3$O$_2$ ([M+H]$^+$) required 474.1715. found 474.1713.

Example 37

(2'R,3S,4'R,5'R) 6-Chloro-4'-(4-Chloro-Phenyl)-2-Oxo-2'-(2,2-Dimethylpropyl)-1,2-Dihydro-Spiro[Indole-3,3'-Pyrrolidine]-5'-Carboxylic Acid Dimethylamide (KE-31)

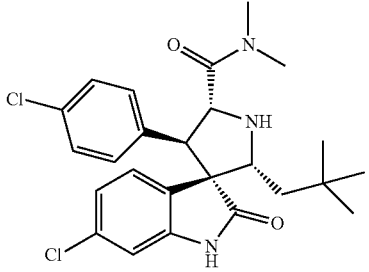 [SMILES: CN(C)C(=O)[C@@H]1N[C@H](CC(C)(C)C)[C@]2(C(=O)Nc3cc(Cl)ccc32)[C@H]1c1ccc(Cl)cc1]

EI/MS, 474 (M$^+$+1); HRMS C$_{25}$H$_{30}$Cl$_2$N$_3$O$_2$ ([M+H]$^+$) required 474.1715. found 474.1703.

Example 38

(2'R,3S,4'R,5'R) 2'-Isobutyl-2-Oxo-4'-Phenyl-1,2-Dihydro-Spiro[Indole-3,3'-Pyrrolidine]-5'-Carboxylic Acid Dimethylamide (KE-8)

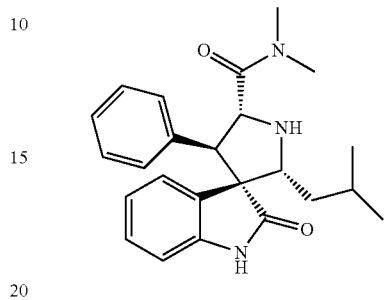

$^1$H NMR (300 MHz, CDCl$_3$), δ 9.13 (br, 1H), 7.28~6.98 (m, 6H), 6.81 (d, J=8.25 Hz, 1H), 6.68 (t, J=7.66 Hz, 1H), 6.50 (d, J=7.41 Hz, 1H), 4.69 (d, J=7.47 Hz, 1H), 3.96 (d, J=7.43 Hz, 1H), 3.65~3.60 (m, 1H), 3.58 (br, 1H), 2.95 (s, 3H), 2.83 (s, 3H), 1.67~1.56 (m, 2H), 0.98~0.85 (m, 1H), 0.75 (d, J=6.94 Hz, 3H), 0.73 (d, J=6.90 Hz, 3H); $^{13}$C NMR (75 MHz, CDCl$_3$), δ 181.18, 170.84, 141.27, 138.59, 128.80, 128.33, 127.70, 127.51, 127.24, 124.90, 121.50, 109.39, 68.32, 64.11, 63.93, 60.04, 38.66, 37.11, 36.13, 25.70, 23.40, 21.68.

Example 39

(2'R,3S,4'R, 5'R) 6-Chloro-4'-(3-Bromo-Phenyl)-2'-(2,2-Dimethyl-Propyl)-2-Oxo-1,2-Dihydro-Spiro[Indole-3,3'-Pyrrolidine]-5'-Carboxylic Acid (3-Morpholin-4-yl-Propyl)-Amide (KE-40)

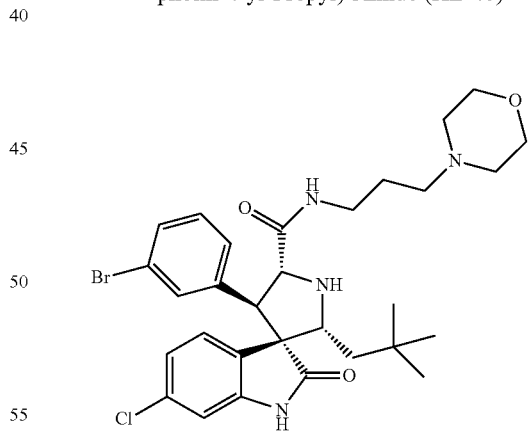

$^1$H NMR (300 MHz, CDCl$_3$), δ 8.45 (br, 1H), 7.40~7.20 (m, 2H), 7.15~7.00 (m, 2H), 6.80 (s, 1H), 6.72 (d, J=8.34 Hz, 1H), 6.30~6.25 (m, 1H), 4.29 (d, J=3.92 Hz, 1H), 3.85 (d, J=4.04 Hz, 1H), 3.80~3.57 (m, 4H), 3.56 (d, J=8.44 Hz, 1H), 3.40~3.20 (m, 4H), 2.55~2.35 (m, 6H), 1.70~1.60 (m, 2H), 1.55~1.48 (m, 1H), 0.98~0.83 (m, 1H), 0.83 (s, 9H); $^{13}$C NMR (75 MHz, CDCl$_3$), δ 180.44, 171.61, 142.14, 141.12, 133.79, 131.58, 130.90, 129.98, 127.50, 126.91, 126.04, 122.77, 121.91, 110.18, 67.25, 66.83, 66.75, 66.11, 63.38, 57.06, 26.78, 53.54, 43.73, 38.24, 30.15, 29.95, 29.82.

Example 40

(2'R,3S,4'R,5'R) 6-Chloro-4'-(3-Chloro-Phenyl)-2'-Cyclohexylmethyl-2-Oxo-1,2-Dihydro-Spiro[Indole-3,3'-Pyrrolidine]-5'-Carboxylic Acid Dimethylamide (KE-41)

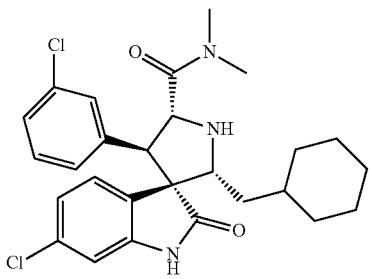 [SMILES: CN(C)C(=O)[C@@H]1N[C@H](CC2CCCCC2)[C@]2(C(=O)Nc3cc(Cl)ccc32)[C@H]1c1cccc(Cl)c1]

$^1$H NMR (300 MHz, CDCl$_3$), δ 8.98 (br, 1H), 7.34~7.00 (m, 4H), 6.87 (d, J=1.50 Hz, 1H), 6.73 (dd, J=1.60, 8.08 Hz, 1H), 6.43 (d, J=8.09 Hz, 1H), 4.59 (d, J=7.56 Hz, 1H), 3.98 (d, J=7.54 Hz, 1H), 3.65~3.55 (m, 1H), 2.98 (s, 3H), 2.86 (s, 3H), 1.68~1.30 (m, 7H), 1.11~0.85 (m, 4H), 0.78 (t, J=10.41 Hz, 1H), 0.66~0.55 (m, 1H); $^{13}$C NMR (75 MHz, CDCl$_3$), δ 180.80, 170.29, 142.39, 140.63, 134.41, 133.57, 129.82, 128.72, 127.67, 126.99, 126.85, 125.66, 121.76, 110.28, 68.38, 64.36, 63.67, 60.39, 59.39, 37.22, 36.23, 35.22, 34.17, 32.52, 26.37, 26.15, 25.96.

Example 41

(2'R,3S,4'R,5'R) 6-Chloro-4'-(3-Bromo-Phenyl)-2'-(2,2-Dimethyl-Propyl)-2-Oxo-1,2-Dihydro-Spiro[Indole-3,3'-Pyrrolidine]-5'-Carboxylic Acid (2-Morpholin-4-yl-Ethyl)-Amide (KE-43)

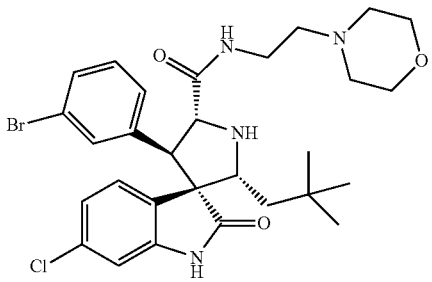 [SMILES: CC(C)(C)C[C@H]1N[C@@H](C(=O)NCCN2CCOCC2)[C@H](c2cccc(Br)c2)[C@@]12C(=O)Nc1cc(Cl)ccc12]

$^1$H NMR (300 MHz, CDCl$_3$), δ 8.44 (br, 1H), 7.29 (d, J=7.99 Hz, 1H), 7.26 (s, 1H), 7.11~6.96 (m, 3H), 6.81 (s, 1H), 6.72 (d, J=8.08 Hz, 1H), 6.33 (d, J=8.07 Hz, 1H), 4.32 (d, J=7.15 Hz, 1H), 3.86 (d, J=7.13 Hz, 1H), 3.65~3.50 (m, 3H), 3.56 (d, J=9.41 Hz, 1H), 3.40~3.35 (m, 2H), 2.50~2.40 (m, 7H), 1.53 (dd, J=9.99, 14.06 Hz, 1H), 1.28 (br, 1H), 0.99~0.92 (m, 1H), 0.85 (s, 9H); $^{13}$C NMR (75 MHz, CDCl$_3$), δ 180.19, 171.65, 142.09, 141.11, 133.78, 131.44, 130.49, 130.00, 127.49, 126.47, 125.87, 122.58, 121.91, 110.18, 67.11, 66.94, 66.26, 63.59, 57.05, 56.76, 53.18, 43.85, 35.59, 30.21, 29.88.

Example 42

(2'R,3S,4'R,5'R) 6-Chloro-4'-(3-Chloro-5-Fluoro-Phenyl)-2'-(2,2-Dimethyl-Propyl)-2-Oxo-1,2-Dihydro-Spiro[Indole-3,3'-Pyrrolidine]-5'-Carboxylic Acid Dimethylamide (KE-47)

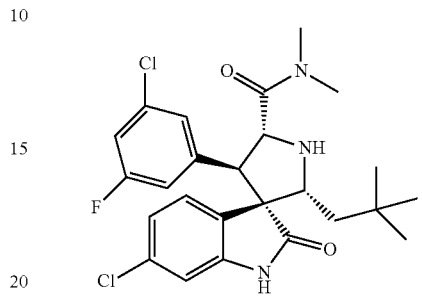

[α]$^{25}_D$ 101.5 (c 1.1 CHCl$_3$); $^1$H NMR (300 MHz, CDCl$_3$), δ 8.56 (br, 1H), 6.95~6.85 (m, 3H), 6.83~6.74 (m, 2H), 6.50 (d, J=8.10 Hz, 1H), 4.47 (d, J=7.97 Hz, 1H), 4.12 (d, J=7.81 Hz, 1H), 3.48 (d, J=9.83 Hz, 1H), 3.10 (s, 3H), 2.97 (s, 3H), 1.46 (dd, J=6.98, 14.11 Hz, 1H), 1.05~0.98 (m, 1H), 0.84 (s, 9H); $^{13}$C NMR (75 MHz, CDCl$_3$), δ 180.87, 169.59, 142.72, 142.62, 142.29, 135.23, 133.82, 126.57, 125.61, 124.69, 122.01, 115.39, 114.37, 110.43, 68.66, 65.25, 64.22, 57.94, 43.19, 37.28, 36.18, 30.17, 29.84; C$_{25}$H$_{28}$Cl$_2$FN$_3$O$_2$ requires C, 60.98; H, 5.73; N, 8.53. Found C, 61.12; H, 6.14; N, 8.00.

Example 43

(2'R,3S,4'R,5'R) 6-Chloro-4'-(4-Chloro-3-Fluoro-Phenyl)-2'-(2,2-Dimethyl-Propyl)-2-Oxo-1,2-Dihydro-Spiro[Indole-3,3'-Pyrrolidine]-5'-Carboxylic Acid Dimethylamide (KE-46)

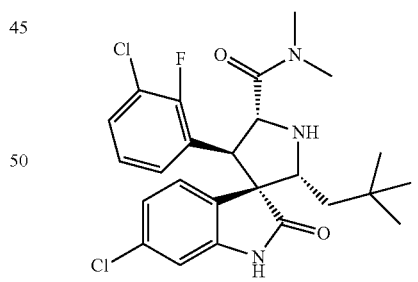

[α]$^{25}_D$ 58.0 (c 0.75, CHCl$_3$); $^1$H NMR (300 MHz, CDCl$_3$), δ 9.25 (br, 1H), 7.28~7.20 (m, 2H), 7.04 (d, J=7.67 Hz, 1H), 7.90 (s, 1H), 6.69 (d, J=7.94 Hz, 1H), 6.41 (d, j=2.82 Hz, 1H), 4.65 (d, J=7.60 Hz, 1H), 4.32 (d, J=7.54 Hz, 1H), 3.48 (d, J=9.44 Hz, 1H), 3.02 (s, 3H), 2.99 (s, 3H), 1.50~1.42 (m, 1H), 1.03~0.95 (m, 1H), 0.82 (s, 9H); $^{13}$C NMR (75 MHz, CDCl$_3$), δ 181.46, 169.84, 157.92, 142.78, 133.61, 129.63, 128.26, 127.46, 126.70, 124.79, 124.54, 121.67, 110.47, 68.26, 63.73, 52.27, 42.85, 37.02, 36.13, 30.08, 29.76; C$_{25}$H$_{28}$Cl$_2$FN$_3$O$_2$+H$_2$O requires C, 58.83; H, 5.92; N, 8.23. Found C, 59.09; H, 5058; N, 8.16.

Example 44

(2'R,3S,4'R,5'R) 6-Chloro-4'-(3-Chloro-4-Fluoro-Phenyl)-2'-(2,2-Dimethyl-Propyl)-2-Oxo-1,2-Dihydro-Spiro[Indole-3,3'-Pyrrolidine]-5'-Carboxylic Acid Dimethylamide (KE-45)

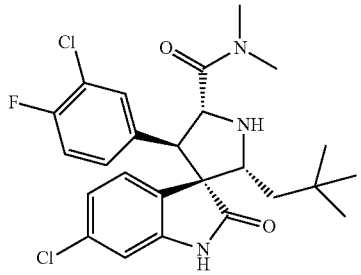 [SMILES: CN(C)C(=O)[C@@H]1N[C@H](CC(C)(C)C)[C@]2(C(=O)Nc3cc(Cl)ccc32)[C@H]1c1ccc(F)c(Cl)c1]

$[\alpha]^{25}_D$ 97.4 (c 1, CHCl$_3$); $^1$H NMR (300 MHz, CDCl$_3$), δ 9.10 (br, 1H), 7.18 (d, J=6.16 Hz, 1H), 7.01~6.90 (m, 2H), 6.89 (d, J=1.75 Hz, 1H), 6.75 (dd, J=1.80, 8.10 Hz, 1H), 6.45 (d, J=8.11 Hz, 1H), 4.47 (d, J=7.73 Hz, 1H), 4.06 (d, J=7.84 Hz, 1H), 3.49 (d, J=9.62 Hz, 1H), 2.98 (s, 6H), 1.48 (dd, J=9.96, 14.18 Hz, 1H), 1.03~0.89 (m, 1H), 0.83 (s, 9H); $^{13}$C NMR (75 MHz, CDCl$_3$), δ 181.25, 169.85, 158.69, 142.49, 135.97, 155.65, 130.51, 128.50, 126.62, 125.62, 121.85, 121.08, 116.75, 110.50, 68.37, 65.47, 64.27, 57.54, 43.13, 37.26, 36.17, 30.12, 29.80; C$_{25}$H$_{28}$Cl$_2$FN$_3$O$_2$ requires C, 60.98; H, 5.73; N, 8.53. Found C, 61.05; H, 6.26; N, 7.97.

Example 45

(2'R,3S,4'R,5'R) 6-Chloro-4'-(3-Chloro-Phenyl)-2'-(2,2-Dimethyl-Butyl)-2-Oxo-1,2-Dihydro-Spiro[Indole-3,3'-Pyrrolidine]-5'-Carboxylic Acid Dimethylamide (KE-48)

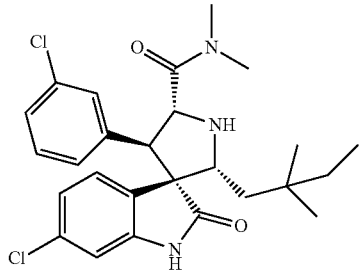 [SMILES: CCC(C)(C)C[C@H]1N[C@@H](C(=O)N(C)C)[C@H](c2cccc(Cl)c2)[C@@]12C(=O)Nc1cc(Cl)ccc12]

$^1$H NMR (300 MHz, CDCl$_3$), δ 8.88 (br, 1H), 7.17~7.14 (m, 3H), 7.05~7.02 (m, 1H), 6.88 (d, J=1.77 Hz, 1H), 6.70 (dd, J=1.83, 8.11 Hz, 1H), 6.37 (d, J=8.13 Hz, 1H), 4.53 (d, J=7.38 Hz, 1H), 4.01 (d, J=7.41 Hz, 1H), 3.49 (d, J=9.41 Hz, 1H), 2.98 (s, 3H), 2.92 (s, 3H), 1.45 (dd, J=9.87, 14.17 Hz, 1H), 1.28 (br, 1H), 1.20~1.16 (m, 2H), 0.92~0.87 (m, 1H), 0.78 (s, 6H), 0.62 (t, J=7.51 Hz, 3H); $^{13}$C NMR (75 MHz, CDCl$_3$), δ 181.18, 170.13, 142.46, 141.13, 134.39, 133.55, 129.82, 128.68, 127.57, 127.08, 126.54, 125.78, 121.74, 110.32, 67.90, 65.36, 64.47, 58.05, 40.79, 37.22, 36.20, 34.15, 32.57, 27.15, 26.91, 8.22.

Example 46

(2'R,3S,4'R,5'R) 6-Chloro-4'-(6-Bromo-Pyridin-2-yl)-2'-(2,2-Dimethyl-Propyl)-2-Oxo-1,2-Dihydro-Spiro[Indole-3,3'-Pyrrolidine]-5'-Carboxylic Acid Dimethylamide (KE-50)

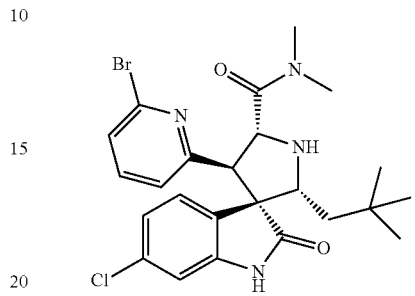

$^1$H NMR (300 MHz, CDCl$_3$), δ 8.37 (br, 1H), 7.25~7.23 (m, 2H), 6.81~6.77 (m, 4H), 5.04 (d, J=8.34 Hz, 1H), 4.17 (d, J=8.41 Hz, 1H), 3.67 (d, J=9.17 Hz, 1H), 3.09 (s, 3H), 2.96 (s, 3H), 1.73 (br, 1H), 1.50 (dd, J=9.99, 14.10 Hz, 1H), 0.99~0.90 (m, 1H), 0.87 (s, 9H); $^{13}$C NMR (75 MHz, CDCl$_3$), δ 181.25, 170.60, 159.68, 141.96, 141.14, 138.80, 133.38, 127.06, 126.98, 126.36, 123.62, 121.98, 109.88, 69.70, 64.79, 64.11, 60.08, 42.97, 37.32, 35.92, 30.19, 29.84.

Example 47

1'-Methyl-2'-(2-Methyl-Propenyl)-4'-Phenyl-1H-Spiro[Indole-3,3'-Pyrrolidin]-2-One (KE-13)

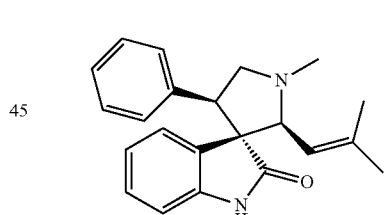

A mixture of 3-E-3-benzylidene-1,3-dihydro-indol-2-one (10.0 mmol), N-methyl-glycine (14 mmol) and 3-methyl-but-2-enal (14 mmol) in 100 mL toluene was refluxed for 6 hours. The solvent was removed and the residue was purified on silica gel column to yield the product.

$^1$H NMR (300 MHz, CDCl$_3$), δ 8.06 (br, 1H), 7.28 (d, J=8.01 Hz, 1H), 7.10~6.95 (m, 4H), 6.74~6.67 (m, 4H), 5.72 (s, 1H), 4.15 (m, 1H), 3.48 (dd, J=5.51, 12.01 Hz, 1H), 2.71~2.61 (m, 1H), 2.32 (dd, J=5.31, 18.54 Hz, 1H), 2.05 (s, 3H), 1.84 (s, 6H); $^{13}$C NMR (75 MHz, CDCl$_3$), δ 180.61, 143.07, 138.56, 135.89, 133.75, 128.14, 127.78, 127.55, 127.32, 127.10, 121.45, 120.85, 110.33, 67.38, 57.30, 47.31, 43.06, 34.77, 23.09, 14.19.

Example 48

6-Chloro-1'-Methyl-2'-(2-Methyl-Propenyl)-4'-Phenyl-1H-Spiro[Indole-3,3'-Pyrrolidin]-2-One (KE-2)

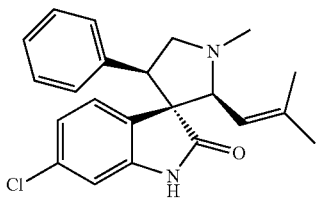 [SMILES: CC(C)=C[C@@H]1N(C)C[C@H](c2ccccc2)[C@@]12C(=O)Nc1cc(Cl)ccc12]

Using a method similar to that in Example 47, this compound was synthesized.

¹H NMR (300 MHz, CDCl₃), δ 7.56 (br, 1H), 7.28 (d, J=8.04 Hz, 2H), 7.13~7.02 (m, 4H), 6.72~6.67 (m, 3H), 5.73 (s, 1H), 3.49 (dd, J=5.46, 12.21 Hz, 1H), 2.65 (dd, J=12.64, 17.30 Hz, 1H), 2.32 (dd, J=3.21, 18.31 Hz, 1H), 2.08 (s, 6H), 1.91 (s, 3H); ¹³C NMR (75 MHz, CDCl₃), δ 180.21, 142.86, 138.57, 135.89, 133.75, 128.17, 127.81, 127.64, 127.33, 127.11, 121.52, 120.75, 110.20, 67.40, 57.33, 47.33, 43.15, 34.74, 23.12.

Example 49

1'-Methyl-2'-(2-Methyl-Propenyl)-2-Oxo-1,2-Dihydro-Spiro[Indole-3,3'-Pyrrolidine]-4'-Carboxylic Acid Tert-Butyl Ester (KE-3)

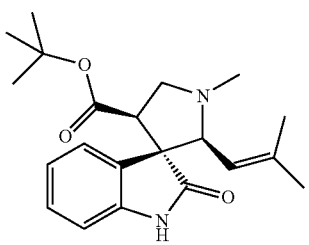 [SMILES: CC(C)=C[C@@H]1N(C)C[C@H](C(=O)OC(C)(C)C)[C@@]12C(=O)Nc1ccccc12]

Using a method similar to that in Example 47, this compound was synthesized.

¹HNMR (300 MHz, CDCl₃), δ 8.53 (br, 1H), 7.42 (d, J=7.40 Hz, 1H), 7.20 (td, J=1.27, 7.69 Hz, 1H), 6.99 (td, J=0.97, 7.53 Hz, 1H), 6.86 (d, J=7.66 Hz, 1H), 4.42 (dt, J=1.33, 9.32 Hz, 1H), 3.85 (dd, J=5.51, 9.72 Hz, 1H), 3.66 (dd, J=5.49, 10.80 Hz, 1H), 3.58 (d, J=9.32 Hz, 1H), 2.70 (t, J=9.87 Hz, 1H), 2.28 (s, 3H), 1.63 (d, J=1.23 Hz, 3H), 1.49 (d, J=1.20 Hz, 3H), 0.95 (s, 9H); ¹³CNMR (75 MHz, CDCl₃), δ 179.44, 169.54, 141.21, 138.48, 129.20, 127.89, 126.16, 122.15, 120.52, 108.86, 80.80, 71.64, 60.95, 54.48, 49.94, 39.97, 27.17, 26.05, 18.48.

Example 50

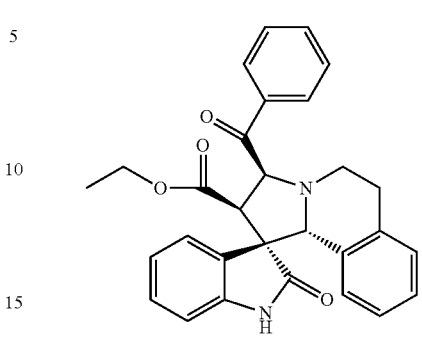

To a solution of (2-oxo-1,2-dihydro-indol-3-ylidene)-acetic acid ethyl ester and the complex formed by 2-bromo-1-phenyl-ethanone and 3,4-dihydro-isoquinoline (a salt) in CH₂Cl₂, Et₃N was added. The resulting solution was stirred at room temperature overnight. The solvent was removed and the residue was purified on a silica gel column to yield the product.

¹H NMR (300 MHz, CDCl₃), δ 8.13 (br, 1H), 8.10 (d, J=1.47 Hz, 1H), 8.07 (d, J=7.58 Hz, 1H), 7.63~7.59 (m, 1H), 7.55~7.49 (m, 2H), 7.44 (s, 1H), 7.32 (d, J=7.62 Hz, 1H), 7.21~7.16 (m, 1H), 7.08~7.05 (m, 1H), 6.86~6.80 (m, 2H), 6.16 (d, J=7.65 Hz, 1H), 5.42 (d, J=7.38 Hz, 1H), 5.19 (s, 1H), 4.27 (d, J=7.35 Hz, 1H), 3.89~3.76 (m, 3H), 3.22~3.15 (m, 1H), 2.96 (d, J=5.14 Hz, 1H), 2.95 (d, J=5.83 Hz, 1H), 0.76 (d, J=7.15 Hz, 3H); ¹³C NMR (75 MHz, CDCl₃), δ 197.64, 180.02, 169.25, 140.69, 137.00, 134.62, 133.07, 132.50, 130.99, 128.57, 128.50, 128.33, 126.91, 126.31, 125.65, 124.68, 123.19, 109.10, 71.09, 70.71, 63.02, 60.55, 55.12, 46.76, 28.97, 26.95, 13.49.

Example 51

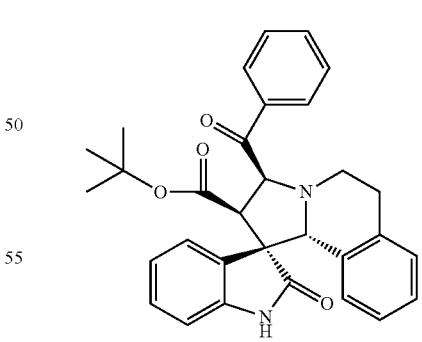

Using a method similar to that in Example 50, this compound was synthesized.

¹H NMR (300 MHz, CDCl₃), δ 8.25 (br, 1H), 7.51 (d, J=7.26 Hz, 2H), 735~7.22 (m, 3H), 7.01~6.95 (m, 5H), 6.95~6.89 (m, 3H), 5.15 (d, J=3.90 Hz, 1H), 4.18 (dd, J=4.15, 9.09 Hz, 1H), 3.93 (d, J=9.10 Hz, 1H), 3.57 (s, 1H), 3.37~3.30 (m, 1H), 3.18~3.15 (m, 1H), 2.90~2.80 (m, 2H), 0.78 (s, 9H).

Example 52

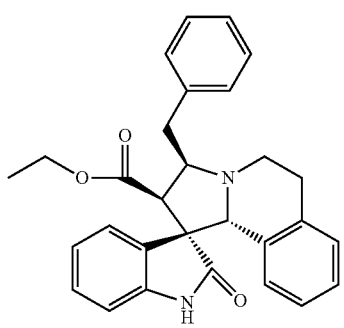 [SMILES: CCOC(=O)[C@H]1[C@@H](Cc2ccccc2)N2CCc3ccccc3[C@@H]2[C@]12C(=O)Nc1ccccc12]

This compound was prepared by hydrogenation of the compound of example 50.

$^1$H NMR (300 MHz, CDCl$_3$), δ 7.93 (br, 1H), 7.57~7.42 (m, 3H), 7.35~7.23 (m, 4H), 7.11~6.93 (m, 3H), 6.76~6.67 (m, 2H), 6.08 (d, J=7.70 Hz, 1H), 5.41 (s, 1H), 5.24 (d, J=5.83 Hz, 1H), 4.60 (t, J=5.89 Hz, 1H), 4.10~4.03 (m, 1H), 4.04 (q, J=7.14 Hz, 2H), 3.24~3.20 (m, 1H), 3.12~3.03 (m, 1H), 2.98 (d, J=5.88 Hz, 1H), 2.89~2.81 (m, 1H), 2.55~2.50 (m, 1H), 0.93 (t, J=6.40 Hz, 3H); $^{13}$C NMR (75 MHz, CDCl$_3$), δ 178.51, 170.99, 141.75, 137.37, 134.08, 128.96, 128.29, 128.15, 127.54, 127.17, 126.34, 125.80, 125.65, 124.98, 124.43, 122.60, 109.65, 70.84, 69.22, 67.95, 61.06, 60.60, 44.58, 26.92, 22.64, 13.74.

Example 53

KE-6

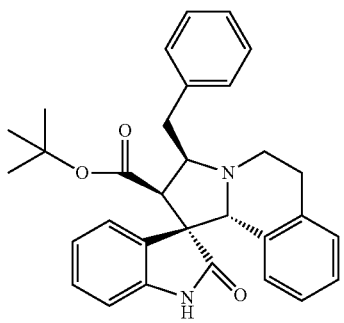 [SMILES: CC(C)(C)OC(=O)[C@H]1[C@@H](Cc2ccccc2)N2CCc3ccccc3[C@@H]2[C@]12C(=O)Nc1ccccc12]

This compound was prepared by the hydrogenation of example 51.

$^1$H NMR (300 MHz, MeOH-d$_6$), δ 7.65~7.42 (m, 6H), 7.23~7.18 (m, 3H), 6.96~6.93 (m, 2H), 6.23 (d, J=7.85 Hz, 1H), 6.00 (s, 1H), 5.42 (d, J=6.62 Hz, 1H), 5.28 (t, J=6.16 Hz, 1H), 3.59~2.83 (m, 6H), 1.46 (s, 9H).

Example 54

(2'R,3S,4'R,5'R) 6-Chloro-4'-Cyclohexyl-2'-(2,2-Dimethyl-Propyl)-2-Oxo-1,2-Dihydro-Spiro[Indole-3,3'-Pyrrolidine]-5'-Carboxylic Acid Dimethylamide (G-51)

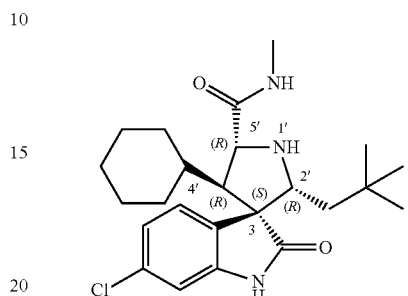

$^1$H NMR (300 MHz, CDCl$_3$), δ 9.05 (s, 1H), 7.26-6.79 (m, 4H), 3.72 (d, J=8.0 Hz, 1H), 3.26 (d, J=8.3 Hz, 1H), 3.11-2.95 (m, 2H), 2.89 (d, J=4.5 Hz, 3H), 2.50 (t, J=3.3 Hz, 1H), 2.29 (br, 1H), 1.93 (s, 1H), 1.70 (s, 1H), 1.43-1.21 (m, 5H), 1.19-0.85 (m, 3H), 0.74 (s, 9H); $^{13}$C NMR (75 MHz, CDCl$_3$), δ 182.36, 176.77, 142.27, 133.62, 128.30, 125.29, 122.09, 110.62, 67.30, 67.14, 61.70, 57.76, 43.20, 38.51, 34.61, 32.77, 31.54, 30.64, 30.02, 29.71, 26.29, 26.02, 25.69.

Example 55

(2'R,3S,4'R,5'R) 6-Chloro-4'-Cyclopentyl-2'-(2,2-Dimethyl-Propyl)-2-Oxo-1,2-Dihydro-Spiro[Indole-3,3'-Pyrrolidine]-5'-Carboxylic Acid Dimethylamide (G-52)

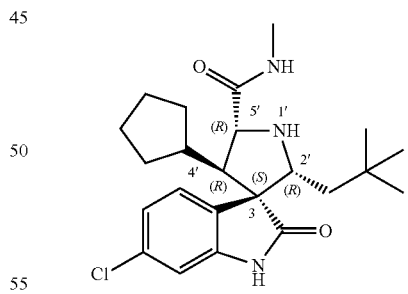

$^1$H NMR (300 MHz, CDCl$_3$), δ 9.12 (s, 1H), 7.26-6.97 (m, 4H), 4.13 (d, J=7.1 Hz, 1H), 3.68 (d, J=7.7 Hz, 1H), 3.11-2.95 (m, 2H), 2.97 (s, 3H), 2.62 (t, J=2.2 Hz, 1H), 1.92-1.86 (m, 2H), 1.61-1.08 (m, 7H), 0.75 (s, 9H); $^{13}$C NMR (75 MHz, CDCl$_3$), δ 182.52, 174.10, 142.48, 133.71, 128.60, 125.65, 122.26, 110.57, 68.98, 66.47, 61.94, 59.09, 43.50, 41.58, 31.59, 31.45, 30.84, 30.06, 26.29, 25.48, 24.63.

Example 56

(2'R,3S,4'R,5'R) 6-Chloro-4'-Cyclohexylmethyl-2'-(2,2-Dimethyl-Propyl)-2-Oxo-1,2-Dihydro-Spiro[Indole-3,3'-Pyrrolidine]-5'-Carboxylic Acid Dimethylamide (G-53)

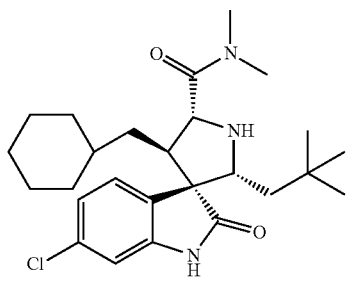 [SMILES: CN(C)C(=O)[C@@H]1N[C@H](CC(C)(C)C)[C@]2(C(=O)Nc3cc(Cl)ccc32)[C@H]1CC1CCCCC1]

$^1$H NMR (300 MHz, CDCl$_3$), δ 9.33 (s, 1H), 7.10-6.85 (m, 4H), 3.76 (s, 1H), 3.31-2.95 (m, 10H), 2.56 (s, 1H), 1.83-1.54 (m, 6H), 1.31-1.09 (m, 6H), 0.85 (s, 9H); $^{13}$C NMR (75 MHz, CDCl$_3$), δ 182.80, 170.32, 142.54, 133.86, 129.02, 121.86, 116.72, 110.48, 76.60, 63.54, 69.48, 51.01, 43.29, 37.86, 37.53, 35.96, 35.50, 32.86, 32.13, 30.09, 29.82, 26.36, 26.12.

Example 58

(2'R,3S,4'R,5'R) 6-Chloro-2'-(2,2-Dimethyl-PROPYL)-2-Oxo-4'-Thiophen-2-yl-1,2-Dihydro-Spiro[Indole-3,3'-Pyrrolidine]-5'-Carboxylic Acid Dimethylamide (G-57)

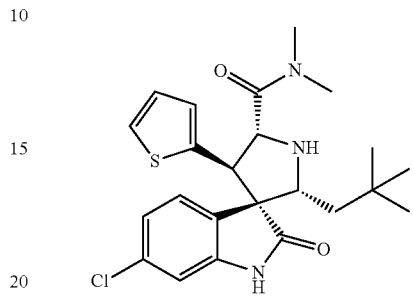

$^1$H NMR (300 MHz, CDCl$_3$), δ 8.38 (s, 1H), 7.10 (d, J=5.0 Hz, 1H), 6.80-6.35 (m, 5H), 4.48 (d, J=7.0 Hz, 1H), 4.27 (d, J=7.3 Hz, 1H), 3.51 (d, J=9.3 Hz, 1H), 2.98 (d, J=7.8 Hz, 6H), 1.52-1.44 (m, 1H), 1.31-1.23 (m, 1H), 0.84 (s, 9H); $^{13}$CNMR (75 MHz, CDCl$_3$), δ 180.64, 169.93, 142.30, 142.09, 133.58, 127.06, 126.73, 126.20, 125.34, 124.30, 121.83, 110.05, 67.69, 67.52, 64.34, 53.28, 43.05, 37.09, 36.21, 31.57, 30.15, 29.82.

Example 57

(2'R,3S,4'R,5'R) 6-Chloro-2'-(2,2-Dimethyl-Propyl)-2-Oxo-4'-Pyridin-2-yl-1,2-Dihydro-Spiro[Indole-3,3'-Pyrrolidine]-5'-Carboxylic Acid Dimethylamide (G-56)

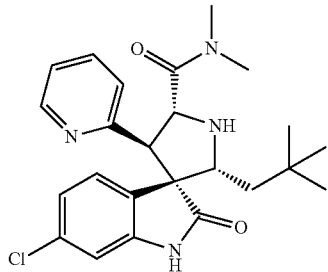 [SMILES: CN(C)C(=O)[C@@H]1N[C@H](CC(C)(C)C)[C@]2(C(=O)Nc3cc(Cl)ccc32)[C@H]1c1ccccn1]

$^1$H NMR (300 MHz, CDCl$_3$), δ 9.13 (s, 1H), 8.61 (t, J=2.2 Hz, 1H), 7.38 (t, J=2.2 Hz, 1H), 7.07-7.03 (m, 1H), 6.86 (d, J=2.1 Hz, 1H), 6.78 (d, J=8.0 Hz, 1H), 6.63-6.60 (m, 1H), 6.50 (d, J=8.0 Hz, 1H), 5.23 (d, J=7.8 Hz, 1H), 4.12 (d, J=8.0 Hz, 1H), 3.51 (d, J=9.3 Hz, 1H), 3.0-2.92 (m, 6H), 1.50-1.32 (m, 1H), 0.88 (m, 1H), 0.82 (s, 9H); $^{13}$C NMR (75 MHz, CDCl$_3$), δ 181.80, 171.13, 158.49, 148.66, 142.33, 136.51, 133.12, 127.04, 126.30, 125.74, 124.29, 122.19, 121.56, 109.97, 68.86, 64.88, 63.77, 59.85, 53.41, 42.76, 37.08, 35.91, 31.55, 30.43.

Example 59

(2'R,3S,4'R,5'R) 4'-(3-Bromo-Phenyl)-2'-(2,2-Dimethyl-Propyl)-2-Oxo-1,2-Dihydro-Spiro[Indole-3,3'-Pyrrolidine]-5'-Carboxylic Acid Dimethylamide (G-58)

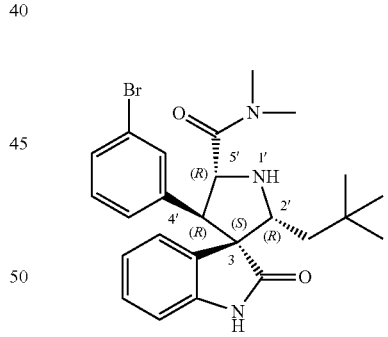

$^1$H NMR (300 MHz, CDCl$_3$), δ 8.75 (br, 1H), 7.30~7.27 (m, 2H), 7.08~7.03 (m, 3H), 6.83 (d, J=7.63 Hz, 1H), 6.74 (dd, J=7.45, 7.49 Hz, 1H), 6.53 (d, J=7.45 Hz, 1H), 4.55 (d, J=7.68 Hz, 1H), 4.02 (d, J=7.67 Hz, 1H), 3.54 (d, J=9.14 Hz, 1H), 3.21 (br, 1H), 2.98 (s, 3H), 2.93 (s, 3H), 1.54~1.46 (m, 1H), 1.03~0.92 (m, 1H), 0.82 (s, 9H); $^{13}$CNMR (75 MHz, CDCl$_3$), δ 161.22, 170.23, 141.42, 141.19, 131.61, 130.22, 129.85, 128.25, 127.75, 127.56, 124.93, 122.40, 121.75, 109.60, 68.09, 65.06, 64.65, 58.32, 43.25, 37.22, 36.14, 30.12, 29.80.

Example 60

(2'R,3S,4'R,5'R) 6-Chloro-2'-(2,2-Dimethyl-Propyl)-4'-(1-Methyl-1H-Pyrrol-2-yl)-2-Oxo-1,2-Dihydro-Spiro[indole-3,3'-Pyrrolidine]-5'-Carboxylic Acid Dimethylamide (G-84)

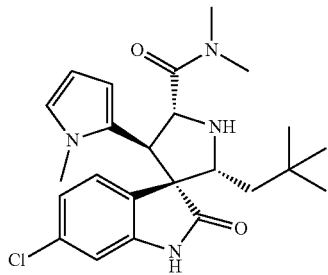 [SMILES: CN(C)C(=O)[C@@H]1N[C@H](CC(C)(C)C)[C@]2(C(=O)Nc3cc(Cl)ccc32)[C@H]1c1cccn1C]

$^1$H NMR (300 MHz, CDCl$_3$): δ 8.33 (s, 1H), 6.88 (s, 1H), 6.71 (d, J=7 Hz, 1H), 6.38-6.08 (m, 4H), 4.56 (d, J=7.0 Hz, 1H), 4.01 (d, J=7.3 Hz, 1H), 3.43 (d, J=9.3 Hz, 1H), 3.14 (s, 3H), 3.05 (s, 3H), 2.90 (s, 3H), 1.41-1.27 (m, 1H), 0.92~0.90 (m, 1H), 0.89 (s, 9H); $^{13}$C NMR (75 MHz, CDCl$_3$): δ 180.62, 170.48, 148.61, 133.57, 130.31, 126.26, 123.71, 122.62, 122.21, 109.66, 107.37, 106.90, 67.50, 65.41, 63.44, 48.36, 42.25, 37.25, 36.23, 34.64, 33.17, 30.09, 29.80.

Example 61

(2'R,3S,4'R,5'R) 6-Chloro-2'-(2,2-Dimethyl-Propyl)-2-Oxo-4'-Pyridin-4-yl-1,2-Dihydro-Spiro[Indole-3,3'-Pyrrolidine]-5'-Carboxylic Acid Dimethylamide (G-83)

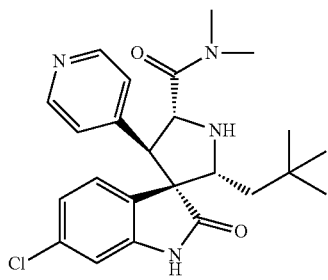 [SMILES: CN(C)C(=O)[C@@H]1N[C@H](CC(C)(C)C)[C@]2(C(=O)Nc3cc(Cl)ccc32)[C@H]1c1ccncc1]

$^1$H NMR (300 MHz, CDCl$_3$): δ 8.91 (s, 1H), 8.39 (d, J=10 Hz, 2H), 7.53 (d, J=7 Hz, 1H), 7.34 (d, J=7 Hz, 1H), 7.08 (d, J=7.1 Hz, 2H), 6.75 (s, 1H), 4.89 (d, J=8.10 Hz, 1H), 4.49 (d, J=8.12 Hz, 1H), 3.75 (d, J=9.32 Hz, 1H), 3.04 (s, 3H), 2.91 (s, 3H), 1.31-1.27 (m, 1H), 0.90~0.86 (m, 1H), 0.85 (s, 9H); $^{13}$C NMR (75 MHz, CDCl$_3$): δ (ppm) 178.60, 172.67, 149.87, 148.85, 142.78, 136.81, 134.41, 126.71, 123.92, 123.80, 123.20, 110.92, 66.75, 66.39, 61.60, 55.46, 43.84, 37.91, 36.72, 30.59, 30.22.

Example 62

(2'R,3S,4'R,5'R) 6-Chloro-2'-(2,2-Dimethyl-Propyl)-2-Oxo-4'-Pyridin-3-yl-1,2-dihydro-Spiro[Indole-3,3'-Pyrrolidine]-5'-Carboxylic Acid Dimethylamide (G-82)

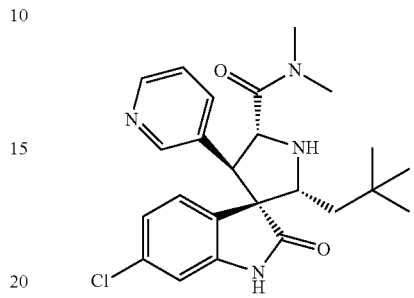

$^1$H NMR (300 MHz, CDCl$_3$): δ 9.08 (s, 1H), 8.45 (d, J=7 Hz, 2H), 7.44-6.42 (m, 5H), 4.58 (d, J=7 Hz, 1H), 4.16 (d, J=8 Hz, 1H), 3.53 (d, J=7.7 Hz, 1H), 2.98 (d, J=6 Hz, 6H), 1.53-1.43 (m, 1H), 0.90~0.85 (m, 1H), 0.84 (s, 9H); $^{13}$C NMR (75 MHz, CDCl$_3$): δ 181.44, 170.26, 150.07, 148.90, 143.03, 136.76, 135.03, 134.09, 127.09, 126.17, 123.83, 122.27, 110.85, 68.98, 65.34, 64.07, 56.55, 43.58, 37.72, 36.60, 31.99, 30.59, 30.25.

Example 63

(2'R,3S,4'R,5'R) 6-Chloro-2'-(2,2-Dimethyl-Propyl)-4'-Furan-3-yl-2-Oxo-1,2-Dihydro-Spiro[Indole-3,3'-Pyrrolidine]-5'-Carboxylic Acid Methylamide (G-81)

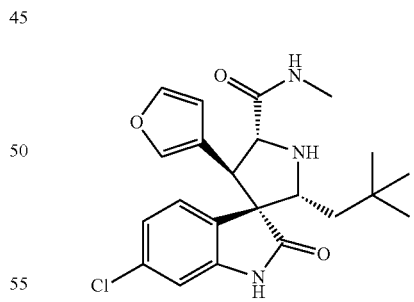

$^1$H NMR (300 MHz, CDCl$_3$): δ 9.01 (s, 1H), 7.30-6.56 (m, 5H), 6.01 (s, 1H), 4.08 (d, J=7.50 Hz, 1H), 3.75 (d, J=7.50 Hz, 1H), 3.42 (d, J=9.00 Hz, 1H), 2.99 (s, 3H), 1.53-1.43 (m, 1H), 0.91~0.86 (m, 1H), 0.84 (s, 9H); $^{13}$C NMR (75 MHz, CDCl$_3$): δ 181.26, 173.14, 143.63, 142.69, 140.61, 134.18, 127.30, 126.60, 123.45, 123.41, 111.25, 110.62, 67.97, 66.08, 62.96, 48.57, 44.09, 30.57, 30.35, 26.60.

Example 64

(2'R,3S,4'R,5'R) 6-Chloro-2'-(2,2-Dimethyl-Propyl)-4'-Furan-2-yl-2-Oxo-1,2-Dihydro-Spiro[Indole-3,3'-Pyrrolidine]-5'-Carboxylic Acid Methylamide (G-80)

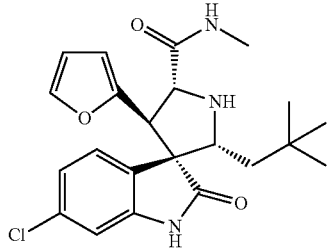 [SMILES: CNC(=O)[C@@H]1N[C@H](CC(C)(C)C)[C@]2(C(=O)Nc3cc(Cl)ccc32)[C@H]1c1ccco1]

$^1$H NMR (300 MHz, CDCl$_3$): δ 8.98 (s, 1H), 7.43 (J=4.8 Hz, 1H), 7.13~6.74 (m, 3H), 6.10~6.05 (m, 2H), 4.47 (d, J=9.30 Hz, 1H), 4.17 (d, J=9.35 Hz, 1H), 3.67 (d, J=8.00 Hz, 1H), 2.89 (d, J=4.90 Hz, 3H), 1.39-1.24 (m, 1H), 0.93~0.85 (m, 1H), 0.88 (s, 9H); $^{13}$C NMR (75 MHz, CDCl$_3$): δ 178.45, 173.65, 151.36, 142.40, 142.15, 134.26, 126.04, 125.88, 122.33, 111.11, 110.49, 107.83, 65.77, 65.20, 64.01, 52.45, 45.11, 32.00, 30.57, 30.36, 26.48.

Example 65

(2'R,3S,4'R,5'R) 4'-(3-Bromo-Phenyl)-2'-(2,2-Dimethyl-Propyl)-6-Methoxy-2-Oxo-1,2-Dihydro-Spiro[Indole-3,3'-Pyrrolidine]-5'-Carboxylic Acid Dimethylamide (KE-61)

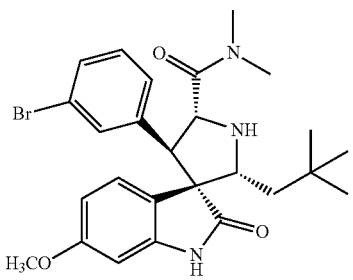 [SMILES: COc1ccc2c(c1)NC(=O)[C@]21[C@@H](CC(C)(C)C)N[C@@H](C(=O)N(C)C)[C@@H]1c1cccc(Br)c1]

$^1$H NMR (300 MHz, CDCl$_3$) δ 8.55 (s, 1H), 7.30 (d, J=7.1 Hz, 2H), 7.08 (d, J=3.9 Hz, 2H), 6.43-6.23 (m, 3H), 4.50 (d, J=6.6 Hz, 1H), 3.95 (d, J=7.3 Hz, 1H), 3.73 (s, 3H), 3.48 (d, J=8.3 Hz, 1H), 2.97 (s, 3H), 2.90 (s, 3H), 1.51-1.43 (m, 1H), 1.28 (m, 1H), 0.83 (s, 9H); $^{13}$C NMR (75 MHz, CDCl$_3$) δ 182.11, 170.81, 159.97, 142.78, 142.25, 132.10, 130.64, 130.32, 128.08, 126.09, 122.86, 120.31, 107.33, 97.00, 68.46, 65.74, 64.75, 58.54, 55.72, 43.63, 37.64, 36.56, 31.99, 30.59, 30.30.

Example 66

(2'R,3S,4'R,5'R) 6-(Chloro-4'-(3-Chloro-Phenyl)-2'-(2,2-Dimethyl-Propyl)-2-Oxo-1,2-Dihydro-Spiro[Indole-3,3'-Pyrrolidine]-5'-Carboxylic Acid (2-Morpholin-4-yl-Ethyl)-Amide (KE-79)

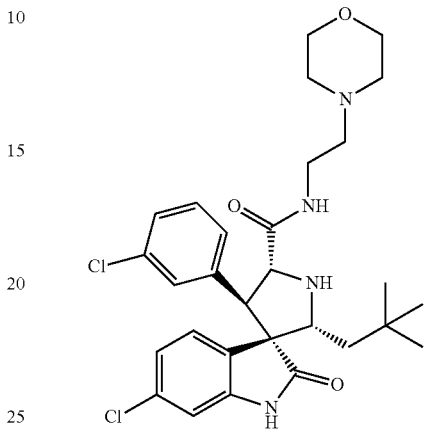

[α]$^{25}_D$ 45.29 (c 0.17, CH$_2$Cl$_2$); $^1$H NMR (300 MHz, CDCl$_3$) δ 8.33 (s, 1H), 7.17-7.10 (m, 4H), 6.95 (d, J=4.4 Hz, 1H), 6.81 (dd, J$_1$=8 Hz, J$_2$=1.6 Hz, 1H), 6.70 (d, J=1.8 Hz, 1H), 6.31 (d, J=8 Hz, 1H), 4.33 (d, J=7.1 Hz, 1H), 3.88 (d, J=7.12 Hz, 1H), 3.67-3.60 (m, 4H), 3.57 (d, J=8.1 Hz, 1H), 3.43-3.40 (m, 2H), 2.71-2.28 (m, 7H), 1.53-1.43 (m, 1H), 1.29-1.21 (m, 1H), 0.85 (s, 9H); $^{13}$C NMR (75 MHz, CDCl$_3$) δ 180.82, 172.17, 142.67, 141.28, 134.76, 134.18, 130.15, 128.98, 127.98, 127.46, 126.92, 126.25, 122.29, 110.66, 67.51, 67.33, 66.65, 64.03, 57.47, 57.20, 53.61, 44.28, 36.04, 31.99, 30.63, 30.50, 30.31; C$_{29}$H$_{30}$Cl$_2$N$_4$O$_3$+0.5 H$_2$O requires C, 61.26; H, 6.56; N, 9.85. Found C, 61.38; H, 7.08; N, 9.50.

Example 67

(2'R,3S,4'R,5'R) 6-Chloro-4'-(3-Chloro-Phenyl)-2'-(2,2-Dimethyl-Propyl)-2-Oxo-1,2-Dihydro-Spiro[Indole-3,3'-Pyrrolidine]-5'-Carboxylic Acid (3-Morpholin-4-yl-Propyl)-Amide (KE-78)

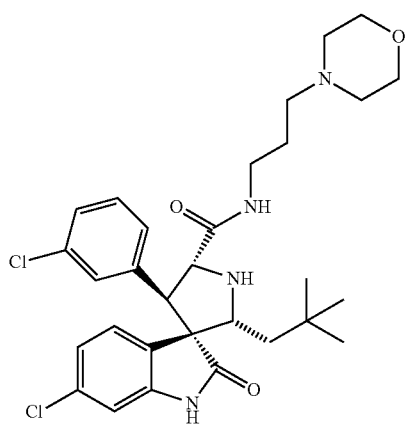 [SMILES: CC(C)(C)C[C@H]1N[C@@H](C(=O)NCCCN2CCOCC2)[C@H](c2cccc(Cl)c2)[C@@]12C(=O)Nc1cc(Cl)ccc12]

¹H NMR (300 MHz, CDCl₃), δ 8.57 (s, 1H), 7.29 (s, 1H), 7.28-7.10 (m, 3H), 6.96-6.93 (m, 1H), 6.80 (d, J=1.6 Hz, 1H), 6.68 (dd, J₁=7.3 Hz, J₂=1.6 Hz, 1H), 6.27 (d, J=8.1 Hz, 1H), 4.28 (d, J=6.9 Hz, 1H), 3.87 (d, J=7.3 Hz, 1H), 3.86-3.67 (m, 4H), 3.35 (d, J=7.6 Hz, 1H), 3.89-3.34 (m, 2H), 2.43-2.37 (m, 6H), 1.72-1.68 (m, 2H), 1.53-1.48 (m, 1H), 1.29-1.26 (m, 2H), 0.84 (s, 9H); ¹³C NMR (75 MHz, CDCl₃) δ 180.91, 172.08, 142.67, 141.34, 134.76, 134.19, 130.13, 129.08, 127.99, 127.49, 126.76, 126.31, 122.29, 110.63, 67.79, 67.35, 66.62, 63.80, 57.47, 57.41, 54.10, 44.15, 38.83, 31.99, 30.59, 30.40, 30.26.

Example 68

(2'R,3S,4'R,5'R) 6-Chloro-2'-(2,2-Dimethyl-Propyl)-4-(3-Fluoro-Phenyl)-2-Oxo-1,2-Dihydro-Spiro[Indole-3,3-Pyrrolidine]-5-Carboxylic Acid Dimethylamide (KE-75)

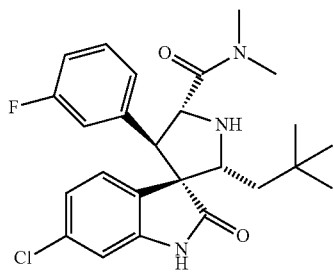 [SMILES: CN(C)C(=O)[C@@H]1N[C@H](CC(C)(C)C)[C@]2(C(=O)Nc3cc(Cl)ccc32)[C@H]1c1cccc(F)c1]

¹H NMR (300 MHz, CDCl₃) δ 8.59 (s, 1H), 7.29-7.20 (m, 1H), 6.98-6.87 (m, 4H), 6.68 (dd, J₁=7.8 Hz, J₂=1.7 Hz, 1H), 6.35 (d, J=7.5 Hz, 1H), 4.56 (s, 1H), 4.01 (d, J=6.1 Hz, 1H), 3.50 (m, 1H), 3.03 (s, 3H), 2.91 (s, 3H), 1.51-1.45 (m, 1H), 1.29-1.26 (m, 2H), 0.84 (s, 9H); ¹³C NMR (75 MHz, CDCl₃) δ 180.91, 170.20, 164.33, 161.06, 142.33, 141.71, 133.51, 130.20, 126.54, 125.66, 121.75, 115.74, 114.49, 110.19, 68.14, 65.34, 61.36, 43.12, 37.16, 36.19, 31.89, 30.13, 29.82.

Example 69

(2'R,3S,4'S,5'R) 6-Chloro-2'-(2,2-Dimethyl-Propyl)-4-(2,3-Difluoro-Phenyl)-2-Oxo-1,2-Dihydro-Spiro[Indole-3,3-Pyrrolidine]-5-Carboxylic Acid Dimethylamide (KE-74)

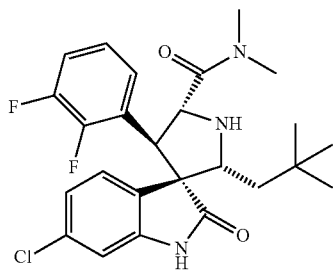 [SMILES: CN(C)C(=O)[C@@H]1N[C@H](CC(C)(C)C)[C@]2(C(=O)Nc3cc(Cl)ccc32)[C@H]1c1cccc(F)c1F]

¹H NMR (300 MHz, CDCl₃) δ 8.21 (s, 1H), 7.40 (d, J=8.0 Hz, 1H), 7.23 (s, 1H), 7.10 (d, J=8.0 Hz, 1H), 6.94-6.77 (m, 3H), 4.98 (d, J=8.45 Hz, 1H), 4.80 (d, J=8.6 Hz, 1H), 3.78 (d, J=8.7 Hz, 1H), 3.01 (s, 3H), 2.97 (s, 3H), 1.31-1.27 (m, 3H), 0.84 (s, 9H); ¹³C NMR (75 MHz, CDCl₃) δ 178.77, 172.84, 148.09, 142.12, 134.23, 126.61, 126.54, 124.72, 124.07, 116.51, 116.28, 110.47, 67.08, 66.23, 61.98, 48.40, 43.87, 37.77, 36.70, 35.06, 31.99, 30.58, 30.21.

Example 70

(2'R,3S,4'S,5'R) 6-Chloro-2'-(2,2-Dimethyl-Propyl)-4-(2-Chloro-3-Fluoro-Phenyl)-2-Oxo-1,2-Dihydro-Spiro[Indole-3,3-Pyrrolidine]-5-Carboxylic Acid (2-Diethylamino-Ethyl)-Amide (KE-73)

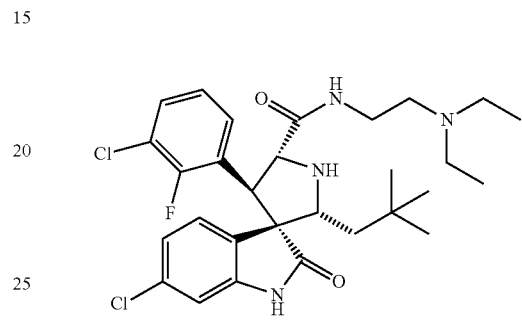

¹H NMR (300 MHz, CDCl₃), δ 8.55 (s, 1H), 7.50 (m, 1H), 7.18 (t, J=2.4 Hz, 1H), 7.08 (t, J=3.2 Hz, 1H), 6.86 (s, 1H), 6.64 (d, J=1.6 Hz, 1H), 6.26 (d, J=3.4 Hz, 1H), 4.43 (d, J=3.2 Hz, 1H), 4.25 (d, J=2.5 Hz, 1H), 4.43 (d, J=8.1 Hz, 1H), 4.16 (d, J=7.8 Hz, 1H), 3.60-3.51 (m, 2H), 3.41 (d, J=8.3 Hz, 1H), 3.40-2.91 (m, 6H), 1.48-1.43 (m, 2H), 1.19-1.14 (t, J=6.8 Hz, 6H), 0.79 (s, 9H); ¹³C NMR (75 MHz, CDCl₃), δ 181.59, 177.47, 172.58, 143.39, 134.01, 129.76, 127.48, 126.92, 125.51, 124.85, 121.99, 110.70, 67.90, 66.56, 63.64, 53.01, 51.62, 43.60, 35.88, 31.99, 30.54, 23.26, 23.05.

Example 71

(2'R,3S,4'R,5'R) 6-Chloro-2'-(2,2-Dimethyl-Propyl)-4-(3-Chloro-Phenyl)-2-Oxo-1,2-Dihydro-Spiro[Indole-3,3-Pyrrolidine]-5-Carboxylic Acid Methylamide (KE-71)

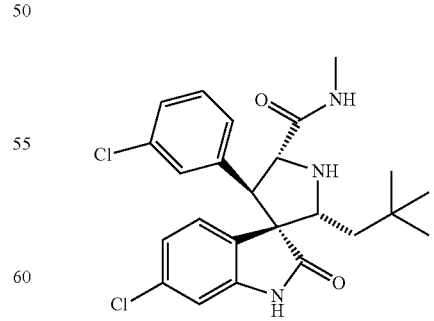

¹³C NMR (75 MHz, CDCl₃) δ 181.25, 170.16, 142.89, 134.06, 133.01, 128.70, 128.49, 126.82, 125.59, 125.37, 125.21, 122.21, 110.62, 68.94, 64.30, 64.09, 52.99, 43.32, 37.48, 36.55, 30.58, 30.25.

Example 72

(2'R,3S,4'S,5'R) 6-(Chloro-4'-(3-Bromo-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (2-Morpholin-4-yl-Ethyl)-Amide (KE-90)

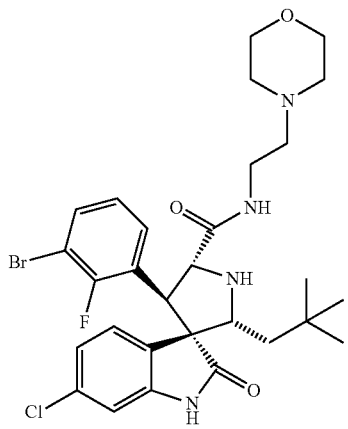 [SMILES: CC(C)(C)C[C@H]1N[C@@H](C(=O)NCCN2CCOCC2)[C@H](c2cccc(Br)c2F)[C@@]12C(=O)Nc1cc(Cl)ccc12]

$^1$H NMR (300 MHz, CDCl$_3$) δ 7.99 (m, 1H), 7.10-6.90 (m, 4H), 6.78 (s, 1H), 3.73-3.67 (m, 4H), 3.42-3.39 (m, 3H), 3.01-2.96 (m, 1H), 2.56-2.49 (m, 6H), 2.3-2.2 (m, 2H), 1.51-1.47 (m, 1H), 1.27-1.18 (m, 3H), 0.87 (s, 9H); $^{13}$C NMR (75 MHz, CDCl$_3$) δ 179.40, 174.02, 142.20, 134.24, 126.74, 125.84, 122.70, 111.22, 68.96, 67.92, 67.25, 65.40, 57.64, 53.84, 49.27, 44.95, 44.58, 35.50, 30.59, 30.11, 29.90.

Example 73

(2'R,3S,4'S,5'R) 6-Chloro-2'-(2,2-Dimethyl-Propyl)-4-(3-Bromo-2-Fluoro-Phenyl)-2-Oxo-1,2-Dihydro-Spiro[Indole-3,3-Pyrrolidine]-5-Carboxylic Acid Dimethylamide (KE-91)

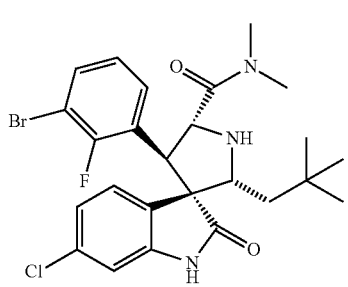 [SMILES: CN(C)C(=O)[C@@H]1N[C@H](CC(C)(C)C)[C@]2(C(=O)Nc3cc(Cl)ccc32)[C@H]1c1cccc(Br)c1F]

$^1$H NMR (300 MHz, CDCl$_3$) δ 7.65 (s, 1H), 7.39-7.24 (m, 1H), 6.98-6.90 (m, 1H), 6.82 (s, 1H), 6.69 (d, J=6.5 Hz, 1H), 6.41 (d, J=6.7 Hz, 1H), 4.60-4.53 (m, 1H), 4.35 (d, J=7.4 Hz, 1H), 3.43-3.34 (m, 1H), 3.05 (s, 3H), 3.00 (s, 3H), 1.51-1.45 (m, 1H), 1.30-1.25 (m, 2H), 0.86 (s, 9H).

Example 74

(2'R,3S,4'S,5'R) 6-Methyl-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (3-Morpholin-4-yl-Propyl)-Amide (KE-92)

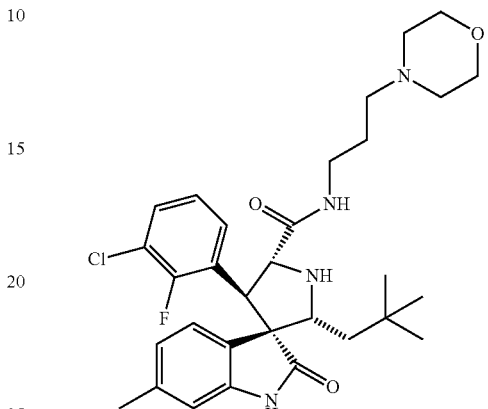

$^1$H NMR (300 MHz, CDCl$_3$) δ 7.70-7.00 (m, 5H), 6.62 (s, 1H), 6.49 (d, J=7.8 Hz, 1H), 6.20 (d, J=7.8 Hz, 1H), 4.40 (d, J=7.7 Hz, 1H), 4.07 (d, J=7.8 Hz, 1H), 3.82 (m, 4H), 3.52-3.34 (m, 3H), 2.62 (m, 6H), 2.24 (s, 3H), 1.85 (m, 2H), 1.54-1.46 (m, 1H), 0.98-0.91 (m, 2H), 0.87 (s, 9H); $^{13}$C NMR (75 MHz, CDCl$_3$) δ 181.12, 172.46, 141.51, 138.67, 129.71, 129.01, 128.81, 127.87, 124.71, 124.65, 124.50, 123.04, 121.81, 110.73, 66.64, 66.17, 63.08, 57.03, 53.74, 51.37, 43.76, 38.18, 30.56, 30.22, 30.10.

Example 75

(2'R,3'S,4'R,5'R) 6-Chloro-4'-2,2-Dimethyl-Propyl-2'-(2,2-Dimethyl-Propyl)-2-Oxo-1,2-Dihydro-Spiro[Indole-3,3'-Pyrrolidine]-5'-Carboxylic Acid (3-Morpholin-4-yl-propyl)-Amide (KE-93)

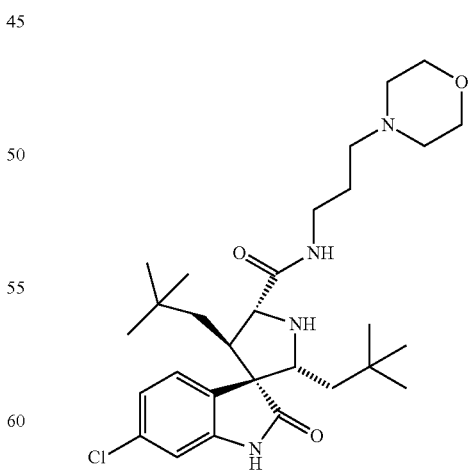

$^1$H NMR (300 MHz, CDCl$_3$) δ 8.53 (s, 1H), 7.54 (m, 1H), 7.10-6.95 (m, 2H), 6.94 (s, 1H), 4.20-4.11 (m, 4H), 3.43-3.15 (m, 4H), 2.65-2.34 (m, 6H), 2.29 (m, 1H), 1.76-1.18 (m, 7H), 0.76 (s, 9H), 0.55 (s, 9H); $^{13}$C NMR (75 MHz, CDCl$_3$) δ

182.24, 142.81, 134.08, 129.13, 127.09, 122.46, 110.81, 68.70, 67.44, 64.53, 62.82, 57.80, 54.12, 49.41, 43.97, 43.03, 39.30, 38.99, 31.99, 30.64, 30.52, 30.21, 29.39, 25.74.

Example 76

(2'R,3S,4'R,5'R) 6-Chloro-4'-2,2-Dimethyl-Propyl-2'-(2,2-Dimethyl-Propyl)-2-Oxo-1,2-Dihydro-Spiro[Indole-3,3'-Pyrrolidine]-5'-Carboxylic Acid Methylamide (KE-94)

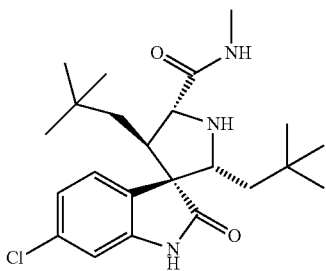 [SMILES: CNC(=O)[C@@H]1N[C@H](CC(C)(C)C)[C@]2(C(=O)Nc3cc(Cl)ccc32)[C@H]1CC(C)(C)C]

$^1$H NMR (300 MHz, CDCl$_3$) δ 8.90 (s, 1H), 7.10-6.90 (m, 3H), 3.52 (d, J=7.6 Hz, 1H), 3.25 (d, J=7.5 Hz, 1H), 2.88 (d, J=4.5 Hz, 3H), 2.54 (m, 1H), 2.30 (m, 1H), 1.64-1.45 (m, 3H), 1.27 (m, 2H), 0.76 (s, 9H), 0.56 (s, 9H); $^{13}$C NMR (75 MHz, CDCl$_3$) δ 182.51, 173.37, 142.95, 134.13, 129.05, 127.14, 122.47, 110.96, 71.11, 68.01, 62.60, 48.92, 44.09, 42.88, 39.81, 31.99, 30.60, 30.51, 30.20, 29.35, 26.43.

Example 77

(2'R,3S,4'S,5'R) 6-Chloro-4'-(3-Chloro-2-Fluoro-Phenyl)-2'-(2,2-Dimethyl-Butyl)-2-Oxo-1,2-Dihydro-Spiro[Indole-3,3'-Pyrrolidine]-5'-Carboxylic Acid (3-Morpholin-4-yl-Propyl)-Amide (GM-29)

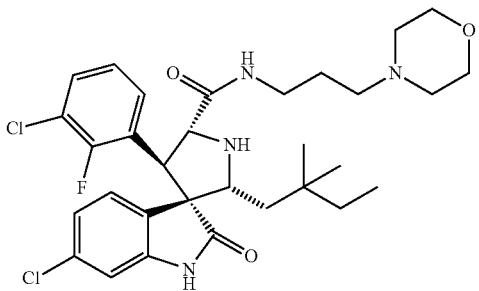 [SMILES: CCC(C)(C)C[C@H]1N[C@@H](C(=O)NCCCN2CCOCC2)[C@H](c2cccc(Cl)c2F)[C@@]12C(=O)Nc1cc(Cl)ccc12]

$^1$H NMR (300 MHz, CDCl$_3$) δ 8.23 (s, 1H), 7.39-7.21 (m, 3H), 7.05 (t, J=7.9 Hz, 1H), 6.83 (s, 1H), 6.68 (d, J=8.1 Hz, 1H), 6.30 (d, J=8.0 Hz, 1H), 4.40 (d, J=7.90 Hz, 1H), 4.09 (d, J=7.6 Hz, 1H), 3.81-3.67 (m, 4H), 3.54-3.31 (m, 3H), 2.62-2.34 (m, 6H), 1.75-1.69 (m, 2H), 1.51-0.145 (m, 1H), 1.24-1.20 (m, 2H), 1.18-1.10 (m, 2H), 0.76-0.70 (m, 6H), 0.57-0.061 (m, 3H).

Example 78

(2'R,3S,4S,5'R) 6-Chloro-4'-(3-Chloro-2-Fluoro-Phenyl)-2'-(2,2-Dimethyl-Pentyl)-2-Oxo-1,2-Dihydro-Spiro[Indole-3,3'-Pyrrolidine]-5'-Carboxylic Acid (3-Morpholin-4-yl-Propyl)-Amide (KE-101)

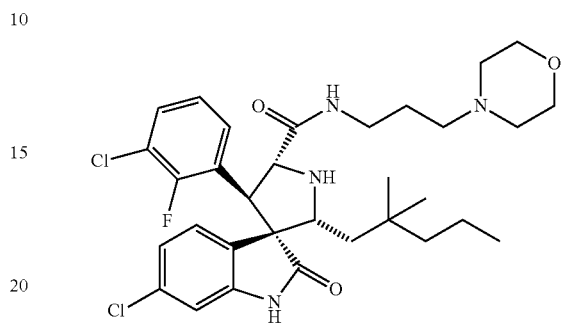

$^1$H NMR (300 MHz, CDCl$_3$) δ 7.89 (s, 1H), 7.74-6.09 (m, 3H), 6.83 (s, 1H), 6.68 (d, J=8.0 Hz, 1H), 6.27 (d, J=8.1 Hz, 1H), 4.40 (d, J=7.6 Hz, 1H), 4.08 (d, J=7.5 Hz, 1H), 3.77 (m, 4H), 3.50-3.36 (m, 5H), 2.54 (m, 7H), 1.78 (m, 2H), 1.51-1.47 (m, 1H), 1.27 (m, 4H), 1.12-0.76 (m, 8H); $^{13}$C NMR (75 MHz, CDCl$_3$) δ 180.75, 171.96, 142.71, 141.96, 134.35, 129.99, 128.33, 127.81, 126.69, 126.65, 124.87, 123.36, 122.30, 110.57, 67.03, 66.66, 66.07, 63.06, 57.25, 53.96, 44.98, 41.69, 38.53, 33.00, 31.99, 28.05, 27.88, 25.82, 23.06, 17.31, 15.32.

Example 79

(2'R,3S,4S,5'R) 6-Methoxy-4'-(3-Bromo-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (3-Morpholin-4-yl-Propyl)-Amide (KE-102)

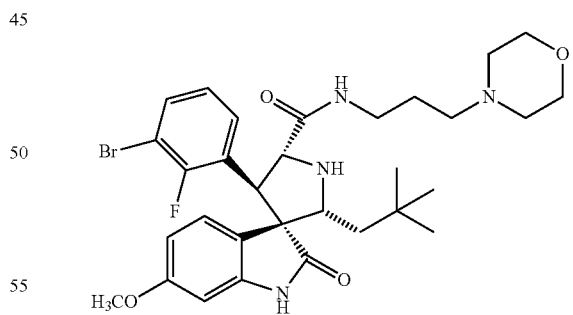

$^1$H NMR (300 MHz, CDCl$_3$) δ 7.55 (s, 1H), 7.41 (m, 1H), 7.32-7.00 (m, 3H), 6.36 (s, 1H), 6.26-6.17 (m, 2H), 4.37 (d, J=7.9 Hz, 1H), 4.0 (d, J=8.2 Hz, 1H), 3.73 (s, 3H), 3.70 (m, 6H), 3.44 (d, J=8.1 Hz, 1H), 3.38-3.34 (m, 2H), 2.43-2.38 (m, 4H), 2.05 (m, 1H), 1.75-1.69 (m, 2H), 1.51-1.47 (m, 1H), 0.97~0.89 (m, 1H), 0.79 (s, 9H); $^{13}$C NMR (75 MHz, CDCl$_3$) δ 181.37, 160.20, 142.56, 129.72, 128.27, 127.85, 125.55, 119.62, 110.05, 97.05, 70.81, 67.33, 66.65, 66.16, 62.89, 57.36, 55.72, 54.11, 52.30, 51.57, 49.29, 43.75, 38.60, 30.59.

Example 80

(2'R,3S,4R,5'R) 6-Chloro-4'-(3-Chloro-5-Fluoro-Phenyl)-2'-(2,2-Dimethyl-Propyl)-2-Oxo-1,2-Dihydro-Spiro[Indole-3,3'-Pyrrolidine]-5'-Carboxylic Acid (3-Morpholin-4-yl-Propyl)-Amide (KE-103)

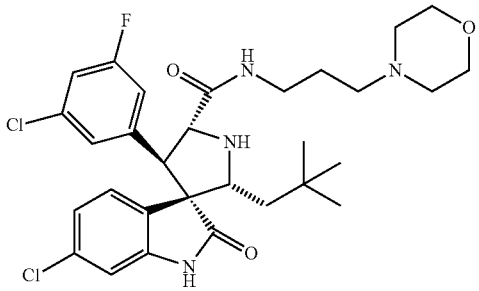 [SMILES: CC(C)(C)C[C@H]1N[C@@H](C(=O)NCCCN2CCOCC2)[C@H](c2cc(F)cc(Cl)c2)[C@@]12C(=O)Nc1cc(Cl)ccc12]

$^1$H NMR (300 MHz, CDCl$_3$) δ 8.31 (m, 1H), 7.42 (m, 1H), 6.94-6.67 (m, 5H), 6.38 (d, J=7.5 Hz, 1H), 4.25 (d, J=7.8 Hz, 1H), 3.88 (d, J=8.2 Hz, 1H), 3.78 (m, 4H), 3.53 (d, J=8.1 Hz, 1H), 3.39 (m, 2H), 2.54-2.49 (m, 6H), 1.80-1.74 (m, 2H), 1.51-1.46 (m, 1H), 0.90~0.85 (m, 1H), 0.84 (s, 9H); $^{13}$C NMR (75 MHz, CDCl$_3$) δ 180.31, 171.79, 143.02, 142.37, 135.42, 126.51, 126.18, 125.16, 122.58, 115.82, 115.50, 114.83, 114.54, 110.70, 67.63, 67.01, 66.79, 63.58, 57.26, 54.08, 46.38, 38.60, 33.32, 30.59, 30.35, 30.23.

Example 81

(2'R,3S,4S,5'R) 6-Chloro, 7-Fluoro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (3-Morpholin-4-yl-Propyl)-Amide (KE-104)

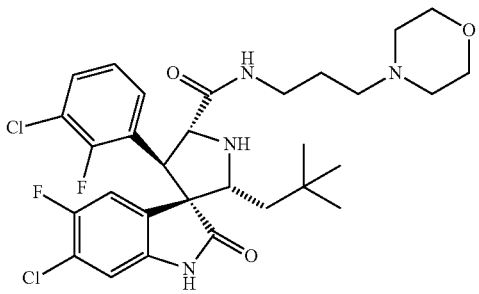 [SMILES: CC(C)(C)C[C@H]1N[C@@H](C(=O)NCCCN2CCOCC2)[C@H](c2cccc(Cl)c2F)[C@@]12C(=O)Nc1cc(Cl)c(F)cc12]

$^1$H NMR (300 MHz, CDCl$_3$) δ 8.23 (s, 1H), 7.43-7.01 (m, 4H), 6.87 (d, J=6.0 Hz, 1H), 6.22 (d, J=8.6 Hz, 1H), 4.40 (d, J=8.0 Hz, 1H), 4.12 (d, J=7.8 Hz, 1H), 3.70 (m, 4H), 3.56-3.48 (m, 4H), 2.67-2.60 (m, 7H), 1.76-1.70 (m, 2H), 0.90~0.88 (m, 1H), 0.86 (s, 9H); $^{13}$C NMR (75 MHz, CDCl$_3$) δ 180.62, 171.58, 138.22, 128.20, 127.92, 127.57, 125.07, 125.02, 122.17, 121.93, 120.98, 120.72, 113.63, 111.58, 67.43, 67.18, 66.22, 63.61, 57.42, 54.05, 51.79, 43.68, 38.79, 32.00, 30.86, 30.55, 30.38.

Example 82

(2'R,3S,4S,5'R) 6-Chloro, 7-Fluoro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (2-Morpholin-4-yl-Propyl)-Amide (KE-109)

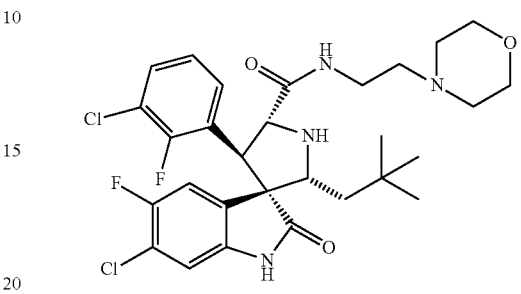

$^1$H NMR (300 MHz, CDCl$_3$) δ 8.53 (s, 1H), 7.23-7.10 (m, 4H), 6.87 (d, J=6 Hz, 1H), 6.22 (d, J=8.5 Hz, 1H), 4.43 (d, J=8.1 Hz, 1), 4.14 (d, J=8.1 Hz, 1H), 3.68 (m, 4H), 3.46-3.41 (m, 3H), 2.54-2.47 (m, 6H), 1.51-1.46 (m, 1H), 0.92~0.89 (m, 2H), 0.86 (s, 9H); $^{13}$C NMR (75 MHz, CDCl$_3$) δ 180.83, 171.55, 158.37, 155.70, 152.47, 138.31, 130.28, 128.34, 127.90, 125.08, 122.18, 120.94, 113.51, 111.66, 67.70, 67.28, 66.15, 63.96, 57.19, 53.85, 51.76, 43.66, 35.96, 31.99, 30.68, 30.27.

Example 83

(2'R,3S,4S,5'R) 6-Chloro, 7-Fluoro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (2-Pyrrolidin-1-yl-Ethyl)-Amide (KE-110)

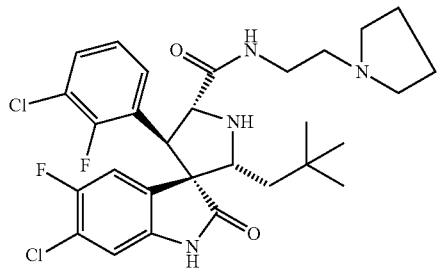 [SMILES: CC(C)(C)C[C@H]1N[C@@H](C(=O)NCCN2CCCC2)[C@H](c2cccc(Cl)c2F)[C@@]12C(=O)Nc1cc(Cl)c(F)cc12]

$^1$H NMR (300 MHz, CDCl$_3$) δ 9.79 (s, 1H), 8.60 (s, 1H), 7.57 (s, 1H), 7.27-6.87 (m, 3H), 5.90 (d, J=8.1 Hz, 1H), 4.51 (m, 1H), 4.23 (m, 1H), 3.7-3.1 (m, 9H), 2.12 (m 3H), 1.49-1.41 (m, 4H), 0.82 (s, 9H); $^{13}$C NMR (75 MHz, CDCl$_3$) δ 181.11, 174.19, 155.66, 138.77, 130.35, 127.98, 127.39, 125.43, 121.79, 121.52, 121.12, 113.38, 113.06, 112.33, 66.17, 64.44, 63.28, 55.27, 55.11, 49.44, 46.58, 43.89, 36.26, 30.50, 30.14, 23.66.

Example 84

(2'R,3S,4S,5'R) 6-Chloro, 7-Fluoro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (2-Piperidin-1-yl-Ethyl)-Amide (KE-111)

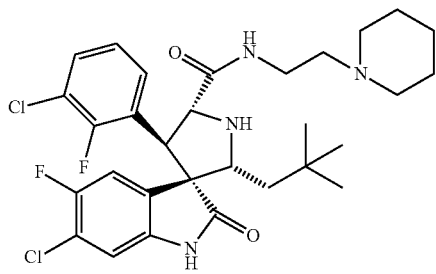 [SMILES: CC(C)(C)C[C@H]1N[C@@H](C(=O)NCCN2CCCCC2)[C@H](c2cccc(Cl)c2F)[C@@]12C(=O)Nc1cc(Cl)c(F)cc12]

$^1$H NMR (300 MHz, CDCl$_3$) δ 7.34-7.23 (m, 4H), 7.13 (m, 1H), 6.88 (m 1H), 6.22 (d, J=8.2 Hz, 1H), 4.42 (d, J=8.3 Hz, 1H), 4.15 (d, J=7.8 Hz, 1H), 3.41 (m, 3H), 2.47 (m, 7H), 1.58~0.92 (m, 8H), 0.85 (s, 9H); $^{13}$C NMR (75 MHz, CDCl$_3$) δ 180.89, 171.50, 158.38, 155.69, 152.47, 130.19, 128.49, 127.88, 125.06, 122.09, 121.85, 120.60, 113.51, 111.63, 67.93, 66.13, 54.04, 57.80, 54.81, 51.76, 43.61, 36.14, 32.00, 30.85, 30.67, 26.25, 25.90, 24.39.

Example 85

(2'R,3S,4S,5'R) 6-Chloro, 7-Fluoro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid [2-(Tetrahydro-Pyran-4-yl)-Ethyl]-Amide (KE-112)

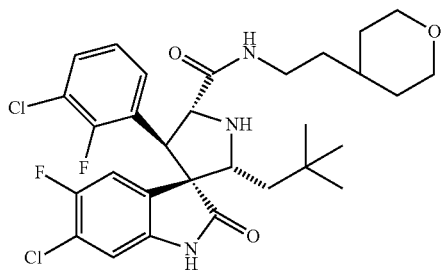 [SMILES: CC(C)(C)C[C@H]1N[C@@H](C(=O)NCCC2CCOCC2)[C@H](c2cccc(Cl)c2F)[C@@]12C(=O)Nc1cc(Cl)c(F)cc12]

$^1$H NMR (300 MHz, CDCl$_3$) δ 8.51 (s, 1H), 7.32-6.78 (m, 3H), 6.26 (d, J=8.5 Hz, 1H), 4.38 (d, J=7.8 Hz, 1H), 4.05 (d, J=7.7 Hz, 1H), 3.90-3.78 (m, 2H), 3.54-3.22 (m, 6H), 1.65-1.25 (m, 11H), 0.86 (s, 9H); $^{13}$C NMR (75 MHz, CDCl$_3$) δ 180.66, 171.92, 158.32, 152.47, 138.28, 130.36, 128.09, 127.99, 127.77, 127.49, 122.19, 120.80, 111.30, 111.65, 68.34, 66.96, 65.93, 63.42, 51.39, 43.76, 37.13, 37.01, 33.25, 33.16, 30.56, 30.36, 30.23, 27.12.

Example 86

(2'R,3S,4R,5'R) 6-Chloro-4'-(3-Chloro-5-Fluoro-Phenyl)-2'-(2,2-Dimethyl-Propyl)-2-Oxo-1,2-Dihydro-Spiro[Indole-3,3'-Pyrrolidine]-5'-Carboxylic Acid (2-Morpholin-4-yl-Ethyl)-Amide (KE-115)

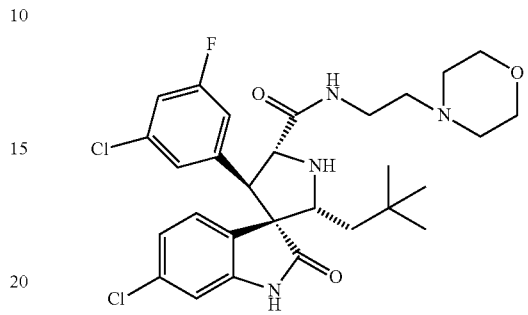

$^1$H NMR (300 MHz, CDCl$_3$) δ 8.01 (s, 1H), 7.13 (m, 1H), 6.94-6.70 (m, 5H), 6.42 (d, J=8.0 Hz, 1H), 4.30 (d, J=7.6 Hz, 1H), 3.88 (d, J=7.6 Hz, 1H), 3.68 (m, 4H), 3.56 (d, J=9.1 Hz, 1H), 3.43-3.37 (m, 2H), 2.56-2.40 (m, 4H), 1.80 (m, 2H), 1.51-1.46 (m, 1H), 0.90~0.85 (m, 1H), 0.86 (s, 9H); $^{13}$C NMR (75 MHz, CDCl$_3$) δ 180.17, 171.69, 142.97, 142.28, 135.35, 134.46, 126.76, 126.13, 125.07, 122.60, 115.81, 115.48, 114.47, 110.69, 67.45, 67.36, 66.93, 63.86, 57.32, 57.22, 53.66, 44.27, 35.99, 30.65, 30.30.

Example 87

(2'R,3S,4S,5'R) 6-Chloro-4'-(3-Chloro-2-fluoro-Phenyl)-2'-(2,2-Dimethyl-Propyl)-2-Oxo-1,2-Dihydro-Spiro[Indole-3,3'-Pyrrolidine]-5'-Carboxylic Acid [2-(Tetrahydro-Pyran-4-yl)-Ethyl]-Amide (KE-MDM2-108)

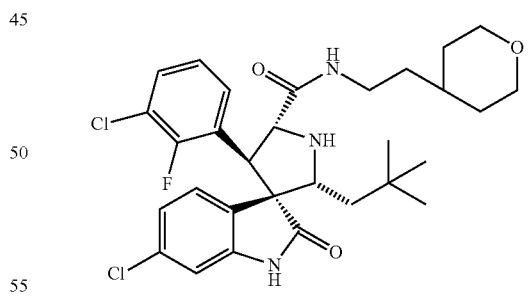

$^1$H NMR (300 MHz, CDCl$_3$) δ 8.65 (s, 1H), 7.33-7.20 (m, 2H), 7.08-7.03 (m, 2H), 6.83 (d, J=1.8 Hz, 1H), 6.67 (dd, J$_1$=8.1 Hz, J$_2$=1.8 Hz, 1H), 6.26 (d, J=6 Hz, 1H), 4.13 (d, J=7.8 Hz, 1H), 4.06 (d, J=7.5 Hz, 1H), 3.96-3.91 (m, 2H), 3.50 (d, J=9 Hz, 1H), 3.38-3.29 (m, 4H), 1.61-1.48 (m, 6H), 1.31-1.27 (m, 2H), 0.86 (d, J=9 Hz, 1H), 0.82 (s, 9H); $^{13}$C NMR (75 MHz, CDCl$_3$) δ 181.10, 172.29, 142.98, 134.36, 130.06, 128.40, 128.21, 127.68, 126.36, 125.60, 124.83, 122.25, 121.77, 110.73, 68.34, 66.54, 65.88, 62.95, 43.82, 37.11, 36.88, 33.26, 33.15, 30.56, 30.21.

Example 88

(2'R,3S,4S,5'R) 6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (2-Morpholin-4-yl-Ethyl)-Amide (KE-63)

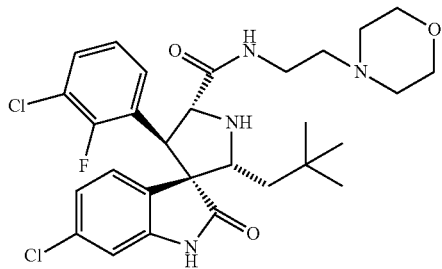 [SMILES: CC(C)(C)C[C@H]1N[C@@H](C(=O)NCCN2CCOCC2)[C@H](c2cccc(Cl)c2F)[C@@]12C(=O)Nc1cc(Cl)ccc12]

$[\alpha]^{25}_D$, +5.8 (c 0.9 CHCl$_3$); $^1$H NMR (300 MHz, CDCl$_3$), δ 7.83 (br, 1H), 7.34~7.20 (m, 3H), 7.07 (t, dd, J=7.91, 7.94 Hz, 1H), 6.83 (d, J=1.83 Hz, 1H), 6.69 (dd, J=1.86, 8.11 Hz, 1H), 6.30 (d, J=8.17 Hz, 1H), 4.44 (d, J=8.05 Hz, 1H), 4.12 (d, J=8.04 Hz, 1H), 3.68 (t, J=4.56 Hz, 4H), 3.49~3.35 (m, 3H), 2.59~2.20 (m, 7H), 1.52 (dd, J=9.80, 14.10 Hz, 1H), 0.95~0.89 (m, 1H), 0.84 (s, 9H); $^{13}$C NMR (75 MHz, CDCl$_3$), δ 180.34, 171.30, 142.16, 133.89, 129.57, 128.12, 127.93, 127.09, 126.15, 124.42, 124.36, 121.93, 121.61, 110.13, 66.91, 65.63, 62.93, 56.79, 53.40, 51.28, 43.31, 35.55, 30.18, 30.04, 29.83; C$_{29}$H$_{35}$Cl$_2$FN$_4$O$_3$+H$_2$O requires C, 58.49; H, 6.26; N, 9.41. Found C, 58.70; H, 6.44; N, 9.23.

Example 89

(2'R,3S,4S,5'R) 6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (3-Morpholin-4-yl-Propyl)-Amide (KE-64')

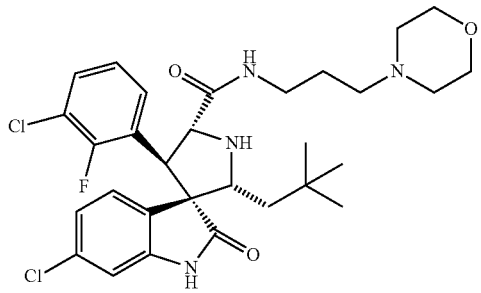 [SMILES: CC(C)(C)C[C@H]1N[C@@H](C(=O)NCCCN2CCOCC2)[C@H](c2cccc(Cl)c2F)[C@@]12C(=O)Nc1cc(Cl)ccc12]

$^1$H NMR (300 MHz, CDCl$_3$) δ 8.40 (s, 1H), 7.31-7.20 (m, 3H), 7.10-7.05 (m, 1H), 6.83 (d, J=1.8 Hz, 1H), 6.80 (dd, J$_1$=8.1 Hz, J$_2$=1.8 Hz, 1H), 6.30 (d, J=8.1 Hz, 1H), 4.44 (d, J=8.1 Hz, 1H), 4.13 (d, J=8.1 Hz, 1H), 3.70-3.66 (m, 4H), 3.49-3.40 (m, 3H), 3.08 (m, 2H), 2.55-2.46 (m, 6H), 1.51-1.45 (m, 1H), 0.95~0.85 (m, 1H), 0.83 (s, 9H); $^{13}$C NMR (75 MHz, CDCl$_3$) δ 180.61, 171.38, 142.38, 133.85, 129.55, 128.09, 127.90, 127.07, 126.14, 125.08, 124.43, 121.84, 121.33, 110.23, 66.83, 65.61, 62.97, 60.40, 56.77, 53.18, 51.25, 43.30, 35.53, 30.16, 29.81.

Example 90

(Racemic) 6-Chloro-4'-(3-Chloro-2-Fluoro-Phenyl)-2'-(2,2-Dimethyl-Propyl)-1'-Methyl-2-Oxo-1,2-Dihydro-Spiro[Indole-3,3'-Pyrrolidine]-5'-Carboxylic Acid Tert-Butyl Ester

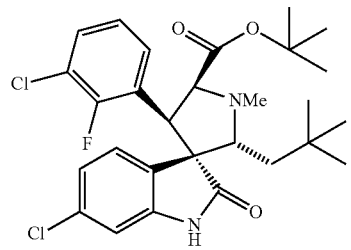 [SMILES: CN1[C@H](C(=O)OC(C)(C)C)[C@H](c2cccc(Cl)c2F)[C@@]2(C(=O)Nc3cc(Cl)ccc32)[C@H]1CC(C)(C)C]

$^1$H NMR (300 MHz, CDCl$_3$) δ 8.16 (s, 1H), 7.53 (m, 1H), 7.30 (m, 1H), 7.08 (m, 1H), 6.93 (d, J=1.8 Hz, 1H), 6.72 (dd, J$_1$=8.1 Hz, J$_2$=1.8 Hz, 1H), 6.11 (d, J=7.9 Hz, 1H), 4.59 (d, J=7.5 Hz, 1H), 4.31 (d, J=7.3 Hz, 1H), 3.81-3.78 (m, 1H), 2.69 (s, 3H), 1.96-1.88 (m, 1H), 1.12 (s, 9H), 0.80~0.89 (m, 1H), 0.63 (s, 9H).

Example 91

(2'S,3R,4'R,5'S) 6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (2-Morpholin-4-yl-Ethyl)-Amide (KE-98 (63B, Mirror Image of KE-63))

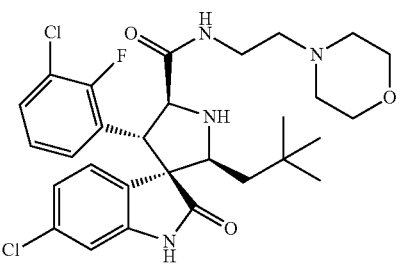 [SMILES: CC(C)(C)C[C@@H]1N[C@H](C(=O)NCCN2CCOCC2)[C@@H](c2cccc(Cl)c2F)[C@]12C(=O)Nc1cc(Cl)ccc12]

$[\alpha]^{25}_D$ −6.5 (c 1 CHCl$_3$); C$_{29}$H$_{35}$Cl$_2$FN$_4$O$_3$+H$_2$O requires C, 58.49; H, 6.26; N, 9.41. Found C, 58.73; H, 6.54; N, 9.18 $^1$H NMR (300 MHz, CDCl$_3$), δ 7.83 (br, 1H), 7.34~7.20 (m, 3H), 7.07 (t, dd, J=7.91, 7.94 Hz, 1H), 6.83 (d, J=1.83 Hz, 1H), 6.69 (dd, J=1.86, 8.11 Hz, 1H), 6.30 (d, J=8.17 Hz, 1H), 4.44 (d, J=8.05 Hz, 1H), 4.12 (d, J=8.04 Hz, 1H), 3.68 (m, 4H), 3.49~3.35 (m, 3H), 2.59~2.20 (m, 7H), 1.52 (dd, J=9.80, 14.10 Hz, 1H), 0.95~0.89 (m, 1H), 0.84 (s, 9H); $^{13}$C NMR (75 MHz, CDCl$_3$), δ 180.34, 171.30, 142.16, 133.89, 129.57, 128.12, 127.93, 127.09, 126.15, 124.42, 124.36, 121.93, 121.61, 110.13, 66.91, 65.63, 62.93, 56.79, 53.40, 51.28, 43.31, 35.55, 30.18, 30.04, 29.83.

Example 92

(2'R,3S,4R,5'R) 6-chloro-4'-(3-Chloro-Phenyl)-2'-(2,2-Dimethyl-Propyl)-5'-Methylcarbamoyl-2-Oxo-1,2-Dihydro-Spiro[Indole-3,3'-Pyrrolidine]-1'-Carboxylic Acid Methyl Ester (KE-66)

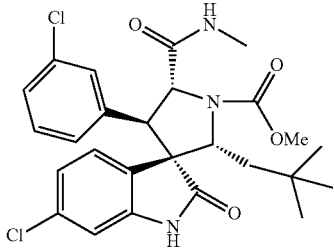 [SMILES: CNC(=O)[C@H]1[C@H](c2cccc(Cl)c2)[C@@]2(C(=O)Nc3cc(Cl)ccc32)[C@@H](CC(C)(C)C)N1C(=O)OC]

$^1$H NMR (300 MHz, CDCl$_3$), δ 7.86 (s, 1H), 7.70 (s, 1H), 7.27~6.95 (m, 5H), 4.56 (d, J=8.70 Hz, 1H), 3.93 (s, 3H), 3.87 (d, J=9 Hz, 1H), 3.50~3.47 (m, 1H), 3.05 (m, 1H), 2.88 (d, J=5.1 Hz, 3H), 1.55~0.89 (m, 2H), 0.89 (s, 9H).

Example 93

(2'R,3S,4S,5'R) 6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (2-Dimethylamino-Ethyl)-MethylAmide (KE-62)

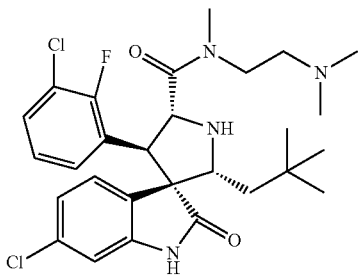 [SMILES: CN(C)CCN(C)C(=O)[C@@H]1N[C@H](CC(C)(C)C)[C@]2(C(=O)Nc3cc(Cl)ccc32)[C@H]1c1cccc(Cl)c1F]

$^1$H NMR (300 MHz, CDCl$_3$), δ 7.28~7.16 (m, 3H), 7.06 (t, dd, J=7.91, 7.94 Hz, 1H), 6.82 (d, J=1.83 Hz, 1H), 6.70 (dd, J=1.86, 8.11 Hz, 1H), 6.39 (d, J=8.17 Hz, 1H), 4.44 (d, J=8.05 Hz, 1H), 4.12 (d, J=8.04 Hz, 1H), 3.49~3.35 (m, 3H), 2.99 (s, 3H), 2.59~2.40 (m, 2H), 2.30 (s, 3H), 2.24 (s, 3H), 1.52 (dd, J=9.80, 14.10 Hz, 1H), 0.95~0.89 (m, 1H), 0.84 (s, 9H).

Example 94

KE-68

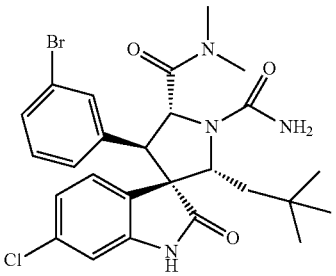 [SMILES: CN(C)C(=O)[C@H]1[C@H](c2cccc(Br)c2)[C@@]2(C(=O)Nc3cc(Cl)ccc32)[C@@H](CC(C)(C)C)N1C(N)=O]

$^1$H NMR (300 MHz, CDCl$_3$), δ 8.28 (br, 1H), 7.31~7.23 (m, 3H), 7.14~7.07 (m, 2H), 6.94 (d, J=1.79 Hz, 1H), 6.75 (dd, J=1.86, 8.10 Hz, 1H), 5.30 (d, J=12.1 Hz, 1H), 4.69 (s, 2H), 4.24 (m, 1H), 3.86 (d, J=8.12 Hz, 1H), 2.92 (s, 3H), 2.87 (s, 3H), 1.52~1.44 (m, 1H), 0.97~0.92 (m, 1H), 0.89 (s, 9H).

Example 95

(2'R,3S,4R,5'R) 4'-(3-Bromo-Phenyl)-6-Chloro-2'-(2,2-dimethyl-Propyl)-2-Oxo-1,2-Dihydro-Spiro[Indole-3,3'-Pyrrolidine]-5'-Carboxylic Acid [2-(4-Methyl-Piperazin-1-yl)-2-Oxo-Ethyl]-Amide (KE-67)

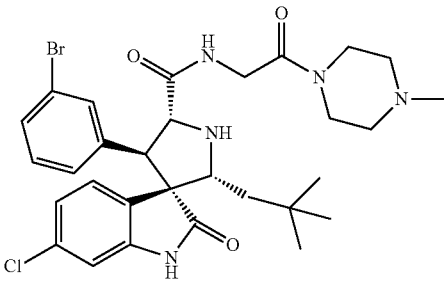 [SMILES: CN1CCN(C(=O)CNC(=O)[C@@H]2N[C@H](CC(C)(C)C)[C@]3(C(=O)Nc4cc(Cl)ccc43)[C@H]2c2cccc(Br)c2)CC1]

$^1$H NMR (300 MHz, CDCl$_3$), δ 8.46 (br, 1H), 7.90 (br, 1H), 7.31~7.23 (m, 2H), 7.14~7.07 (m, 2H), 6.94 (d, J=1.79 Hz, 1H), 6.75 (dd, J=1.86, 8.10 Hz, 1H), 4.45 (d, J=11 Hz, 1H), 4.22~4.15 (m, 1H), 4.03~3.95 (m, 1H), 3.87~3.83 (m, 1H), 3.73~3.65 (m, 3H), 3.43 (m, 2H), 2.44 (m, 4H), 2.32 (s, 3H), 1.85 (m, 1H), 0.97~0.92 (m, 1H), 0.89 (s, 9H).

Example 96

(2'R,3S,4S,5'R) 6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (2-Pyrrolidin-1-yl-Ethyl)-Amide (MDM2-DQ-120)

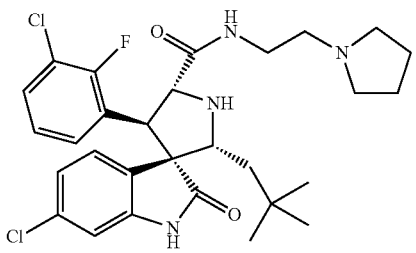 [SMILES: CC(C)(C)C[C@H]1N[C@@H](C(=O)NCCN2CCCC2)[C@H](c2cccc(Cl)c2F)[C@@]12C(=O)Nc1cc(Cl)ccc12]

$^1$H NMR (300 MHz, CDCl$_3$), δ 7.50 (br, 1H), 7.41 (m, 1H), 7.28 (m, 1H), 7.10 (m, 1H), 6.85 (d, J=1.54 Hz, 1H), 6.67 (dd, J=1.54, 7.61 Hz, 1H), 6.33 (d, J=8.17 Hz, 1H), 4.45 (d, J=8.40 Hz, 1H), 4.13 (dd, J=8.40, 1.54 Hz, 1H), 3.49~3.35 (m, 3H), 2.78 (m, 1H), 2.67 (m, 5H), 1.80 (m, 4H), 1.53 (dd, J=9.60, 14.40 Hz, 1H), 0.93 (m, 1H), 0.81 (s, 9H).

Example 97

(2'R,3S,4S,5'R) 6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (2-Piperidin-1-yl-Ethyl)-Amide (MDM2-DQ-121)

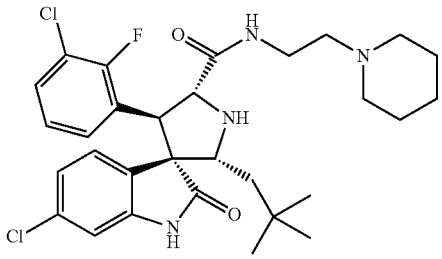 [SMILES: CC(C)(C)C[C@H]1N[C@@H](C(=O)NCCN2CCCCC2)[C@H](c2cccc(Cl)c2F)[C@@]12C(=O)Nc1cc(Cl)ccc12]

$^1$H NMR (300 MHz, CDCl$_3$), δ 9.70 (br, 1H), 8.50 (br, 1H), 7.47 (m, 1H), 7.28 (m, 1H), 7.14 (m, 1H), 6.97 (s, 1H), 6.61 (d, J=8.41 Hz, 1H), 5.88 (d, J=8.10 Hz, 1H), 4.90 (br, 1H), 4.42 (d, J=8.14 Hz, 1H), 4.17 (d, J=5.4 Hz, 1H), 3.69 (m, 2H), 3.53 (m, 2H), 3.33 (m, 4H), 1.90~1.53 (m, 7H), 0.93 (m, 1H), 0.82 (s, 9H).

Example 98

(2'R,3S,4S,5'R) 6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid [2-(1-Methyl-Piperidin-4-yl)-Ethyl]-Amide (MDM2-DQ-122)

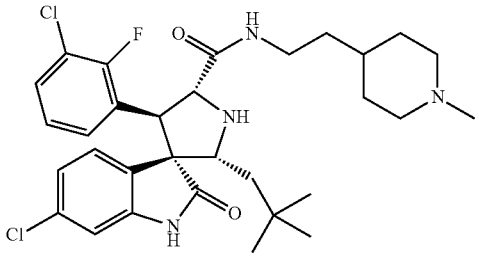 [SMILES: CN1CCC(CCNC(=O)[C@@H]2N[C@H](CC(C)(C)C)[C@]3(C(=O)Nc4cc(Cl)ccc43)[C@H]2c2cccc(Cl)c2F)CC1]

$^1$H NMR (300 MHz, CDCl$_3$), δ 7.41-7.22 (m, 3H), 7.07 (m, 2H), 6.81 (d, J=1.82 Hz, 1H), 6.67 (dd, J=8.10, 1.83 Hz, 1H), 6.24 (d, J=8.10 Hz, 1H), 4.41 (d, J=7.83 Hz, 1H), 4.05 (d, J=7.83 Hz, 1H), 3.51 (m, 1H), 3.33 (m, 2H), 2.93 (m, 2H), 2.32 (s, 3H), 2.02 (m, 3H), 1.72 (m, 2H), 1.53 (m, 3H), 1.35 (m, 3H), 0.93 (m, 1H), 0.82 (s, 9H).

Example 99

(2'R,3S,4S,5'R) 6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (2-Piperidin-4-yl-Ethyl)-Amide (MDM2-DQ-123)

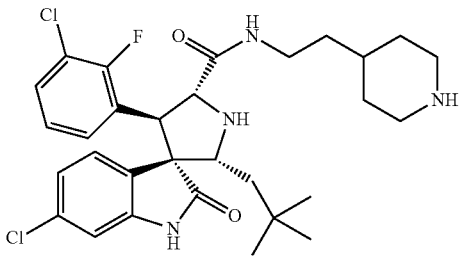 [SMILES: CC(C)(C)C[C@H]1N[C@@H](C(=O)NCCC2CCNCC2)[C@H](c2cccc(Cl)c2F)[C@@]12C(=O)Nc1cc(Cl)ccc12]

$^1$H NMR (300 MHz, CDCl$_3$), δ 7.34 (m, 1H), 7.20 (m, 1H), 7.07 (m, 2H), 6.80 (d, J=1.23 Hz, 1H), 6.64 (dd, J=8.11, 1.83 Hz, 1H), 6.24 (d, J=8.11 Hz, 1H), 4.41 (d, J=7.81 Hz, 1H), 4.05 (d, J=7.81 Hz, 1H), 3.45 (m, 1H), 3.32 (m, 2H), 2.86 (m, 2H), 1.92 (m, 3H), 1.48 (m, 3H), 1.28 (m, 3H), 0.93 (m, 2H), 0.80 (s, 9H).

Example 100

(2'R,3S,4S,5'R) 6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (4-Morpholin-4-yl-Butyl)-Amide (MDM2-119)

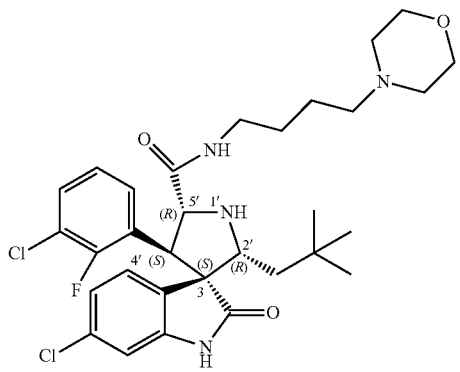

$[\alpha]^{25}_D$ 2.6 (c, 0.5 CHCl$_3$), $^1$H NMR (300 MHz, CDCl$_3$), λ7.82 (br, 1H), 7.34 (m, 1H), 7.24 (dt, J=1.43, 6.90 Hz, 1H), 7.10~7.05 (m, 2H), 6.83 (d, J=1.80 Hz, 1H), 6.68 (dd, J=1.86, 8.11 Hz, 1H), 6.26 (d, J=8.14 Hz, 1H), 4.42 (d, J=7.80 Hz, 1H), 4.07 (d, J=7.74 Hz, 1H), 3.73 (t, J=7.62 Hz, 4H) 3.48 (d, J=9.16 Hz, 1H), 3.34~3.20 (m, 2H), 2.45~2.31 (m, 6H), 1.58~1.47 (m, 5H), 0.92~0.88 (m, 1H), 0.82 (s, 9H); $^{13}$C NMR (75 MHz, CDCl$_3$), δ 180.57, 172.06, 142.60, 134.37, 130.01, 126.36, 125.66, 122.35, 110.52, 67.33, 66.67, 65.90, 62.83, 58.89, 54.04, 43.76, 39.53, 30.56, 30.21, 27.86, 24.16.

Example 101

(2'R,3S,4S,5'R) 6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (2-Cyclohexyl-Ethyl)-Amide (MDM2-DQ-125)

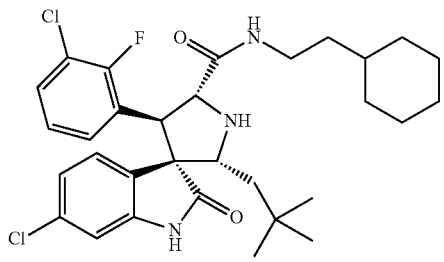

$^1$H NMR (300 MHz, CDCl$_3$), δ 8.37 (m, 1H), 7.35 (m, 1H), 7.23 (m, 1H), 7.06 (m, 2H), 6.86 (s, 1H), 6.68 (d, J=8.11 Hz, 1H), 6.30 (d, J=8.12 Hz, 1H), 4.46 (m, 1H), 4.12 (m, 1H), 3.48 (m, 1H), 3.31 (m, 2H), 2.38 (m, 1H), 1.67 (m, 5H), 1.29 (m, 3H), 1.17 (m, 4H), 0.91 (m, 2H), 0.81 (s, 9H).

Example 102

(2'R,3S,4S,5'R) 6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid [2-(4-Methyl-Piperazin-1-yl)-Ethyl]-Amide (MDM2-DQ-126)

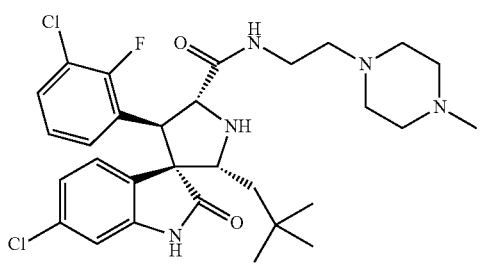 [SMILES: CN1CCN(CCNC(=O)[C@@H]2N[C@H](CC(C)(C)C)[C@]3(C(=O)Nc4cc(Cl)ccc43)[C@H]2c2cccc(Cl)c2F)CC1]

$^1$H NMR (300 MHz, D$_2$O), δ 7.36 (m, 1H), 7.19 (m, 1H), 7.05 (m, 2H), 6.77 (s, 1H), 6.50 (d, J=7.80 Hz, 1H), 6.26 (d, J=7.80 Hz, 1H), 4.46 (d, J=7.51 Hz, 1H), 4.37 (d, J=7.50 Hz, 1H), 4.05 (m, 1H), 3.60~3.21 (m, 12H), 2.90 (s, 3H), 1.83 (m, 1H), 0.98 (m, 1H), 0.89 (s, 9H).

Example 103

(2'R,3S,4S,5'R) 6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid [2-(4-Ethyl-Piperazin-1-YL)-Ethyl]-Amide (MDM2-DQ-129)

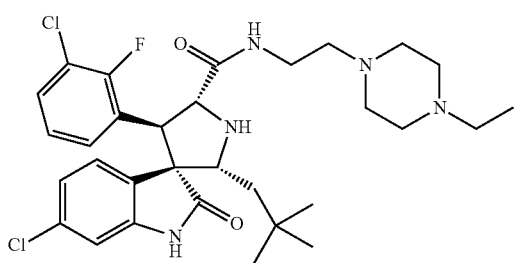 [SMILES: CCN1CCN(CCNC(=O)[C@@H]2N[C@H](CC(C)(C)C)[C@]3(C(=O)Nc4cc(Cl)ccc43)[C@H]2c2cccc(Cl)c2F)CC1]

$^1$H NMR (300 MHz, CDCl$_3$), δ 9.46 (br, 1H), 7.70 (br, 1H), 7.50 (m, 1H), 7.26 (m, 1H), 7.12 (m, 1H), 6.94 (d, J=1.56 Hz, 1H), 6.61 (dd, J=8.10, 1.80 Hz, 1H), 6.10 (d, J=8.10 Hz, 1H), 4.51 (d, J=6.30 Hz, 1H), 4.12 (d, J=6.30 Hz, 1H), 4.05 (m, 1H), 3.53-2.66 (m, 16H), 1.35 (t, J=7.2 Hz, 3H), 0.92 (m, 1H), 0.80 (s, 9H).

Example 104

(2'R,3S,4S,5'R) 6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid [2-(4-Isopropyl-Piperazin-1-yl)-Ethyl]-Amide (MDM2-D Q-130)

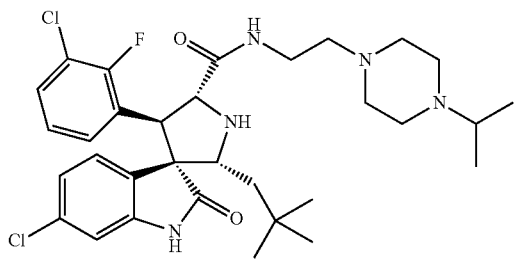

$^1$H NMR (300 MHz, CDCl$_3$), δ 9.80 (br, 1H), 7.88 (br, 1H), 7.52 (m, 1H), 7.24 (m, 1H), 7.13 (m, 1H), 6.97 (s, 1H), 6.61 (d, J=8.10 Hz, 1H), 6.08 (d, J=8.10 Hz, 1H), 4.63 (m, 1H), 4.17 (m, 1H), 3.61 (m, 1H), 3.59-2.60 (m, 14H), 1.55 (m, 1H), 1.35 (d, J=6.3 Hz, 6H), 0.92 (m, 1H), 0.80 (s, 9H).

Example 105

(Racemic) 6-Chloro-4'-(3-Chloro-2-Fluoro-Phenyl)-2'-(2,2-Dimethyl-Propyl)-1'-Methyl-2-Oxo-1,2-Dihydro-Spiro[Indole-3,3'-Pyrrolidine]-5'-Carboxylic Acid (2-Morpholin-4-yl-Ethyl)-Amide (KE-100)

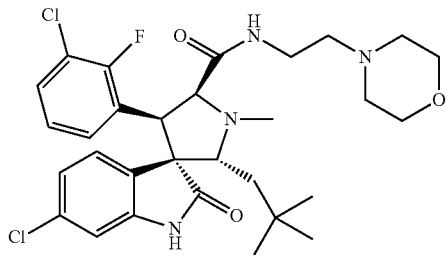 [SMILES: CN1[C@H](C(=O)NCCN2CCOCC2)[C@H](c2cccc(Cl)c2F)[C@@]2(C(=O)Nc3cc(Cl)ccc32)[C@H]1CC(C)(C)C]

$^1$H NMR (300 MHz, CDCl$_3$), δ 7.93~7.85 (m, 2H), 7.38~7.30 (m, 2H), 7.02 (t, J=7.92 Hz, 1H), 6.83 (d, J=1.86 Hz, 1H), 6.20 (dd, J=1.91, 8.31 Hz, 1H), 5.61 (d, J=8.16 Hz, 1H), 4.70 (d, J=7.86 Hz, 1H), 4.39 (d, J=7.83 Hz, 1H), 3.90 (d, J=7.31 Hz, 1H), 3.78~3.75 (m, 4H), 3.34~3.24 (m, 2H), 2.74 (s, 3H), 2.52~2.48 (m, 6H), 2.01~1.94 (m, 1H), 0.79 (s, 9H), 0.71~0.67 (m, 1H); $^{13}$C NMR (75 MHz, CDCl$_3$), δ 179.72, 171.31, 142.57, 134.78, 130.29, 127.80, 127.34, 125.74, 124.83, 123.95, 122.07, 110.53, 74.22, 67.50, 65.09, 63.32, 57.11, 53.69, 45.13, 39.55, 37.30, 35.28, 30.67, 30.00.

Example 106

(Racemic) 6-Chloro-4'-(3-Chloro-2-Fluoro-Phenyl)-2'-(2,2-Dimethyl-Propyl)-1'-Methyl-2-Oxo-1,2-Dihydro-Spiro[Indole-3,3'-Pyrrolidine]-5'-Carboxylic Acid (3-Morpholin-4-yl-Propyl)-Amide

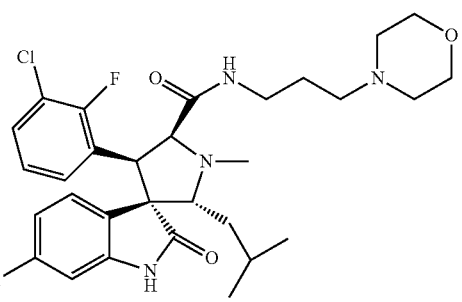

$^1$H NMR (300 MHz, CDCl$_3$), δ 8.37 (s, 1H), 8.22 (t, J=5.55 Hz, 1H), 7.42~7.28 (m, 2H), 7.03 (t, J=7.45 Hz, 1H), 6.81 (d, J=1.85 Hz, 1H), 6.63 (dd, J=1.89, 8.96 Hz, 1H), 5.87 (d, J=8.14 Hz, 1H), 4.65 (d, J=7.50 Hz, 1H), 4.37 (d, J=7.45 Hz, 1H), 4.05~4.01 (m, 1H), 3.77~3.74 (m, 4H), 3.30~3.24 (m, 2H), 2.69 (s, 3H), 2.46~2.39 (m, 6H), 1.89~1.66 (m, 2H), 1.42~1.38 (m, 1H), 0.99~0.87 (m, 2H), 0.76 (d, J=6.53 Hz, 3H), 0.69 (d, J=6.42 Hz, 3H).

Example 107

(2'R,3S,4'S,5'R) 6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid [3-(2-Hydroxy-Ethoxy)-Propyl]-Amide

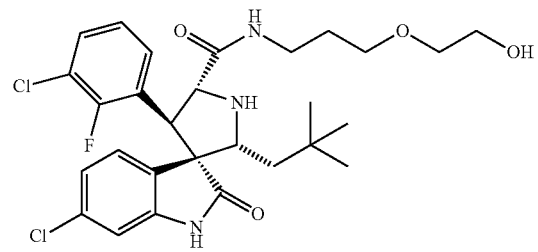 [SMILES: CC(C)(C)C[C@H]1N[C@@H](C(=O)NCCCOCCO)[C@H](c2cccc(Cl)c2F)[C@@]12C(=O)Nc1cc(Cl)ccc12]

$^1$H NMR (300 MHz, CDCl$_3$), δ 8.59 (s, 1H), 7.36-7.06 (m, 4H), 6.84 (d, J=1.8 Hz, 1H), 6.66 (dd, J1=7.5 Hz, J2=1.5 Hz, 1H), 6.25 (d, J=8.1 Hz, 1H), 4.43 (d, J=4.8 Hz, 1H), 4.10 (d, J=4.2 Hz, 1H), 3.79-3.41 (m, 11H), 1.84-1.81 (m, 2H), 1.51-1.46 (m, 1H), 0.93-0.89 (m, 1H), 0.81 (s, 9H); $^{13}$C NMR (75 MHz, CDCl$_3$), δ 181.12, 171.97, 142.93, 134.29, 129.95, 128.47, 127.66, 126.46, 125.57, 124.83, 124.78, 122.22, 110.71, 72.89, 70.62, 70.50, 69.73, 66.84, 66.01, 63.09, 62.11, 43.74, 37.57, 30.74, 30.34, 29.43.

Example 108

(2'R,3S,4'S,5'R) 6-Chloro-4'-(3-Chloro-2-Fluoro-Phenyl)-2'-(2,2-Dimethyl-Propyl)-5-Fluoro-2-Oxo-1,2-Dihydro-Spiro[Indole-3,3'-Pyrrolidine]-5'-Carboxylic Acid {2-[3-(2,2,2-Trifluoro-Ethyl)-5,6-Dihydro-8H-[1,2,4]Triazolo[4,3-A]Pyrazin-7-yl]-Ethyl}-Amide

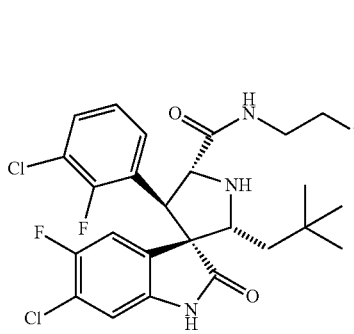

$^1$H NMR (300 MHz, CDCl$_3$), δ 8.98 (s, 1H), 7.58 (m, 1H), 7.29-7.03 (m, 3H), 6.89 (d, J=3.2 Hz, 1H), 6.02 (d, J=8.1 Hz, 1H), 4.42 (d, J=6.1 Hz, 1H), 4.08-4.03 (m, 4H), 3.96 (d, J=5.6 Hz, 1H), 3.93-3.78 (m, 1H), 3.71-3.42 (m, 2H), 3.19-3.12 (m, 1H), 3.02-2.74 (m, 3H), 2.10 (m, 2H), 1.54-1.48 (m, 1H), 1.24 (m, 1H), 0.96-0.92 (m, 1H), 0.86 (s, 9H); $^{13}$C NMR (75 MHz, CDCl$_3$), δ 180.35, 173.22, 152.60, 138.67, 130.37, 128.25, 127.65, 127.32, 125.07, 125.01, 113.37, 113.04, 111.81, 66.16, 65.77, 63.14, 56.24, 49.80, 48.22, 44.27, 43.99, 36.89, 34.92, 31.99, 30.17, 23.06, 14.54.

Example 109

(2'R,3S,3''S,4'S,5'R) 6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (3,4-Dihydroxy-Butyl)-Amide

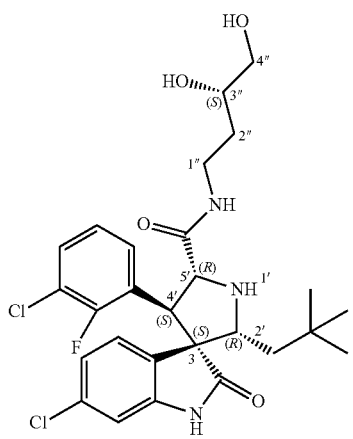

$^1$H NMR (300 MHz, CDCl$_3$), δ 8.72 (s, 1H), 7.31-7.21 (m, 3H), 7.08-6.93 (m, 1H), 6.83 (d, J=1.6 Hz, 1H), 6.66 (dd, J1=8.1 Hz, J2=1.8 Hz, 1H), 6.27 (d, J=8.01 Hz, 1H), 4.43 (d, J=7.6 Hz, 1H), 4.20-4.03 (m, 3H), 3.58-3.45 (m, 5H), 2.67 (m, 1H), 1.75-1.67 (m, 2H), 1.49-1.24 (m, 3H), 0.78 (s, 9H).

Example 110

(2'R,3S,4'S,5'R) 6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid [2-(2-Methoxy-Ethoxy)-Ethyl]-Amide

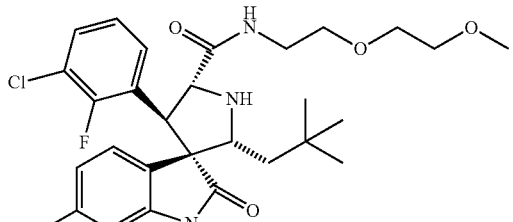

$^1$H NMR (300 MHz, CDCl$_3$), δ 8.64 (s, 1H), 7.32-7.19 (m, 3H), 7.08 (t, J=7.9 Hz, 1H), 6.85 (d, J=1.8 Hz, 1H), 6.68 (dd, J1=8.1 Hz, J=1.8 Hz, 1H), 6.32 (d, J=8.1 Hz, 1H), 4.46 (d, J=8.0 Hz, 1H), 4.12-4.03 (m, 1H), 3.62-3.41 (m, 9H), 3.38 (s, 3H), 2.85 (br, 1H), 1.52-1.47 (m, 1H), 0.98-0.89 (m, 1H), 0.82 (s, 9H); $^{13}$C NMR (75 MHz, CDCl$_3$), δ 181.41, 171.90, 143.07, 129.94, 128.50, 127.70, 126.97, 125.49, 124.85, 124.81, 123.18, 122.17, 121.94, 121.68, 110.81, 72.19, 70.56, 70.16, 67.34, 66.71, 63.46, 56.39, 51.89, 43.66, 39.18, 30.32, 29.29

Example 111

(2'R,3S,4'S, 5'R) 4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (3-Morpholin-4-yl-Propyl)-Amide

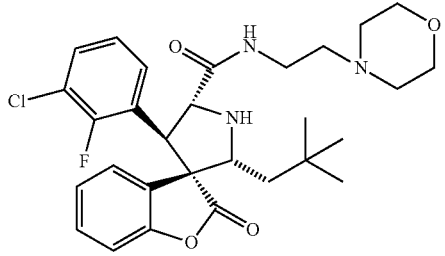 [SMILES: CC(C)(C)C[C@H]1N[C@@H](C(=O)NCCN2CCOCC2)[C@H](c2cccc(Cl)c2F)[C@@]12C(=O)Oc1ccccc12]

$^1$H NMR (300 MHz, CDCl$_3$), δ 7.45-7.04 (m, 7H), 6.83 (t, J=7.5 Hz, 1H), 6.34 (d, J=7.5 Hz, 1), 4.45 (d, J=5.8 Hz, 1H), 4.11 (d, J=5.9 Hz, 1H), 3.75-3.69 (m, 4H), 3.54 (d, J=4.8 Hz, 1H), 3.42-3.40 (m, 2H), 2.55-2.50 (m, 7H), 1.58-1.53 (m, 1H), 0.83 (s, 9H); $^{13}$C NMR (75 MHz, CDCl$_3$), δ 178.44, 171.32, 153.92, 153.58, 130.24, 129.61, 127.56, 125.13, 124.92, 124.40, 124.14, 122.12, 111.13, 110.92, 67.61, 67.33, 66.48, 62.19, 57.18, 53.83, 52.55, 44.72, 35.91, 30.63, 30.40, 30.19.

Example 112

(2'R,3S,4'S,5'R) 6-Chloro-4'-(3-Chloro-2-Fluoro-Phenyl)-2'-(2,2-Dimethyl-Propyl)-1'-Methyl-2-Oxo-1,2-Dihydro-Spiro[Indole-3,3'-Pyrrolidine]-5'-Carboxylic Acid [2-(2-Methoxy-Ethoxy)-Ethyl]-Amide

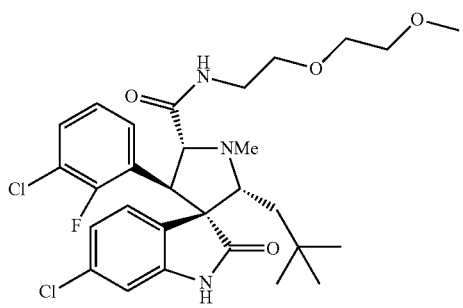 [SMILES: COCCOCCNC(=O)[C@H]1[C@H](c2cccc(Cl)c2F)[C@@]2(C(=O)Nc3cc(Cl)ccc32)[C@@H](CC(C)(C)C)N1C]

Under argon, to a solution of the compound of Example-110 (1 mmol) 20 mL $CH_3CN$, 0.5 mL 37% formalin and 1.1 mmol $NaBH_3CN$, 2 drops of HOAc were added. The resulting solution was stirred at room temperature for 2 hrs, then 50 mL ethyl acetate was added. The resulting mixture was washed with $NaHCO_3$ solution and brine and dried over $Na_2SO_4$. The solvent was removed and the residue was purified by column (yield, ~90%).

$^1$H NMR (300 MHz, $CDCl_3$) δ 8.01 (br, 1H), 7.52 (m, 1H), 7.28-7.02 (m, 2H), 6.85-6.52 (m, 3H), 4.15 (m, 1H), 3.87 (m, 1H), 3.72-3.51 (m, 8H), 3.44 (s, 3H), 2.96 (m, 1H), 2.52 (s, 3H), 2.16 (m, 1H), 1.61-1.48 (m, 2H), 0.58 (s, 9H).

Example 113

(2'R,3S,4'S, 5'R) 6-Chloro-4'-(3-Chloro-2-Fluoro-Phenyl)-2'-(2,2-Dimethyl-Propyl)-1'-Methyl-2-Oxo-1,2-Dihydro-Spiro[Indole-3,3'-Pyrrolidine]-5'-Carboxylic Acid (3-Morpholin-4-yl-Propyl)-Amide

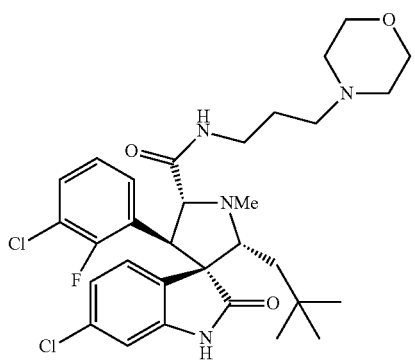 [SMILES: CN1[C@@H](C(=O)NCCCN2CCOCC2)[C@H](c2cccc(Cl)c2F)[C@@]2(C(=O)Nc3cc(Cl)ccc32)[C@H]1CC(C)(C)C]

The compound of example-113 was prepared via same procedure as Example-112.

$^1$H NMR (300 MHz, $CDCl_3$) δ 7.97 (br, 1H), 7.52 (m, 1H), 7.14-6.98 (m, 2H), 6.85-6.52 (m, 3H), 4.17 (m, 1H), 3.85-3.62 (m, 6H), 3.52-3.32 (m, 3H), 3.06 (m, 1H), 2.55-2.25 (m, 9H), 1.61-1.48 (m, 2H), 0.57 (s, 9H).

Example 114

(2'R,3S,4'S,5'R) 6-Chloro-4'-(3-Chloro-2-Fluoro-Phenyl)-2'-(2,2-Dimethyl-Propyl)-1'-Methyl-2-Oxo-1,2-Dihydro-Spiro[Indole-3,3'-Pyrrolidine]-5'-Carboxylic Acid (2-Morpholin-4-yl-Ethyl)-Amide

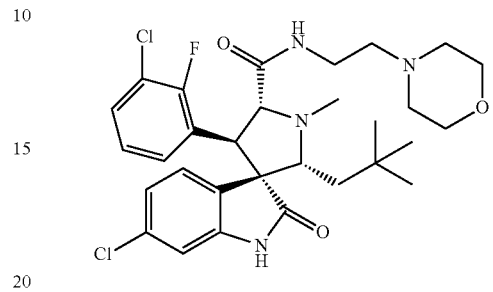

The compound of example-114 was prepared via same procedure as Example-112.

$^1$H NMR (300 MHz, $CDCl_3$), 67.62~7.30 (m, 2H), 7.21-6.92 (m, 3H), 6.92-6.50 (m, 3H), 4.17 (m, 1H), 3.79-3.36 (m, 5H), 3.46~3.31 (m, 2H), 2.92 (m, 1H), 2.65~2.30 (m, 8H), 1.95 (m, 1H), 1.80~1.45 (m, 2H), 0.58 (s, 9H).

Example 115

(2'R,3S,4'S,5'R) 6-Chloro-4'-(3-Chloro-2-Fluoro-Phenyl)-2'-(2,2-Dimethyl-Propyl)-5'-[2-(2-Methoxy-Ethoxy)-Ethylcarbamoyl]-2-Oxo-1,2-Dihydro-Spiro[Indole-3,3'-Pyrrolidine]-1'-Carboxylic Acid Methyl Ester

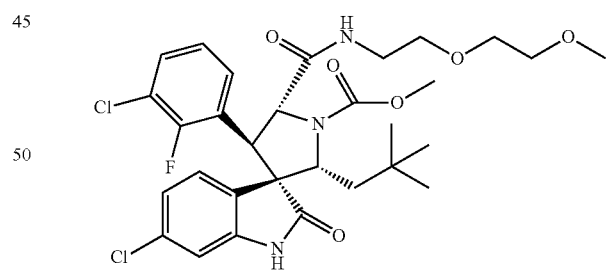

The compound of example 115 was prepared via same procedure as Example-112.

$^1$H NMR (300 MHz, $CDCl_3$), δ 7.89 (s, 1H), 7.26-7.20 (m, 2H), 7.05-7.03 (m, 1H), 6.84-6.82 (m, 2H), 4.85-4.82 (m, 1H), 4.11-4.05 (m, 1H), 3.97 (s, 3H), 3.81 (s, 3H), 3.58-3.47 (m, 8H), 2.59-2.44 (m, 3H), 1.81-1.75 (m, 1H), 1.34-1.30 (m, 1H), 0.85 (s, 9H); $^{13}$C NMR (75 MHz, $CDCl_3$), δ 171.62, 169.46, 151.15, 139.49, 138.03, 135.56, 131.03, 129.02, 127.68, 125.62, 124.88, 124.82, 124.62, 116.82, 72.19, 70.69, 70.16, 66.16, 63.24, 61.27, 59.43, 54.71, 53.62, 43.21, 39.92, 29.79, 23.06.

Example 116

(1"R,2"S,2'R,3S,4'S,5'R) 6-Chloro-4'-(3-Chloro-2-Fluoro-Phenyl)-2'-(2,2-Dimethyl-Propyl)-1'-(2-Hydroxy-1,2-Diphenyl-Ethyl)-5'-Hydroxymethyl-1H-Spiro[Indole-3,3'-Pyrrolidin]-2-One

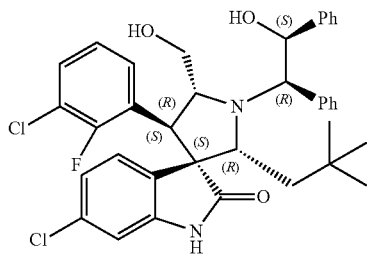

Under argon, to a 100 mL flask with stir bar was added (2S,3R)-2,3,5,6-tetrahydro-2,3-diphenyl-1,4-oxazin-6-one (1.0 g, 3.96 mmol), 3-E-(2-fluoro-3-chloro)-benzylidene-6-chloro-1,3-dihydro-indol-2-one (4.75 mmol), 2 g freshly activated 4 Å molecular sieves, 3,3-dimethyl-butyraldehyde (4.75 mmol) and toluene (50 mL). The mixture was heated to 70° C. and kept at that temperature for 5 hours. The mixture was cooled to room temperature and the molecular sieves were filtered off. The solvent was removed in vacuo and the residue was purified by chromatography to yield the 1,3-dipolar product.

The 1,3-dipolar product (2.0 mmol) obtained was dissolved in ethanol/HCl (10 mL) and the resulting solution was refluxed overnight. The solvent was removed in vacuo and the residue was neutralized with NaHCO$_3$/H$_2$O and extracted with ethyl acetate. The organic phase was dried over Na$_2$SO$_4$. The solvent was removed in vacuo and the residue was dissolved in 20 mL ethanol and 10 mmol NaBH$_4$ was added very carefully. The resulting mixture was refluxed overnight. The solvent was removed in vacuo and the residue was treated with NaOH/H$_2$O and extracted with ethyl acetate. The organic phase was dried over Na$_2$SO$_4$. The solvent was removed in vacuo and the residue was purified by chromatography to yield the product.

$^1$H NMR (300 MHz, CDCl$_3$), δ 7.60~7.34 (m, 11H), 7.14~7.09 (m, 1H), 7.04~6.93 (m, 2H), 6.82 (t, J=7.98 Hz, 1H), 6.57 (d, J=1.82 Hz, 1H), 5.38 (d, J=8.61 Hz, 1H), 4.47 (d, J=8.40 Hz, 1H), 3.93 (dd, J=2.6, 12.0 Hz, 1H), 3.74 (d, J=9.21 Hz, 1H), 3.63 (d, J=11.30 Hz, 1H), 3.11 (t, J=9.60 Hz, 1H), 2.64 (s, 1H), 2.37 (d, J=9.18 Hz, 1H), 1.84~1.75 (m, 1H), 1.15 (d, J=14.44 Hz, 1H), 0.54 (s, 9H).

Example 117

(1"R,2"S,2'R,3S,4'S, 5'R) 5'-(Tert-Butyl-Dimethyl-Silanyloxymethyl)-6-Chloro-4'-(3-Chloro-2-Fluoro-Phenyl)-2'-(2,2-Dimethyl-Propyl)-1'-(2-Hydroxy-1,2-Diphenyl-Ethyl)-1H-Spiro[Indole-3,3'-Pyrrolidin]-2-One

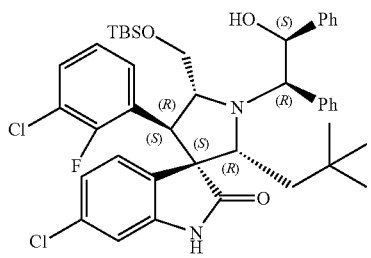

To a solution of compound 116 (1.0 mmol) in 10 mL DMF, TBDMSCl (1.1 mmol) and imidazole (1.1 mmol) were added. The resulting solution was stirred at room temperature for 2 hrs. The solvent was removed in vacuo and the residue was dissolved with ethyl acetate and the solution was washed by brine. The organic phase was dried over Na$_2$SO$_4$. The solvent was removed in vacuo and the residue was purified by chromatography to yield the product.

$^1$H NMR (300 MHz, CDCl$_3$), δ 7.62 (d, J=6.98 Hz, 2H), 7.48 (d, J=7.33 Hz, 2H), 7.38~7.06 (m, 11H), 6.82 (t, J=8.16 Hz, 1H), 6.65 (d, J=1.78 Hz, 1H), 5.54 (d, J=5.84 Hz, 1H), 4.54 (d, J=5.85 Hz, 1H), 4.23 (d, J=7.34 Hz, 1H), 4.10 (s, 1H), 3.82 (d, J=8.57 Hz, 1H), 3.73 (dd, J=3.36, 11.10 Hz, 1H), 3.49 (d, J=10.23 Hz, 1H), 3.22 (d, J=9.12 Hz, 1H), 1.89~1.81 (m, 1H), 1.34 (d, J=15.60 Hz, 1H), 0.91 (s, 9H), 0.52 (s, 9H), −0.05 (s, 3H), −0.12 (s, 3H).

Example 118

(1"R,2"S,2'R,3S,4'S,5'R) 2,2-Dimethyl-Propionic Acid 2-[6-Chloro-4'-(3-Chloro-2-Fluoro-Phenyl)-2'-(2,2-Dimethyl-Propyl)-5'-Hydroxymethyl-2-Oxo-1,2-Dihydro-Spiro[Indole-3,3'-Pyrrolidin]-1'-yl]-1,2-Diphenyl-Ethyl Ester

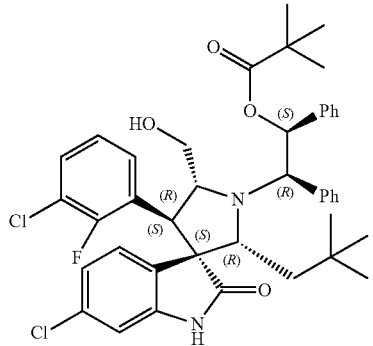

To a solution of compound 116 (1.0 mmol) in 10 mL CH$_2$Cl$_2$, trimethyl acetyl chloride (1.5 mmol) and diisopropyl ethylamine (2.0 mmol) was added and the resulting solution was stirred at room temperature overnight. The solvent was removed in vacuo and the residue was dissolved with ethyl acetate. HCl (1 mL) was added to the organic phase and the resulting mixture was stirred at room temperature for 2 hrs. Then 5 mL NaHCO$_3$/H$_2$O was added and the two phases were separated. The organic phase was dried over Na$_2$SO$_4$. The solvent was removed in vacuo and the residue was purified by chromatography to yield the product.

$^1$H NMR (300 MHz, CDCl$_3$), δ 7.59~7.15 (m, 15H), 6.84~6.82 (m, 2H), 5.40 (d, J=8.10 Hz, 1H), 4.48 (d, J=8.31 Hz, 1H), 8.18~8.10 (m, 1H), 3.94 (dd, J=2.52, 11.87 Hz, 1H), 3.77 (d, J=8.72 Hz, 1H), 3.56 (d, J=10.02 Hz, 1H), 3.16 (d, J=11.80 Hz, 1H), 1.66~1.57 (m, 1H), 1.30~1.28 (m, 1H), 1.15 (s, 9H), 0.56 (s, 9H).

Example 119

(1"R,2"S,2'R,3S,4'S,5'R) 2,2-Dimethyl-Propionic Acid 2-[5'-Bromomethyl-6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidin]-1'-yl]-1,2-Diphenyl-Ethyl Ester

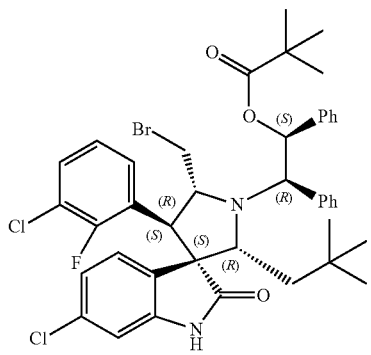

To a solution of compound 118 (1.0 mmol) in 10 mL CH$_2$Cl$_2$, CBr$_4$ (1.5 mmol) and Ph$_3$P (1.5 mmol) was added and the resulting solution was stirred at room temperature for 6 hrs. The solvent was removed in vacuo and the residue was purified by chromatography to yield the product.

$^1$H NMR (300 MHz, CDCl$_3$), δ 7.64 (d, J=6.69 Hz, 2H), 7.50 (d, J=7.20 Hz, 2H), 7.39~6.84 (m, 13H), 5.42 (d, J=7.40 Hz, 1H), 4.53 (d, J=6.90 Hz, 1H), 4.19 (d, J=9.00 Hz, 1H), 3.79 (d, J=8.61 Hz, 1H), 3.63~3.58 (m, 2H), 3.23 (s, 1H), 1.57~1.54 (m, 1H), 1.36~1.30 (m, 1H), 1.25 (s, 9H), 0.54 (s, 9H).

Example 120

(1"R,2"S,2'R,3S,4'S,5'R) 6-Chloro-4'-(3-Chloro-2-Fluoro-Phenyl)-2'-(2,2-Dimethyl-Propyl)-1'-(2-Hydroxy-1,2-Diphenyl-Ethyl)-5'-(2-Morpholin-4-yl-Ethoxymethyl)-1H-Spiro[Indole-3,3'-Pyrrolidin]-2-One

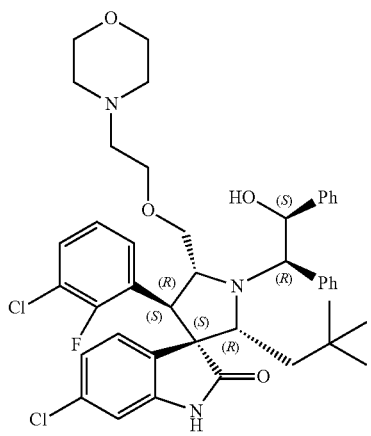

To a solution of 2-morpholin-4-yl-ethanol (10 mmol) in 10 mL dry THF, NaH (10 mmol) was added and the resulting mixture was stirred at room temperature for 2 hrs. Then compound 119 (1 mmol) was added and the resulting mixture was stirred at room temperature overnight. The solvent was removed in vacuo and the residue was dissolved with ethyl acetate and the solution was washed with brine. The organic phase was dried over Na$_2$SO$_4$ The solvent was removed in vacuo and the residue was purified by chromatography to yield the product.

$^1$H NMR (300 MHz, CDCl$_3$), δ 7.67 (d, J=7.05 Hz, 2H), 7.50 (d, J=7.38 Hz, 2H), 7.45~7.07 (m, 11H), 6.83 (t, J=7.94 Hz, 1H), 6.64 (d, J=1.79 Hz, 1H), 5.48 (d, J=5.68 Hz, 1H), 4.53 (d, J=5.82 Hz, 1H), 4.20 (d, J=10.61 Hz, 1H), 4.10 (s, 1H), 3.85 (d, J=5.66 Hz, 1H), 3.74~3.40 (m, 8H), 3.00 (dd, J=2.25, 9.60 Hz, 1H), 2.61~2.49 (m, 6H), 1.91~1.84 (m, 1H), 1.35~1.30 (m, 1H), 0.55 (s, 9H).

Example 121

(2'R,3S,4'S,5'R) 6-Chloro-4'-(3-Chloro-2-Fluoro-Phenyl)-2'-(2,2-Dimethyl-Propyl)-5'-(2-Morpholin-4-yl-Ethoxymethyl)-1H-Spiro[Indole-3,3'-Pyrrolidin]-2-One

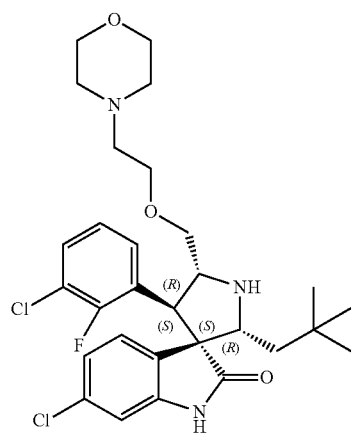

At 0° C., to a solution of compound 120 (2.0 mmol) in CH$_2$Cl$_2$-MeOH (10 mL, 1:1), Pb(OAc)$_4$ (1.34 g, 3.0 mmol) was added. The reaction was stirred at 0° C. for about 5-10 min, and the solution filtered through a short silica gel column. The solvent was removed in vacuo and the residue was purified by chromatography to yield the product.

$^1$H NMR (300 MHz, CDCl$_3$), δ 8.12 (s, 1H), 7.39~6.71 (m, 6H), 4.18~3.40 (m, 11H), 2.63~2.47 (m, 7H), 1.29~1.13 (m, 2H), 0.85 (s, 9H).

Example 122

(2'R,3S,4'S,5'R) 6-Chloro-4'-(3-Chloro-2-Fluoro-Phenyl)-2'-(2,2-Dimethyl-Propyl)-1'-Methyl-5'-(2-Morpholin-4-yl-Ethoxymethyl)-1H-Spiro[Indole-3,3'-Pyrrolidin]-2-One

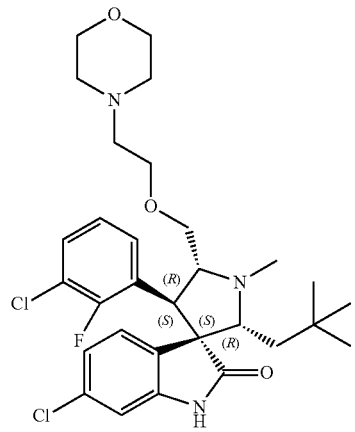

Compound 122 was obtained by a same procedure as example 112.

$^1$H NMR (300 MHz, CDCl$_3$), δ 7.50 (d, J=8.66 Hz, 1H), 7.28~7.17 (m, 3H), 7.02~6.88 (m, 1H), 6.88 (d, J=1.80 Hz, 1H), 5.02~4.80 (m, 1H), 3.96 (d, J=11.15 Hz, 1H), 3.68 (t, J=4.50 Hz, 4H), 3.57~3.53 (m, 2H), 3.40~3.32 (m, 2H), 3.03 (d, J=6.83 Hz, 1H), 2.55 (s, 3H), 2.48~2.40 (m, 6H), 1.76~1.68 (m, 1H), 1.47 (d, J=15.10 Hz, 1H), 0.61 (s, 9H).

Example 123

(2'R,3S,3"S,4'R,5'R) 6-Chloro-4'-(3-Chloro-Phenyl)-2'-(2,2-Dimethyl-Propyl)-2-Oxo-1,2-Dihydro-Spiro[Indole-3,3'-Pyrrolidine]-5'-Carboxylic Acid (3,4-Dihydroxy-Butyl)-Amide Hydrochloride

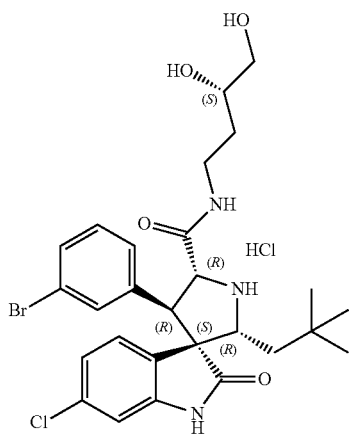

$^1$H NMR (300 MHz, CD$_3$OD), δ 8.46 (br, 1H), 7.50~7.38 (m, 2H), 7.30~7.14 (m, 4H), 6.92 (dd, J=1.93, 8.13 Hz, 1H), 6.80 (d, J=1.83 Hz, 1H), 5.08 (d, J=10.84 Hz, 1H), 4.30~4.26 (m, 1H), 4.20 (d, J=10.85 Hz, 1H), 3.51~3.31 (m, 8H), 2.05~2.00 (m, 1H), 1.64~1.46 (m, 3H), 0.85 (s, 9H); $^{13}$C NMR (75 MHz, CD$_3$OD), δ 178.78, 165.54, 143.64, 135.89, 135.44, 131.84, 131.77, 130.54, 127.53, 127.18, 125.57, 122.68, 122.27, 110.67, 69.67, 66.09, 63.31, 63.23, 61.13, 60.58, 56.20, 41.53, 36.90, 32.66, 29.85, 28.49; EIMS: 580.1 (M$^+$+1).

Example 124

(2'R,3S,3"S,4'R, 5'R) 6-Chloro-4'-(3-Chloro-Phenyl)-2'-(2,2-Dimethyl-Propyl)-5-Fluoro-2-Oxo-1,2-Dihydro-Spiro[Indole-3,3'-Pyrrolidine]-5'-Carboxylic Acid (3,4-Dihydroxy-Butyl)-Amide

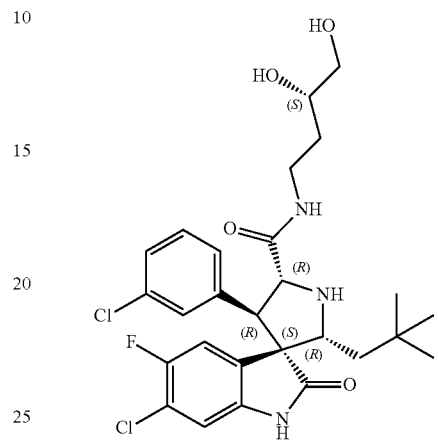

$^1$H NMR (300 MHz, CDCl$_3$), δ 9.34 (br, 1H), 7.70 (t, J=6.00 Hz, 1H), 7.27~7.12 (m, 3H), 7.00 (s, 1H), 6.90 (d, J=7.40 Hz, 1H), 6.78 (d, J=6.10 Hz, 1H), 5.84 (d, J=8.94 Hz, 1H), 4.36 (d, J=5.14 Hz, 1H), 3.80~3.47 (m, 7H), 1.70~1.98 (m, 2H), 1.52~1.44 (m, 1H), 0.94~0.90 (m, 1H), 0.83 (s, 9H); EIMS: 552.2 (M$^+$+1).

Example 125

(2'R,3S,3"S,4'R,5'R) 6-Chloro-4'-(3-Chloro-Phenyl)-2'-(2,2-Dimethyl-Propyl)-2-Oxo-1,2-Dihydro-Spiro[Indole-3,3'-Pyrrolidine]-5'-Carboxylic Acid (3-Hydroxy-4-Trityloxy-Butyl)-Amide

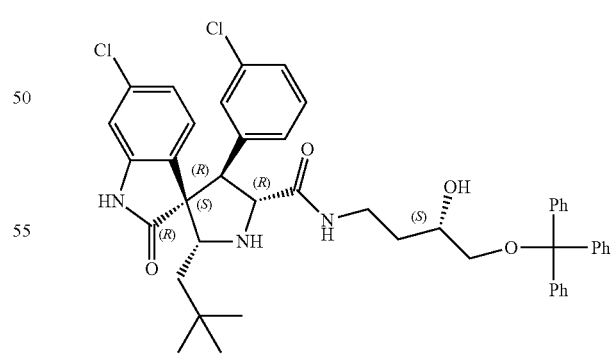

$^1$H NMR (300 MHz, CDCl$_3$), δ 8.46 (br, 1H), 7.46~7.23 (m, 15H), 7.18~7.09 (m, 3H), 6.90 (d, J=7.00 Hz, 1H), 6.80 (s, 1H), 6.69 (d, J=7.90 Hz, 1H), 6.19 (d, J=7.59 Hz, 1H), 4.33 (5.82 Hz, 1H), 3.88 (br, 1H), 3.83 (d, J=6.56 Hz, 1H), 3.65~3.55 (m, 2H), 3.34~3.10 (m, 4H), 2.71 (br, 1H), 1.73~1.48 (m, 3H), 0.96~0.91 (m, 1H), 0.84 (s, 9H).

Example 126

(2'R,3S,4'S,5'R) 6-Chloro-4'-(3-Chloro-2-Fluoro-Phenyl)-2'-(2,2-Dimethyl-Propyl)-5'-(Morpholine-4-Carbonyl)-1H-Spiro[Indole-3,3'-Pyrrolidin]-2-One

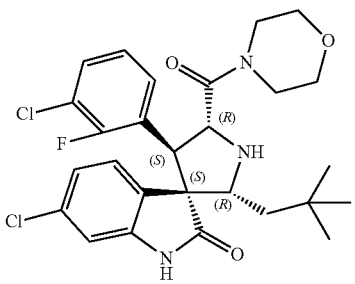

$^1$H NMR (300 MHz, CDCl$_3$), δ 8.39 (br, 1H), 7.27~7.13 (m, 2H), 7.05~6.99 (m, 1H), 6.87 (d, J=1.57 Hz, 1H), 6.72 (dd, J=1.43, 8.08 Hz, 1H), 6.49 (d, J=8.05 Hz, 1H), 4.61~4.54 (m, 1H), 4.39 (d, J=8.04 Hz, 1H), 3.80~3.45 (m, 8H), 2.97 (m, 1H), 1.80 (br, 1H), 1.51~1.42 (m, 1H), 0.90~0.87 (m, 1H), 0.84 (s, 9H); $^{13}$C NMR (75 MHz, CDCl$_3$), δ 181.47, 168.74, 142.90, 134.17, 130.24, 128.44, 128.25, 126.69, 125.37, 125.11, 122.38, 122.31, 110.75, 68.96, 67.26, 67.17, 64.38, 63.97, 52.84, 46.62, 43.21, 31.99, 30.58, 30.24.

Example 127

(2'R,3S,3"S,4'R,5'R) 6-Chloro-4'-(3-Chloro-Phenyl)-2'-(2,2-Dimethyl-Propyl)-2-Oxo-1,2-Dihydro-Spiro[Indole-3,3'-Pyrrolidine]-5'-Carboxylic Acid (3,4-Dihydroxyl)-Amide Hydrochloride

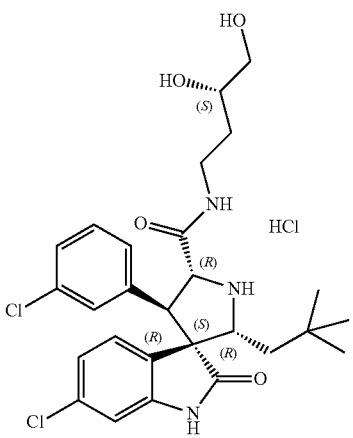

$^1$H NMR (300 MHz, CD$_3$OD), δ 8.46 (br, 1H), 7.26~7.15 (m, 6H), 6.92 (dd, J=1.83, 8.13 Hz, 1H), 6.80 (d, J=1.81 Hz, 1H), 5.13 (br, 1H), 5.09 (d, J=10.71 Hz, 1H), 4.30~4.18 (m, 2H), 3.50~3.30 (m, 7H), 2.07~2.00 (m, 1H), 1.65~1.45 (m, 3H), 0.84 (s, 9H); $^{13}$C NMR (75 MHz, CD$_3$OD), δ 178.76, 165.45, 143.66, 135.45, 134.68, 130.34, 128.88, 128.78, 127.13, 125.51, 122.28, 110.67, 69.67, 66.07, 63.30, 63.21, 61.06, 60.58, 56.18, 41.49, 37.05, 36.91, 32.64, 29.84, 28.48; EIMS: 534.2 (M$^+$+1).

Example 128

(2'R,3S,3"S,4'R,5'R) 6-Chloro-4'-(3-Chloro-2-Fluoro-Phenyl)-2'-(2,2-Dimethyl-Propyl)-5-Fluoro-2-Oxo-1,2-Dihydro-Spiro[Indole-3,3'-Pyrrolidine]-5'-Carboxylic Acid (3,4-Dihydroxy-Butyl)-Amide

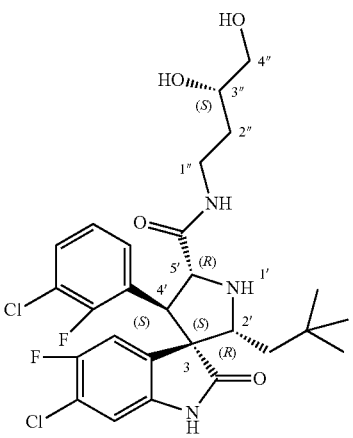

$^1$H NMR (300 MHz, DMSO-d$_6$), δ 10.44 (br, 1H), 8.11 (br, 1H), 7.73 (t, J=6.69 Hz, 1H), 7.44~7.15 (m, 2H), 6.88~6.82 (m, 2H), 4.29~4.28 (m, 3H), 3.94 (d, J=9.60 Hz, 1H), 3.32~3.00 (m, 4H), 2.60~2.50 (m, 1H), 1.52~1.17 (m, 3H), 0.82 (s, 9H). EIMS: 570.2 (M$^+$+1).

Example 129

(2'R,3S,3"S,4'R,5'R) 4'-(3-Bromo-Phenyl)-6-Chloro-2'-(2,2-Dimethyl-Propyl)-5-Fluoro-2-Oxo-1,2-Dihydro-Spiro[Indole-3,3'-Pyrrolidine]-5'-Carboxylic Acid (3,4-Dihydroxy-Butyl)-Amide

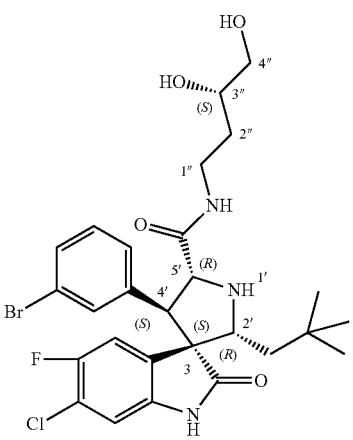

$^1$H NMR (300 MHz, CDCl$_3$), δ 9.47 (br, 1H), 7.72 (t, J=5.59 Hz, 1H), 7.37 (d, J=7.84 Hz, 1H), 7.18 (s, 1H), 7.11 (t, J=7.77 Hz, 1H), 6.95 (d, J=7.74 Hz, 1H), 6.78 (d, J=9.04 Hz, 1H), 5.85 (d, J=8.96 Hz, 1H), 4.60 (br, 1H), 4.35 (d, J=4.94 Hz, 1H), 3.85~3.40 (m, 8H), 1.75~1.65 (m, 2H), 1.51~1.43 (m, 1H), 0.90~0.88 (m, 1H), 0.83 (s, 9H); $^{13}$C NMR (75 MHz, CDCl$_3$), 180.62, 174.19, 155.61, 141.86, 138.55, 132.04, 131.33, 130.66, 127.12, 123.26, 121.14, 114.20, 111.91, 70.47, 67.14, 66.98, 65.20, 63.49, 55.96, 44.34, 36.97, 33.23, 30.55, 30.27.

Example 130

(2R,3S,3"S,4'R,5R) 6-Chloro-4'-(3-Chloro-2-Fluoro-Phenyl)-2'-(2,2-Dimethyl-Propyl)-2-Oxo-1,2-Dihydro-Spiro[Indole-3,3'-Pyrrolidine]-5'-Carboxylic Acid (4-Hydroxy-Butyl)-Amide

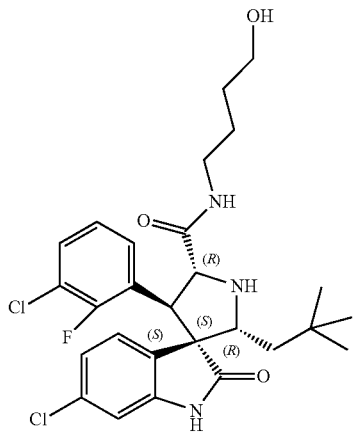

$^1$H NMR (300 MHz, CDCl$_3$), δ 9.63 (br, 1H), 7.84 (s, 1H), 7.47 (s, 1H), 7.23 (t, J=7.23 Hz, 1H), 7.09 (t, J=7.20 Hz, 1H), 6.91 (s, 1H), 6.65 (d, J=8.07 Hz, 1H), 6.22 (d, J=7.25 Hz, 1H), 4.61 (m, 1H), 4.12 (m, 1H), 3.65 (m, 3H), 3.48~3.25 (m, 4H), 1.65~1.50 (m, 5H), 0.91~0.90 (m, 1H), 0.86 (s, 9H).

Example 131

(2R,3S,3"S,4'R,5R) 6-Chloro-4'-(3-Chloro-4-Fluoro-Phenyl)-2'-(2,2-Dimethyl-Propyl)-2-Oxo-1,2-Dihydro-Spiro[Indole-3,3'-Pyrrolidine]-5'-Carboxylic Acid (3,4-Dihydroxy-Butyl)-Amide

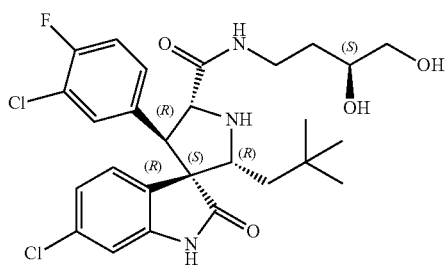

[α]$^{25}_D$, 71.1 (c, 1.0 MeOH); $^1$H NMR (300 MHz, CD$_3$COCD$_3$), δ 9.74 (s, 1H), 7.74 (t, J=5.8 Hz, 1H), 7.43 (dd, J=2.0, 7.1 Hz, 1H), 7.33-6.84 (m, 5H), 4.42 (d, J=8.4 Hz, 1H), 4.05-3.98 (m, 1H), 3.91 (d, J=8.1 Hz, 1H), 3.70-3.33 (m, 6H), 3.04 (br, 2H), 1.53-1.45 (m, 3H), 0.98-0.091 (m, 1H), 0.84 (s, 9H); $^{13}$C NMR (75 MHz, CD$_3$COCD$_3$), δ 180.40, 172.20, 158.73, 155.46, 144.00, 136.86, 133.30, 131.19, 129.97, 128.64, 126.92, 121.36, 109.91, 69.97, 67.33, 67.22, 66.73, 64.40, 58.92, 44.49, 36.39, 33.63, 29.40. ESIMS [M+Na]=574.1.

Example 132

Competitive Inhibition of P53-MDM2 Interaction

Figure 9:
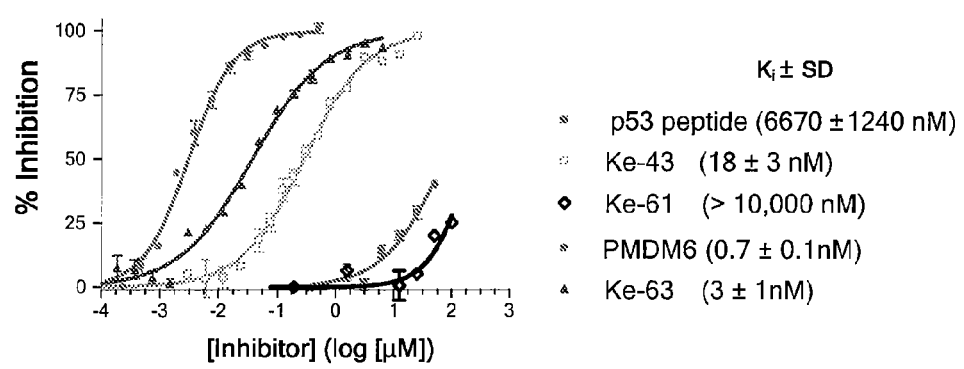
FIG. 9 shows competitive binding curves of several inhibitors of the p53-MDM2 interaction.

The FP binding assay described in Example 2 was used to test the ability of several synthesized compounds to inhibit the interaction between MDM2 and p53. Compounds Ke-43 (Example 41), Ke-61 (Example 65), PMDM6 (Example 2), and Ke-63 (Example 88) were tested against the natural p53 peptide (Example 2). Compounds Ke-43, PMDM6, and Ke-63 were shown to be more potent than the natural p53 peptide, with K, values in the low nM to sub-nM range (FIG. 9).

Example 133

Disruption of P53-MDM2 Interaction by MDM2 Inhibitors

Figure 10:
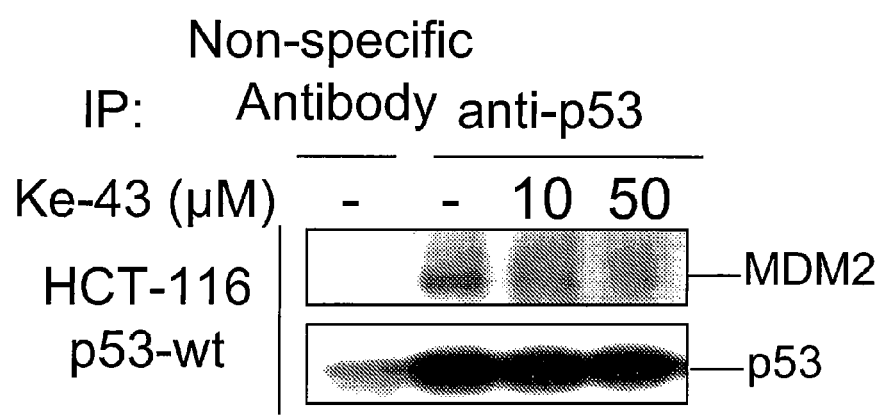
FIG. 10 shows the disruption of p53-MDM2 interaction by Ke-43.

Co-immunoprecipitation (Co-IP)/Western blotting assays were performed to assess the effects of Ke-43 on p53-MDM2 interaction. After harvesting and washing once with cold PBS, HCT116 colon cancer cells were lysed by sonication in cold Co-IP buffer (50 mM Tris (pH 7.5), 150 mM NaCl, 1 mM EDTA (pH 8.0), 0.5% NP-40) containing 1 mM phenylmethylsulfonyl fluoride and protease inhibitor cocktail. Sonicated lysates were then centrifuged at 12,000×g at 4° C. for 15 minutes. Supernatant containing 2 mg protein was incubated in the absence or presence of Ke-43 for 1 h at 4° C., followed by addition agarose beads, conjugated either with anti-p53 antibody (FL-393, Santa Cruz) or with a non-specific antibody. After mixing for 2 h at 4° C., the agarose beads were washed 3 times with cold Co-IP buffer, boiled in sample buffer followed by SDS-PAGE and the presence of p53 and MDM2 was detected by Western blotting with mouse monoclonal antibodies against p53 and MDM-2 proteins. Increasing concentrations of Ke-43 resulted in decreased immunopreciptiation of MDM2 by the anti-p53 antibody, indicating that Ke-43 disrupts the interaction between p53 and MDM2 (FIG. 10).

Example 134

Cell Growth Inhibition by MDM2 Inhibitors

Figure 11:
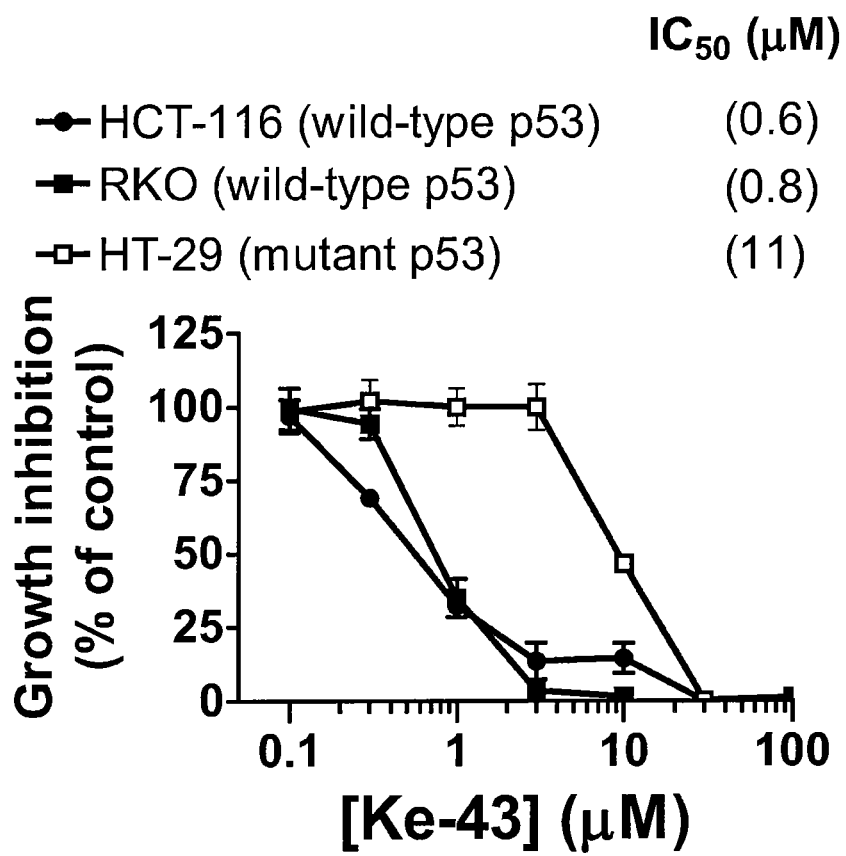
FIG. 11 shows the cell growth inhibition activity of Ke-43 in colon cancer cells with or without wild-type p53 and in normal cells.

RKO (wild-type p53), HCT116 (wild-type p53), and HT-29 (mutant p53) colon cancer cell lines were seeded in 96-well flat bottom cell culture plates at a density of 3–4×10$^3$ cells/well and incubated in the presence of compounds for 4 days. The rate of cell growth inhibition after treatment with increasing concentrations of the compounds was determined using WST-8 (2-(2-methoxy-4-nitrophenyl)-3-(4-nitrophenyl)-5-(2,4disulfophenyl)-2H-tetrazolium monosodium salt (Dojindo Molecular Technologies Inc., Gaithersburg, Md.). WST-8 was added at a final concentration of 10% to each well and the plates were incubated at 37° C. for 2-3 hrs. The absorbance of the samples was measured at 450 nm in a plate reader (Molecular Device-TECAN ULTRA). The concentration of the compounds that inhibited cell growth by 50% (IC$_{50}$) was calculated by comparing absorbance in the cells treated with the compounds with the untreated cells. Compound Ke-43 (examples 41) showed a potent growth inhibitory activity for cancer cells expressing wild-type p53 (FIG. 11). Notably, cancer cells expressing wild-type p53 showed greater than 18-fold (HCT116) and greater than 13-fold (RKO) specificity over cancer cells expressing mutant p53 (HT-29) (FIG. 11).

Example 135

Effects of MDM2 Inhibitors on Expression of P53 and its Target Gene Products MDM2 and P21

Figure 12:
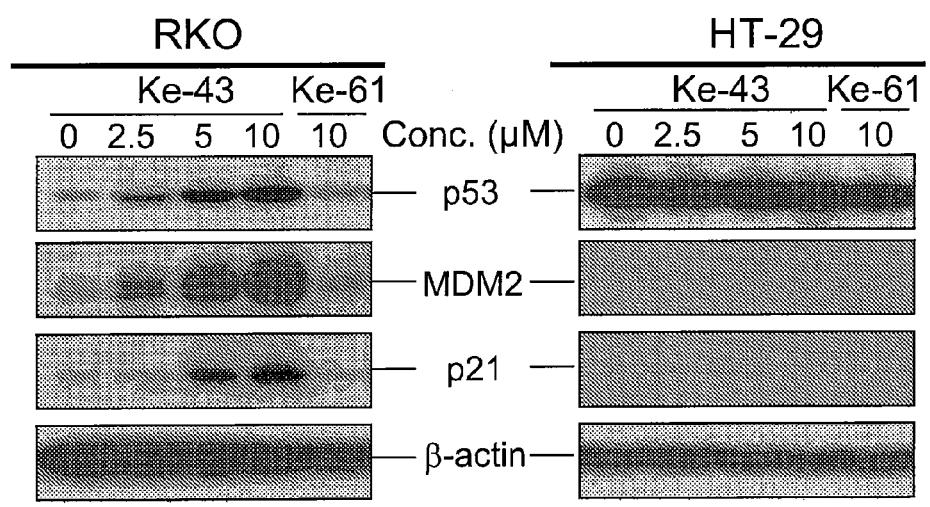
FIG. 12 shows Western blot analysis of the expression of p53 and its target gene products MDM2 and p21 in cancer cells in response to Ke-43.

Cancer cells were treated with test compounds or 0.1% DMSO for 24 hours. Cells were harvested by trypsinization and washed with cold phosphate buffer saline, pH 7.5 (Invitrogen, Carlsbad, Calif.). Cells were lysed for 30 minutes in ice-cold lysis buffer (50 mM Tris (pH 7.5), 150 mM NaCl, 1 mM EDTA (pH 8.0), 25 mM sodium fluoride, 1% NP-40 and 0.1% SDS) containing 2 mM sodium orthovanadate, 1 mM phenylmethylsulfonyl fluoride and protease inhibitor cocktail (Roche Applied Science, Indianapolis, Ind.). Next, cell extracts were centrifuged at 12,000×g at 4° C. for 10 minutes to obtain clarified lysates. Protein was estimated by Bio-Rad dye. Cell lysates containing 35 μg protein were resolved on a 4-20% tris-glycine gel (Invitrogen, Carlsbad, Calif.) and transferred onto poly(vinylidene difluoride) membranes. Immunodetection of proteins on the transfer membrane was performed by using anti-p53 (Ab-6, Oncogene Research Products, Boston, Mass.), anti-MDM2 (SMP14, Santa Cruz Biotechnology, Santa Cruz, Calif.) and anti-p21 (BD Biosciences, San Diego, Calif.) mouse monoclonal antibodies. Antibody to β-actin (Sigma, St Louis, Mo.) was used to assess the protein loading. When RKO (wild-type p53) and HT-29 (mutant p53) colon cancer cell lines were treated with Ke-43 (Example 41) for 24 hours, Ke-43 induced accumulation of p53 and its target gene-products only in RKO cells expressing wild-type p53 (FIG. 12).

Example 136

Cell Death and Apoptosis Induced by MDM2 Inhibitors

Figure 13:
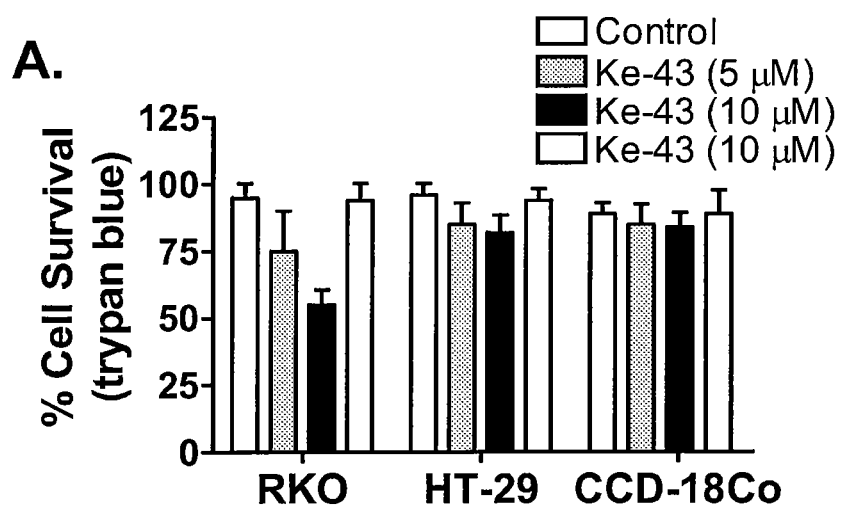
FIGS. 13A and 13B show cell death and apoptosis induced by Ke-43 and Ke-61 in cancer cells and normal cells.
Figure 13:
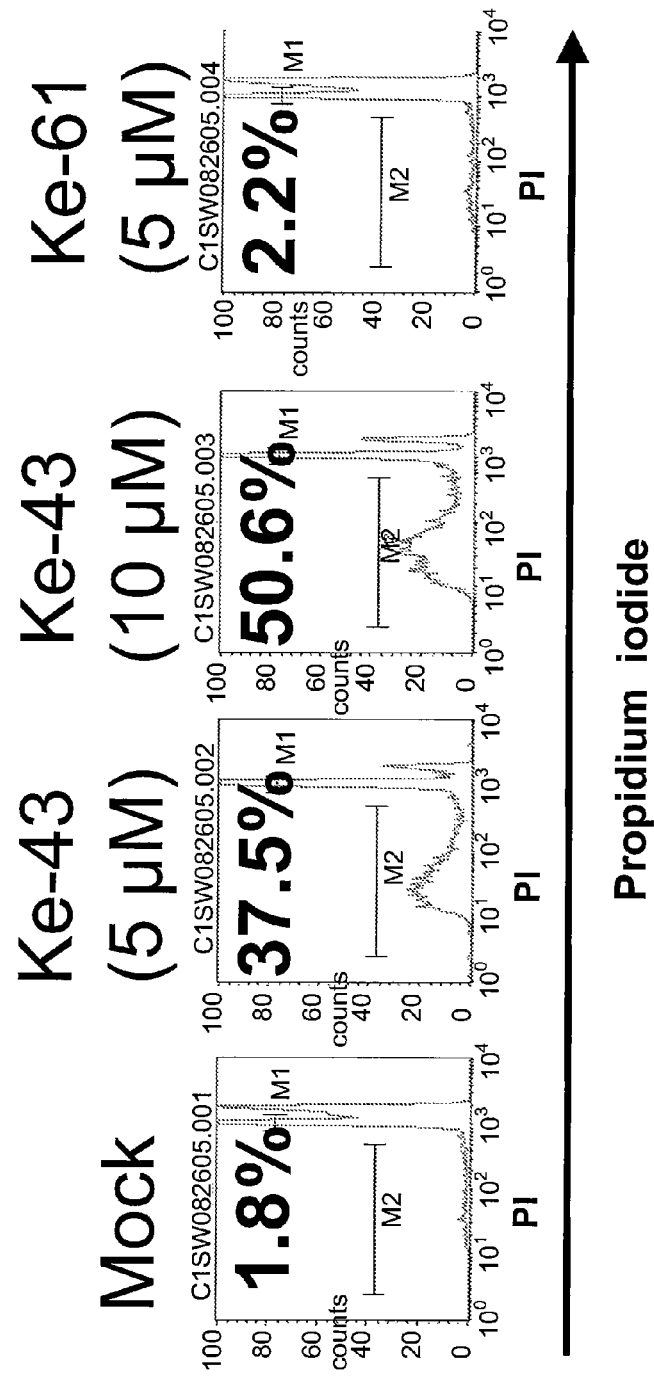
Figure 13:
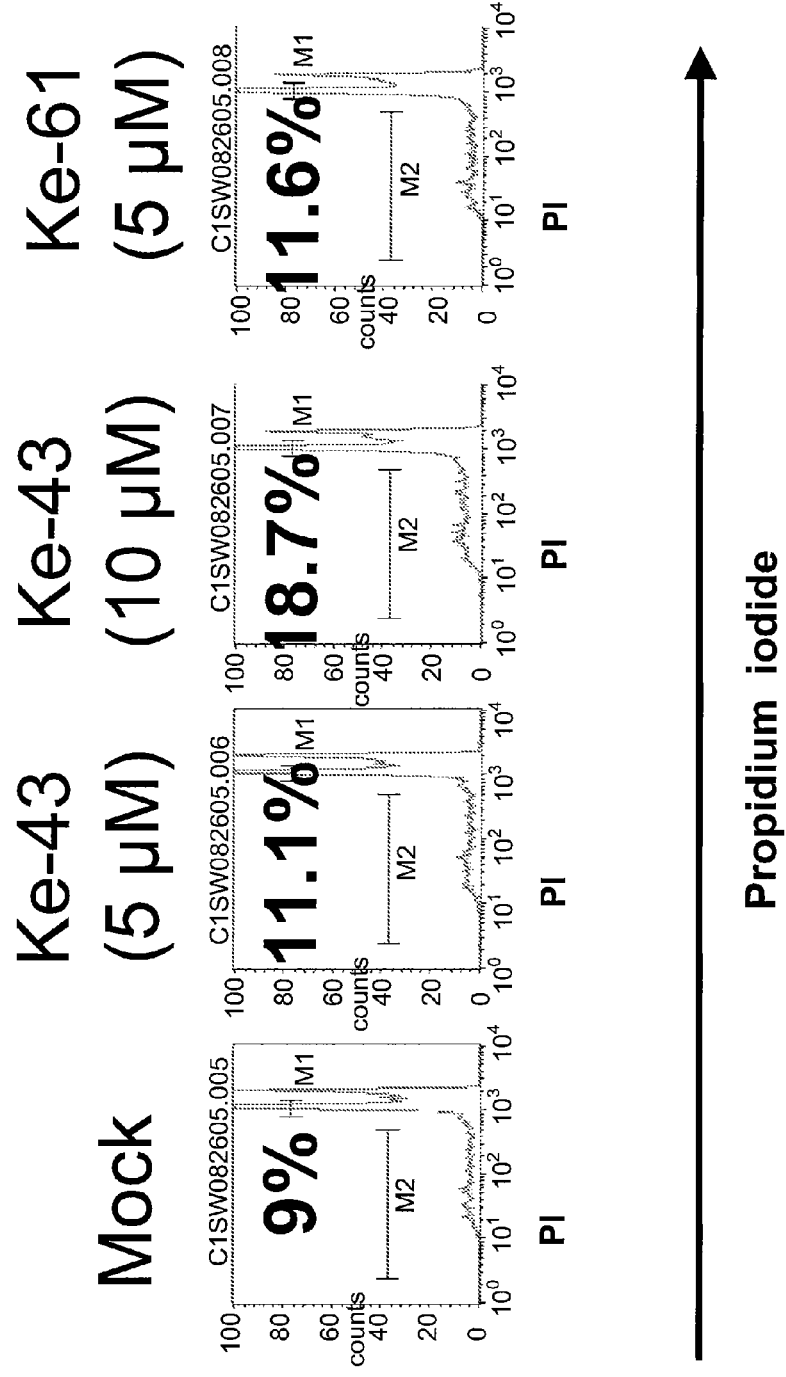
Figure 13:
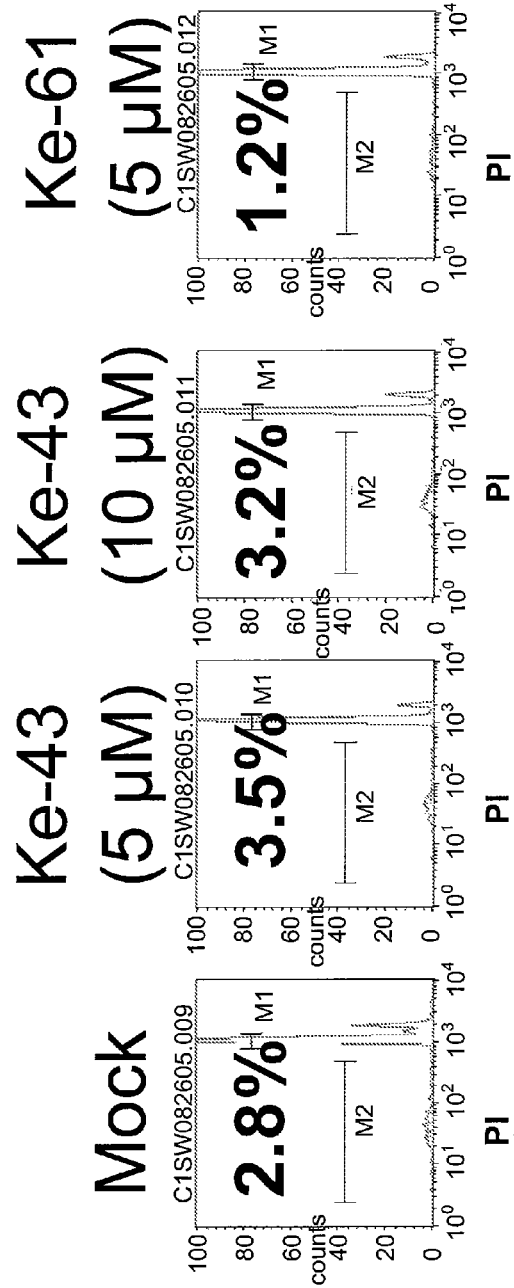

RKO (wild-type p53) and HT-29 (mutant p53) colon cancer cell lines and CCD-18Co normal colon fibroblast cells were treated with increasing doses of Ke-43 or Ke-61 for 4 days in 6-well Petri dishes. Trypan blue dye exclusion assays were performed to determine the ability of the inhibitors to induce cell death. After 4 days of treatment, floating and adherent cells were harvested and stained with 0.2% of trypan blue solution (Sigma, St Louis, Mo.). Each treatment was performed in triplicate and at least 100 cells were counted. Cells stained blue or morphologically unhealthy cells were scored as dead cells. To evaluate apoptosis, sub-diploid DNA content in cells treated with or without test inhibitors was analyzed by propidium iodide (PI) staining After washing once with cold PBS, cells were fixed in 70% ethanol for 1 day at −20° C. Ethanol-fixed cells were then washed twice with PBS and stained with a staining solution containing propidium iodide (PI) at 50 μg/ml and RNAse A at 100 μg/ml in PBS, for 20 minutes in dark at room temperature. Acquisition of cells and analysis of sub-diploid DNA content was performed by flow cytometry using CellQuest software. Only cancer cells expressing wild-type p53 underwent apoptosis in response to administration of Ke-43 (FIG. 13).

Example 137

Effect of MDM2 Inhibitors on Cell Cycle Progression of Colon Cancer Cells

Figure 14:
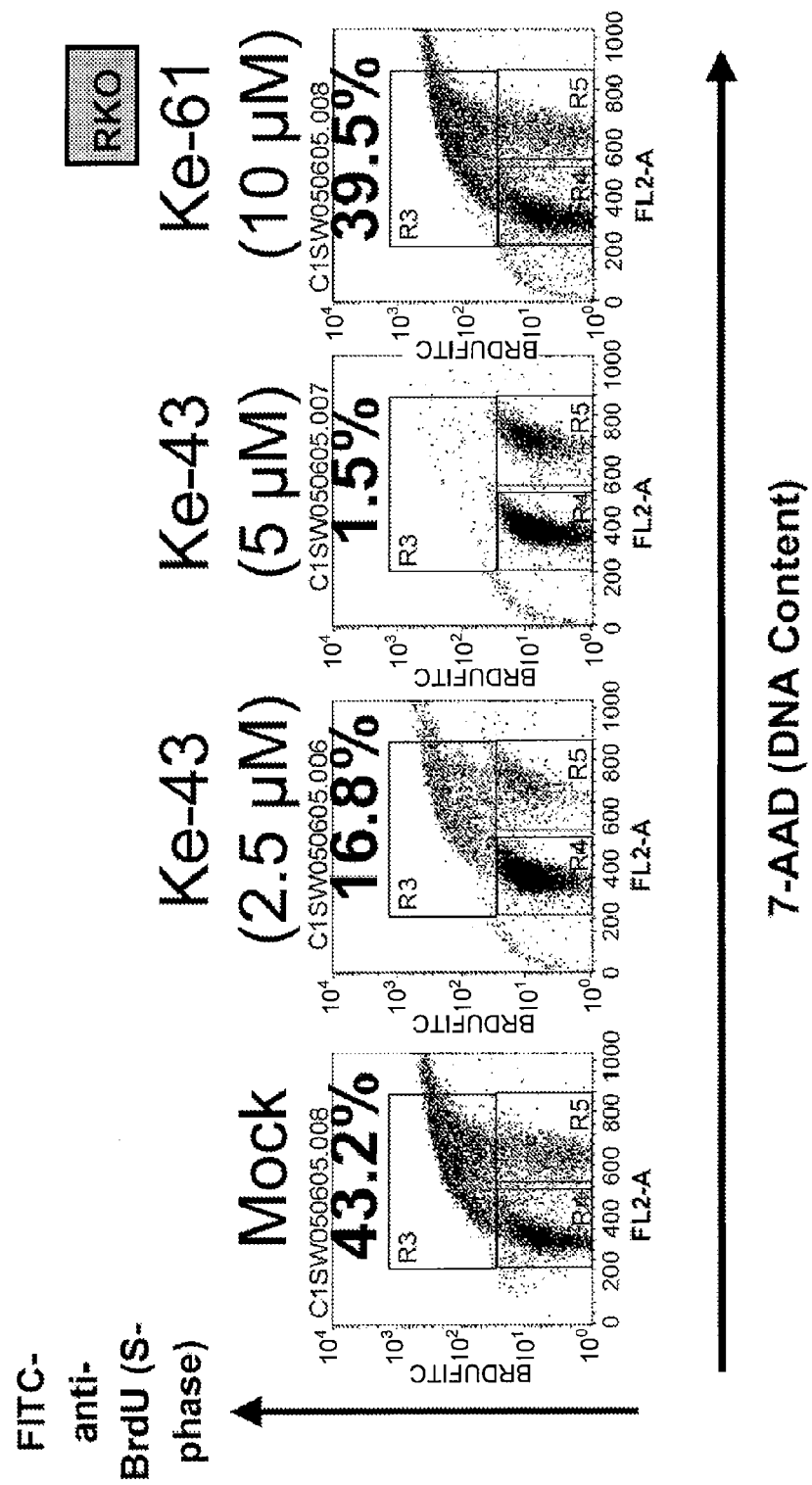
FIG. 14 shows cell cycle progression of colon cancer cell lines expressing wild-type p53 or mutant p53 and normal colon cells after treatment with Ke-43 and nutlin-3.
Figure 14:
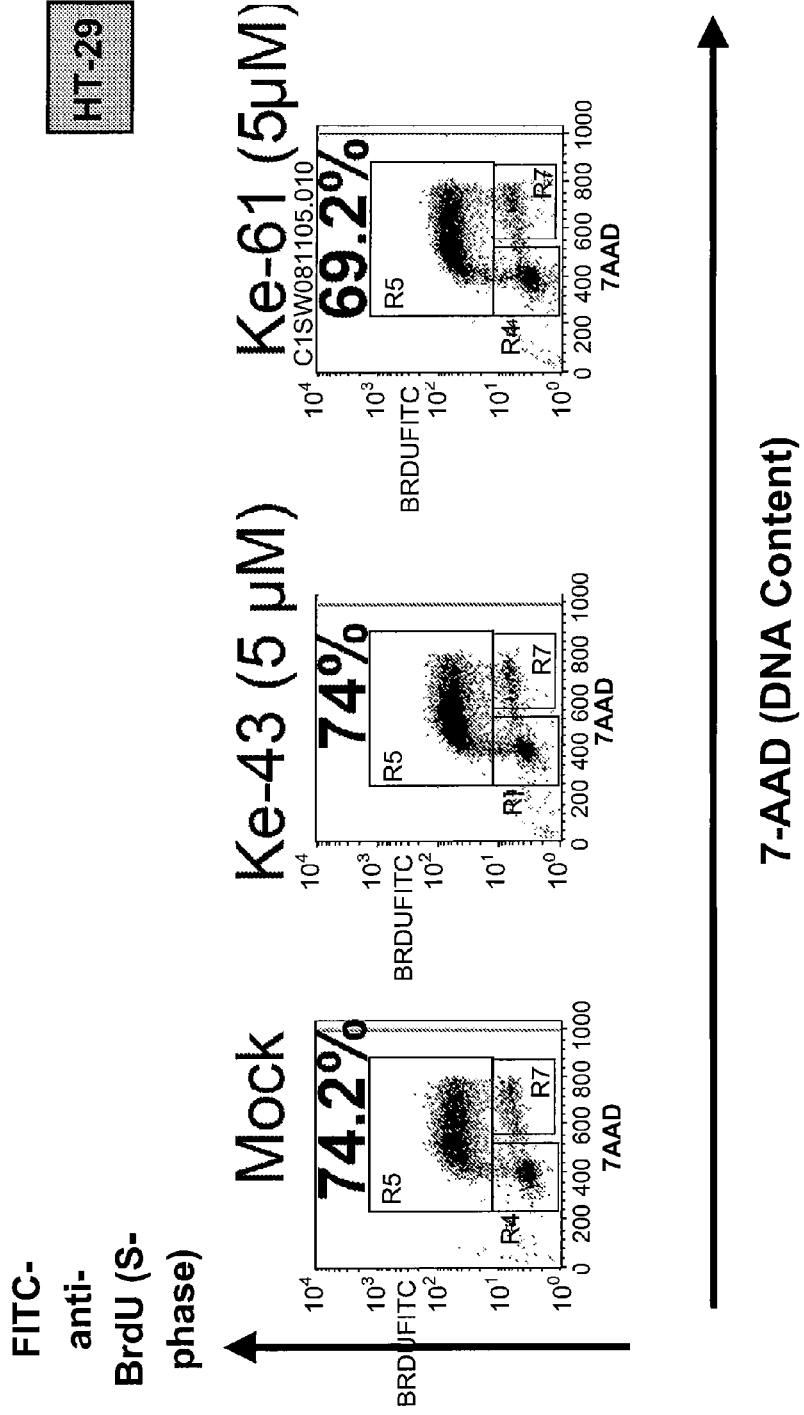
Figure 14:
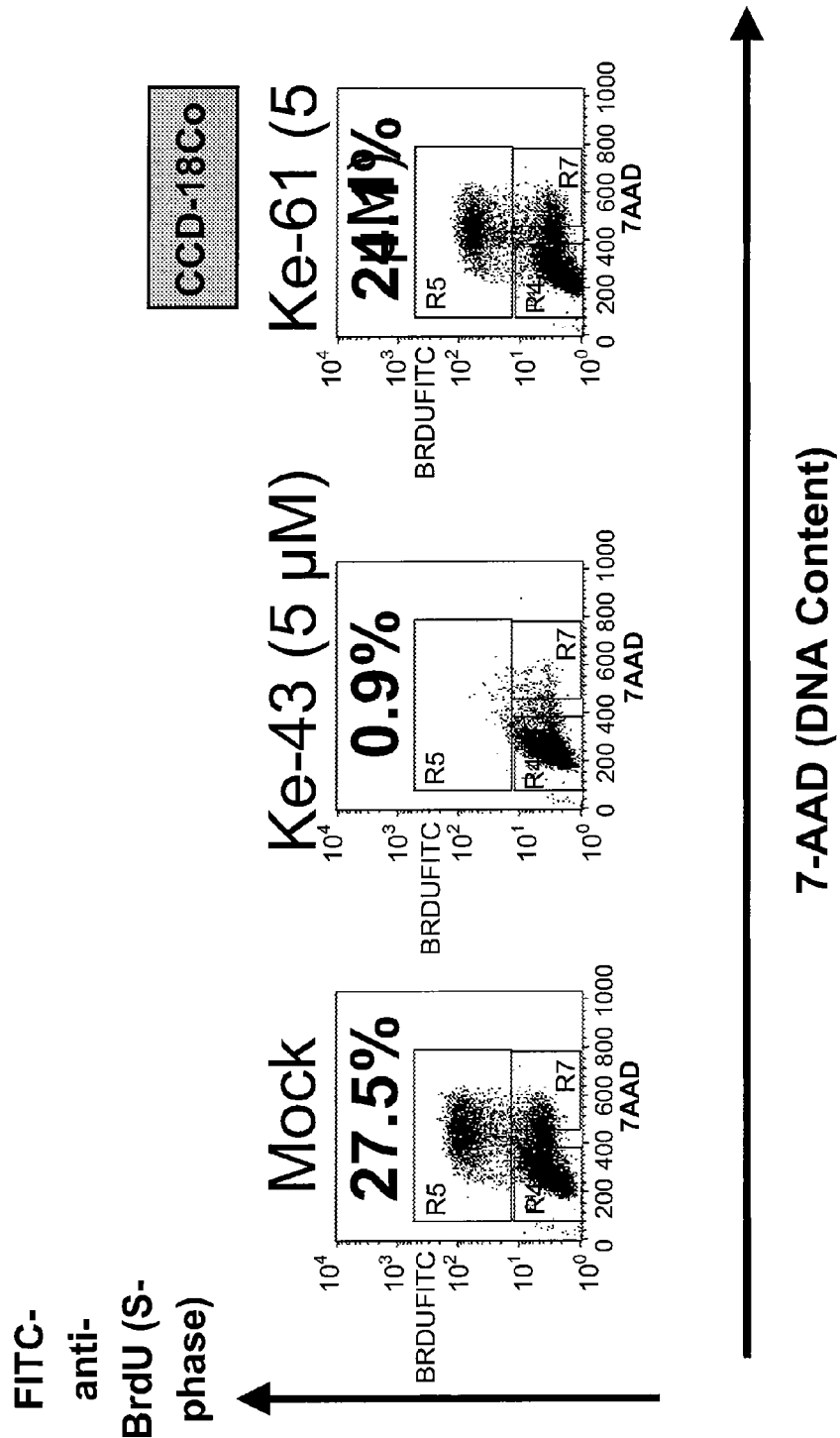

Cell cycle progression was evaluated in RKO (wild-type p53) and HT-29 (mutant p53) colon cancer cell lines and CCD-18Co normal colon fibroblast cells by determining S-phase cells by incorporation of bromodeoxyuridine (BrdU) followed by staining with FITC-labeled anti-BrdU antibody and the total DNA-content by staining with 7-aminoactinomycin D (7-AAD) according to manufacturer's instructions (BD Biosciences, San Jose, Calif.). Briefly, cancer and normal cells, after overnight incubation, were treated with out test compounds for 22 hours, followed by an additional 2 hours of incubation with 10 μM of BrdU. Cells were harvested, fixed and stained with FITC-labeled anti-BrdU and 7-AAD. Cell cycle distribution was analyzed by flow cytometry. Cells were acquired and data analyzed by using CellQuest software (BD Biosciences). Ke-43 induced a dose-dependent depletion of S-phase in RKO cancer cells and in CCD-18Co normal colon fibroblast cells, both of which express wild-type p53 (FIG. 14). However, Ke-43 had no appreciable effect on cell cycle progression of HT-29 cells expressing mutant p53 (FIG. 14). Inactive control inhibitor Ke-61 did not have a significant effect in all the tested cells.

Example 138

Protection of Normal Cells Form Chemotherapy with MDM2 Inhibitors

Figure 15:
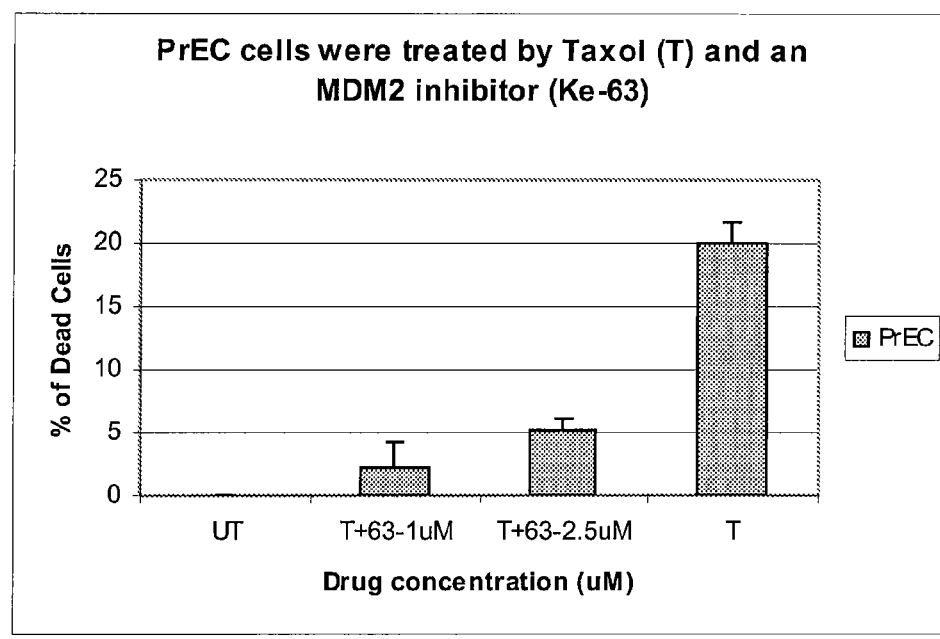
FIG. 15 shows protection of normal cells from TAXOL treatment by Ke-63.

PrEC normal prostate epithelial cells were seeded in 6 well pates and incubated with Ke-63 (1 μM and 2.5 μM) for 24 hours, then 1 μM TAXOL (paclitaxel) was added for 2 days. Trypan blue was used to determine cell viability. The data showed that when normal prostate epithelial cells were pre-treated with Ke-63, cells were protected from TAXOL (FIG. 15)

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. A method of treating or ameliorating colon cancer or prostate cancer in an animal, comprising administering to said animal a therapeutically effective amount of a compound having Formula X:

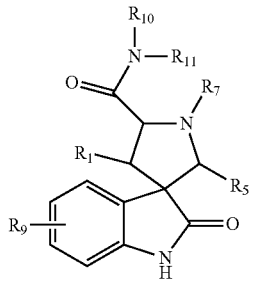

or a pharmaceutically acceptable salt thereof, wherein:

$R_1$ is optionally substituted cycloalkyl, alkenyl, cycloalkenyl, alkynyl, aryl, heterocyclic, $CO_2R'$, $OCOR'$, $CONR'R''$, $NR''COR'$, $NR'SO_2R''$, $SO_2NR'R''$, $(C=NR')NR''R'''$, or $NR'R''$;

$R_5$ and $R_7$ are independently H or optionally substituted alkyl, cycloalkyl, alkenyl, cycloalkenyl, alkynyl, aryl, heterocyclic, $CO_2R'$, $OCOR'$, $CONR'R''$, $NR''COR'$, $NR'SO_2R''$, $SO_2NR'R''$, $(C=NR')NR''R'''$, or $NR'R''$;

$R_9$ is one to four groups independently selected from H, F, Cl, Br, I, OH, $NO_2$, alkyl, cycloalkyl, alkenyl, cycloalkenyl, alkynyl, aryl, heterocyclic, $OR'$, $CO_2R'$, $OCOR'$, $CONR'R''$, $NR''COR'$, $NR'SO_2R''$, $SO_2NR'R''$, $(C=NR')NR''R'''$, or $NR'R''$; and each $R'$, $R''$ and $R'''$ is independently H or optionally substituted alkyl, cycloalkyl, alkenyl, cycloalkenyl, alkynyl, aryl, or heterocyclic; or $R'$ and $R''$, or $R''$ and $R'''$, form a ring;

$R_{10}$ and $R_{11}$ are independently H, $(CH_2)_n-R'$, $(CH_2)_n-NR'R''$, $(CH_2)_n-NR'COR''$, $(CH_2)_n-NR'SO_2R''$, $(CH_2)_n-NR'(C=NR'')NR'''$, $(CH_2)_n-COOH$, $(CH_2)_n-COOR'$, $(CH_2)_n-CONR'R''$, $(CH_2)_n-OR'$, $(CH_2)_n-SR'$, $(CH_2)_n-COR'$, $(CH_2)_n-SO_3H$, $(CH_2)_n-SONR'R''$, $(CH_2)_n-SO_2NR'R''$, $(CH_2CH_2O)_n-(CH_2)_m-OH$, $(CH_2CH_2O)_n-(CH_2)_m-OR'$, $(CH_2CH_2O)_n-(CH_2)_m-COOR'$, $(CH_2CH_2O)_n-(CH_2)_m-CONR'R''$, $(CH_2CH_2O)_n-(CH_2)_m-NR'R''$, $(CH_2CH_2O)_n-(CH_2)_m-NR'COR''$, $(CH_2CH_2O)_n-(CH_2)_m-NR'(C=NR'')NR'''$, $(CH_2CH_2O)_n-(CH_2)_m-NR'SO_2R''$, $(CH_2)_p-(CH_2CH_2O)_n-(CH_2)_m-OH$, $(CH_2)_p-(CH_2CH_2O)_n-(CH_2)_m-OR'$, $(CH_2)_p-(CH_2CH_2O)_n-(CH_2)_m-COOR'$, $(CH_2)_p-(CH_2CH_2O)_n-(CH_2)_m-CONR'R''$, $(CH_2)_p-(CH_2CH_2O)_n-(CH_2)_m-NR'R''$, $(CH_2)_p-(CH_2CH_2O)_n-(CH_2)_m-NR'COR''$, $(CH_2)_p-(CH_2CH_2O)_n-(CH_2)_m-NR'(C=NR'')NR'''$, or $(CH_2)_p-(CH_2CH_2O)_n-(CH_2)_m-NR'SO_2R''$; and n, m, and p are each independently 1-6.

2. The method of claim 1, further comprising administering an additional agent(s).

3. The method of claim 2, wherein said additional agent(s) is a chemotherapeutic agent.

4. The method of claim 2, wherein said additional agent(s) is radiation.

5. The method of claim 2, wherein said compound is administered prior to said additional agent(s).

6. The method of claim 2, wherein said compound is administered after said additional agent(s).

7. The method of claim 2, wherein said compound is administered concurrently with said additional agent(s).

* * * * *